(12) United States Patent
Salzer et al.

(10) Patent No.: US 8,920,619 B2
(45) Date of Patent: Dec. 30, 2014

(54) CARBON NANOTUBE SENSOR

(75) Inventors: Corey Alan Salzer, Fort Collins, CO (US); Russell Martin Young, Fort Collins, CO (US); Michael Mario Carrabba, Ashland, OR (US); Vishnu Vardhanan Rajasekharan, Fort Collins, CO (US); Christopher Patrick Fair, Windsor, CO (US); Terrance William Fitzgerald, Fort Collins, CO (US); Frank Howland Carpenter, Jr., Fort Collins, CO (US); John Edwin Lee, Fort Collins, CO (US)

(73) Assignee: Hach Company, Loveland, CO (US)

( * ) Notice: Subject to any disclaimer, the term of this patent is extended or adjusted under 35 U.S.C. 154(b) by 71 days.

(21) Appl. No.: 12/952,392

(22) Filed: Nov. 23, 2010

(65) Prior Publication Data
US 2012/0125771 A1    May 24, 2012

(51) Int. Cl.
*G01N 27/30* (2006.01)
*G01N 33/18* (2006.01)

(52) U.S. Cl.
CPC .......... *G01N 33/1886* (2013.01); *G01N 27/308* (2013.01); *C02F 2209/06* (2013.01); *C02F 2209/008* (2013.01); *C02F 2209/29* (2013.01)
USPC .................. 204/403.03; 204/403.01; 204/412

(58) Field of Classification Search
USPC ........ 204/403.01–403.15, 416–420, 431–435
See application file for complete search history.

(56) References Cited

U.S. PATENT DOCUMENTS

| | | |
|---|---|---|
| 4,626,992 A | 12/1986 | Greaves et al. |
| 4,830,757 A | 5/1989 | Lynch et al. |
| 5,227,038 A | 7/1993 | Smalley et al. |
| 5,242,602 A | 9/1993 | Richardson |
| 5,300,203 A | 4/1994 | Smalley |
| 5,315,880 A | 5/1994 | Bailey |
| 5,386,373 A | 1/1995 | Keeler et al. |
| 5,451,314 A | 9/1995 | Neuenschwander |
| 5,483,164 A | 1/1996 | Moss et al. |
| 5,492,632 A | 2/1996 | Reber |
| 5,494,573 A | 2/1996 | Schoenmeyr et al. |

(Continued)

FOREIGN PATENT DOCUMENTS

| | | |
|---|---|---|
| CA | 2283502 A1 | 9/1998 |
| EP | 0854839 A1 | 7/1998 |

(Continued)

OTHER PUBLICATIONS

Mohammad Mazloum Ardakani et al.; "Novel Coated-Wire Membrane Sensor Based on Bis(Acetylacetonato) Cadmium(II) for the Determination of Chromate Ions"; Department of Chemistry, Faculty of Science, Kashan University, Kashan, Iran; Received Jul. 24, 2004; accepted Nov. 16, 2004; published online Mar. 21, 2005 © Springer-Verlag 2005.

(Continued)

*Primary Examiner* — Bach Dinh
(74) *Attorney, Agent, or Firm* — Miles & Stockbridge P.C.; James T. Carmichael

(57) ABSTRACT

The present invention provides a remote monitoring system for monitoring the operation of a fluid treatment system and/or the qualities, characteristics, properties, etc., of the fluid being processed or treated by the fluid treatment system. The present invention also relates to carbon nanotube sensors.

9 Claims, 19 Drawing Sheets

(56) References Cited

U.S. PATENT DOCUMENTS

| | | | |
|---|---|---|---|
| 5,506,791 A | 4/1996 | Hungerford et al. | |
| 5,544,531 A | 8/1996 | Heckman | |
| 5,556,517 A | 9/1996 | Smalley | |
| 5,591,312 A | 1/1997 | Smalley | |
| 5,608,171 A | 3/1997 | Hunter et al. | |
| 5,619,631 A | 4/1997 | Schott | |
| 5,631,744 A | 5/1997 | Takeuchi et al. | |
| 5,633,809 A | 5/1997 | Wissenbach et al. | |
| 5,644,088 A | 7/1997 | Heckman | |
| 5,646,863 A | 7/1997 | Morton | |
| 5,681,482 A | 10/1997 | Reber | |
| 5,691,914 A | 11/1997 | Randolph | |
| 5,739,376 A | 4/1998 | Bingel | |
| 5,754,451 A | 5/1998 | Williams | |
| 5,757,659 A | 5/1998 | Arai et al. | |
| 5,811,688 A | 9/1998 | Marsh et al. | |
| 5,826,029 A | 10/1998 | Gore et al. | |
| 5,832,410 A | 11/1998 | Lin et al. | |
| 5,835,724 A | 11/1998 | Smith | |
| 5,865,718 A | 2/1999 | Chan | |
| 5,867,483 A | 2/1999 | Ennis et al. | |
| 5,905,570 A | 5/1999 | White et al. | |
| 5,960,404 A | 9/1999 | Chaar et al. | |
| 5,970,426 A | 10/1999 | Mandel et al. | |
| 5,993,662 A | 11/1999 | Garr et al. | |
| 5,997,750 A | 12/1999 | Rozelle et al. | |
| 6,023,223 A | 2/2000 | Baxter, Jr. | |
| 6,061,603 A | 5/2000 | Papadopoulos et al. | |
| 6,064,148 A | 5/2000 | Tolt et al. | |
| 6,097,995 A | 8/2000 | Tipton et al. | |
| 6,115,693 A | 9/2000 | McDonough et al. | |
| 6,129,901 A | 10/2000 | Moskovits et al. | |
| 6,149,775 A | 11/2000 | Tsuboi et al. | |
| 6,162,926 A | 12/2000 | Murphy et al. | |
| 6,167,376 A | 12/2000 | Ditzik | |
| 6,183,714 B1 | 2/2001 | Smalley et al. | |
| 6,208,943 B1 | 3/2001 | Randolph et al. | |
| 6,222,839 B1 | 4/2001 | Nakazaki et al. | |
| 6,265,466 B1 | 7/2001 | Glatkowski et al. | |
| 6,305,944 B1 | 10/2001 | Henry et al. | |
| 6,317,639 B1 | 11/2001 | Hansen | |
| 6,332,110 B1 | 12/2001 | Wolfe | |
| 6,346,023 B1 | 2/2002 | Tsuboi et al. | |
| 6,356,205 B1 | 3/2002 | Salvo et al. | |
| 6,359,444 B1 | 3/2002 | Grimes | |
| 6,370,448 B1 | 4/2002 | Eryurek | |
| 6,389,331 B1 | 5/2002 | Jensen et al. | |
| 6,399,785 B1 | 6/2002 | Murphy et al. | |
| 6,401,526 B1 | 6/2002 | Dai et al. | |
| 6,448,412 B1 | 9/2002 | Murphy et al. | |
| 6,463,352 B1 | 10/2002 | Tadokoro et al. | |
| 6,493,208 B1 | 12/2002 | Piche et al. | |
| 6,509,619 B1 | 1/2003 | Kendall et al. | |
| 6,530,160 B1 | 3/2003 | Gookins | |
| 6,538,153 B1 | 3/2003 | Hirsch et al. | |
| 6,560,543 B2 | 5/2003 | Wolfe et al. | |
| 6,577,988 B1 | 6/2003 | Travagline et al. | |
| 6,606,566 B1 | 8/2003 | Sunshine | |
| 6,618,709 B1 | 9/2003 | Sneeringer | |
| 6,645,455 B2 | 11/2003 | Margrave et al. | |
| 6,659,861 B1 | 12/2003 | Faris et al. | |
| 6,672,077 B1 | 1/2004 | Bradley et al. | |
| 6,673,314 B1 | 1/2004 | Burbank et al. | |
| 6,675,127 B2 | 1/2004 | LaBlanc et al. | |
| 6,683,783 B1 | 1/2004 | Smalley et al. | |
| 6,692,717 B1 | 2/2004 | Smalley et al. | |
| 6,712,864 B2 | 3/2004 | Horiuchi et al. | |
| 6,725,250 B1 | 4/2004 | Ellis, III | |
| 6,743,408 B2 | 6/2004 | Lieber et al. | |
| 6,748,748 B2 | 6/2004 | Bradley et al. | |
| 6,749,827 B2 | 6/2004 | Smalley et al. | |
| 6,752,977 B2 | 6/2004 | Smalley et al. | |
| 6,756,025 B2 | 6/2004 | Colbert et al. | |
| 6,756,026 B2 | 6/2004 | Colbert et al. | |
| 6,761,870 B1 | 7/2004 | Smalley et al. | |
| 6,762,237 B2 | 7/2004 | Glatkowski et al. | |
| 6,790,425 B1 | 9/2004 | Smalley et al. | |
| 6,811,457 B2 | 11/2004 | Cheng et al. | |
| 6,824,755 B2 | 11/2004 | Colbert et al. | |
| 6,827,918 B2 | 12/2004 | Margrave et al. | |
| 6,830,679 B2 | 12/2004 | Tsuihiji et al. | |
| 6,835,366 B1 | 12/2004 | Margrave et al. | |
| 6,836,737 B2 | 12/2004 | Petite et al. | |
| 6,841,139 B2 | 1/2005 | Margrave et al. | |
| 6,845,336 B2 | 1/2005 | Kodukula et al. | |
| 6,847,739 B2 | 1/2005 | Jostschulte | |
| 6,852,410 B2 | 2/2005 | Veedu et al. | |
| 6,858,197 B1 | 2/2005 | Delzeit | |
| 6,863,942 B2 | 3/2005 | Ren et al. | |
| 6,872,330 B2 | 3/2005 | Mack et al. | |
| 6,875,412 B2 | 4/2005 | Margrave et al. | |
| 6,885,309 B1 | 4/2005 | Van Heteren | |
| 6,890,506 B1 | 5/2005 | Harutyunyan et al. | |
| 6,894,359 B2 | 5/2005 | Bradley et al. | |
| 6,899,945 B2 | 5/2005 | Smalley et al. | |
| 6,900,264 B2 | 5/2005 | Kumar et al. | |
| 6,904,054 B1 | 6/2005 | Baum et al. | |
| 6,913,789 B2 | 7/2005 | Smalley et al. | |
| 6,921,575 B2 | 7/2005 | Horiuchi et al. | |
| 6,936,233 B2 | 8/2005 | Smalley et al. | |
| 6,936,653 B2 | 8/2005 | McElrath et al. | |
| 6,939,525 B2 | 9/2005 | Colbert et al. | |
| 6,947,427 B1 | 9/2005 | Rokugo et al. | |
| 6,949,237 B2 | 9/2005 | Smalley et al. | |
| 6,954,701 B2 | 10/2005 | Wolfe | |
| 6,961,641 B1 | 11/2005 | Forth et al. | |
| 6,969,504 B2 | 11/2005 | Smalley et al. | |
| 6,978,212 B1 | 12/2005 | Sunshine | |
| 6,979,709 B2 | 12/2005 | Smalley et al. | |
| 6,986,853 B2 | 1/2006 | Glatkowski et al. | |
| 6,986,876 B2 | 1/2006 | Smalley et al. | |
| 6,988,925 B2 | 1/2006 | Arthur et al. | |
| 7,008,563 B2 | 3/2006 | Smalley et al. | |
| 7,008,604 B2 | 3/2006 | Smalley et al. | |
| 7,014,737 B2 | 3/2006 | Harutyunyan et al. | |
| 7,029,646 B2 | 4/2006 | Margrave et al. | |
| 7,036,324 B2 | 5/2006 | Bradley et al. | |
| 7,041,620 B2 | 5/2006 | Smalley et al. | |
| 7,048,903 B2 | 5/2006 | Colbert et al. | |
| 7,048,999 B2 | 5/2006 | Smalley et al. | |
| 7,049,353 B2 | 5/2006 | Conroy et al. | |
| 7,052,666 B2 | 5/2006 | Colbert et al. | |
| 7,052,668 B2 | 5/2006 | Smalley et al. | |
| 7,058,154 B1 | 6/2006 | Stark et al. | |
| 7,060,241 B2 | 6/2006 | Glatkowski | |
| 7,061,749 B2 | 6/2006 | Liu et al. | |
| 7,067,098 B2 | 6/2006 | Colbert et al. | |
| 7,070,651 B1 | 7/2006 | Tolt et al. | |
| 7,070,754 B2 | 7/2006 | Smalley et al. | |
| 7,070,810 B2 | 7/2006 | Hirsch et al. | |
| 7,071,406 B2 | 7/2006 | Smalley et al. | |
| 7,074,310 B2 | 7/2006 | Smalley et al. | |
| 7,076,871 B2 | 7/2006 | Horiuchi et al. | |
| 7,085,938 B1 | 8/2006 | Pozzuoli et al. | |
| 7,087,207 B2 | 8/2006 | Smalley et al. | |
| 7,090,819 B2 | 8/2006 | Smalley et al. | |
| 7,094,679 B1 | 8/2006 | Li et al. | |
| 7,108,841 B2 | 9/2006 | Smalley et al. | |
| 7,118,693 B2 | 10/2006 | Glatkowski et al. | |
| 7,121,158 B2 * | 10/2006 | Scott et al. | 73/866.5 |
| 7,147,966 B2 | 12/2006 | Ren et al. | |
| 7,160,532 B2 | 1/2007 | Liu et al. | |
| 7,176,877 B2 | 2/2007 | Tikhonski et al. | |
| 7,179,561 B2 | 2/2007 | Niu et al. | |
| 7,182,914 B2 | 2/2007 | Lai et al. | |
| 7,189,314 B1 * | 3/2007 | Pace et al. | 204/412 |
| 7,189,430 B2 | 3/2007 | Ajayan et al. | |
| 7,195,754 B1 | 3/2007 | Glatkowski et al. | |
| 7,204,970 B2 | 4/2007 | Smalley et al. | |
| 7,217,650 B1 | 5/2007 | Ng et al. | |
| 7,227,140 B2 | 6/2007 | Skidmore et al. | |
| 7,250,148 B2 | 7/2007 | Yang et al. | |
| 7,276,266 B1 | 10/2007 | Khare et al. | |
| 7,282,191 B1 | 10/2007 | Choi et al. | |

(56) References Cited

U.S. PATENT DOCUMENTS

| | | | |
|---|---|---|---|
| 7,285,198 B2 | 10/2007 | Douglas |
| 7,303,875 B1 | 12/2007 | Bock et al. |
| 7,338,648 B2 | 3/2008 | Harutyunyan et al. |
| 7,338,915 B1 | 3/2008 | Smalley et al. |
| 7,342,479 B2 | 3/2008 | Glatkowski et al. |
| 7,342,506 B2 | 3/2008 | Paoli et al. |
| 7,345,307 B2 | 3/2008 | Pan et al. |
| 7,354,563 B2 | 4/2008 | Smalley et al. |
| 7,357,906 B2 | 4/2008 | Colbert et al. |
| 7,357,983 B2 | 4/2008 | Pfefferle |
| 7,365,395 B2 | 4/2008 | Stumbo et al. |
| 7,378,040 B2 | 5/2008 | Luo et al. |
| 7,390,477 B2 | 6/2008 | Smalley et al. |
| 7,390,767 B2 | 6/2008 | Smalley et al. |
| 7,426,848 B1 | 9/2008 | Li et al. |
| 7,428,046 B2 | 9/2008 | Wang et al. |
| 7,449,757 B2 | 11/2008 | Bradley et al. |
| 7,452,452 B2 | 11/2008 | Ren et al. |
| 7,452,735 B2 | 11/2008 | Li et al. |
| 7,454,295 B2 | 11/2008 | Wolfe |
| 7,465,494 B2 | 12/2008 | Ren et al. |
| 7,466,533 B2 | 12/2008 | Chow et al. |
| 7,468,315 B2 | 12/2008 | Buretea et al. |
| 7,470,620 B2 | 12/2008 | Dubin et al. |
| 7,473,411 B2 | 1/2009 | Ajayan et al. |
| 7,473,436 B1 | 1/2009 | Khare et al. |
| 7,479,240 B2 | 1/2009 | Jhi et al. |
| 7,485,678 B2 | 2/2009 | Ohashi et al. |
| 7,514,369 B2 | 4/2009 | Li et al. |
| 7,515,333 B1 | 4/2009 | Empedocles |
| 7,522,040 B2 | 4/2009 | Passmore et al. |
| 7,553,371 B2 | 6/2009 | Dubrow et al. |
| 7,553,471 B2 | 6/2009 | Ohashi et al. |
| 7,557,028 B1 | 7/2009 | Scher et al. |
| 7,560,134 B2 | 7/2009 | Yaniv et al. |
| 7,560,136 B2 | 7/2009 | Ward et al. |
| 7,560,366 B1 | 7/2009 | Romano et al. |
| 7,563,722 B2 | 7/2009 | Yaniv et al. |
| 7,566,945 B2 | 7/2009 | Choi et al. |
| 7,569,503 B2 | 8/2009 | Pan et al. |
| 7,575,720 B2 | 8/2009 | Novak et al. |
| 7,575,933 B2 | 8/2009 | Gabriel et al. |
| 7,581,645 B2 | 9/2009 | Ho et al. |
| 7,595,528 B2 | 9/2009 | Duan et al. |
| 7,596,415 B2 | 9/2009 | Brabec et al. |
| 7,597,788 B2 | 10/2009 | Visel et al. |
| 7,611,740 B2 | 11/2009 | Jiang et al. |
| 7,611,906 B2 | 11/2009 | Yaniv |
| 7,623,972 B1 | 11/2009 | Li et al. |
| 7,628,974 B2 | 12/2009 | Grill et al. |
| 7,630,227 B2 | 12/2009 | Tran |
| 7,632,548 B2 | 12/2009 | Yaniv |
| 7,635,503 B2 | 12/2009 | Dominguez et al. |
| 7,641,938 B2 | 1/2010 | Liu et al. |
| 7,645,397 B2 | 1/2010 | Parce et al. |
| 7,647,813 B2 | 1/2010 | Pavlovsky |
| 7,651,769 B2 | 1/2010 | Dubrow |
| 7,651,944 B2 | 1/2010 | Duan et al. |
| 7,652,418 B2 | 1/2010 | Choi et al. |
| 7,655,497 B1 | 2/2010 | Yu et al. |
| 7,667,296 B2 | 2/2010 | Stumbo et al. |
| 7,687,981 B2 | 3/2010 | Parsapour |
| 7,691,720 B2 | 4/2010 | Furukawa et al. |
| 7,695,609 B2 | 4/2010 | Soundarrajan et al. |
| 7,696,272 B2 | 4/2010 | Li et al. |
| 7,698,073 B2 | 4/2010 | Wolfe |
| 7,701,014 B2 | 4/2010 | Mostarshed et al. |
| 7,701,428 B2 | 4/2010 | Stumbo et al. |
| 7,704,479 B2 | 4/2010 | Rinzler et al. |
| 7,704,547 B1 | 4/2010 | Delzeit et al. |
| 7,714,386 B2 | 5/2010 | Pesetski et al. |
| 7,714,398 B2 | 5/2010 | Ben-Barak et al. |
| 7,728,520 B2 | 6/2010 | Yaniv et al. |
| 7,736,209 B2 | 6/2010 | Mao et al. |
| 7,736,979 B2 | 6/2010 | Farrow et al. |
| 7,741,197 B1 | 6/2010 | Duan et al. |
| 7,745,498 B2 | 6/2010 | Pereira et al. |
| 7,749,477 B2 | 7/2010 | Jiang et al. |
| 7,750,235 B2 | 7/2010 | Scher et al. |
| 7,754,524 B2 | 7/2010 | Dubrow et al. |
| 7,755,038 B2 | 7/2010 | Niu et al. |
| 7,755,115 B2 | 7/2010 | Awano |
| 7,762,121 B2 | 7/2010 | Ng et al. |
| 7,767,067 B2 * | 8/2010 | Silveri ............... 204/406 |
| 7,767,102 B2 | 8/2010 | Lemmi et al. |
| 7,767,270 B1 | 8/2010 | Khare et al. |
| 7,776,758 B2 | 8/2010 | Duan et al. |
| 7,776,760 B2 | 8/2010 | Taylor |
| 7,782,462 B2 | 8/2010 | Pavlovsky |
| 7,784,531 B1 | 8/2010 | Li et al. |
| 7,785,922 B2 | 8/2010 | Robbins |
| 7,786,024 B2 | 8/2010 | Stumbo et al. |
| 7,786,402 B2 | 8/2010 | Fink et al. |
| 7,791,258 B2 | 9/2010 | Yaniv et al. |
| 7,794,600 B1 | 9/2010 | Buretea et al. |
| 7,795,125 B2 | 9/2010 | Buretea et al. |
| 7,801,687 B1 | 9/2010 | Li et al. |
| 8,504,205 B2 | 8/2013 | Summer et al. |
| 2001/0020195 A1 | 9/2001 | Patel et al. |
| 2001/0053992 A1 | 12/2001 | Eto et al. |
| 2001/0055978 A1 | 12/2001 | Herrod et al. |
| 2002/0023479 A1 | 2/2002 | Burge et al. |
| 2002/0130069 A1 | 9/2002 | Moskoff |
| 2002/0133270 A1 | 9/2002 | Hung et al. |
| 2003/0052585 A1 | 3/2003 | Guillorn et al. |
| 2003/0089899 A1 | 5/2003 | Lieber et al. |
| 2003/0124717 A1 | 7/2003 | Awano et al. |
| 2003/0174070 A1 | 9/2003 | Garrod et al. |
| 2003/0207326 A1 | 11/2003 | Su et al. |
| 2004/0026684 A1 | 2/2004 | Empedocles |
| 2004/0066313 A1 | 4/2004 | Ong et al. |
| 2004/0117731 A1 | 6/2004 | Blyashov |
| 2004/0132070 A1 | 7/2004 | Star et al. |
| 2004/0136866 A1 | 7/2004 | Pontis et al. |
| 2004/0245209 A1 | 12/2004 | Jung et al. |
| 2005/0046017 A1 | 3/2005 | Dangelo |
| 2005/0136483 A1 | 6/2005 | Carlson |
| 2005/0186333 A1 | 8/2005 | Douglas |
| 2005/0221473 A1 | 10/2005 | Dubin et al. |
| 2005/0224220 A1 | 10/2005 | Li et al. |
| 2005/0269285 A1 | 12/2005 | Jung et al. |
| 2005/0273424 A1 | 12/2005 | Silverman et al. |
| 2006/0014155 A1 * | 1/2006 | Hamers et al. ............ 435/6 |
| 2006/0078468 A1 * | 4/2006 | Gabriel et al. ........... 422/88 |
| 2006/0112983 A1 | 6/2006 | Parce et al. |
| 2006/0124028 A1 | 6/2006 | Huang et al. |
| 2006/0240218 A1 | 10/2006 | Parce |
| 2006/0257637 A1 | 11/2006 | Pereira et al. |
| 2006/0275914 A1 | 12/2006 | Henley et al. |
| 2006/0287906 A1 | 12/2006 | McGillin |
| 2007/0044295 A1 | 3/2007 | Chen |
| 2007/0045128 A1 * | 3/2007 | Krafthefer et al. ......... 205/778.5 |
| 2007/0132043 A1 | 6/2007 | Bradley et al. |
| 2007/0140930 A1 | 6/2007 | Novak et al. |
| 2007/0155064 A1 | 7/2007 | Chen et al. |
| 2007/0163965 A1 | 7/2007 | Wolfe |
| 2007/0238006 A1 | 10/2007 | Vyas et al. |
| 2007/0238209 A1 | 10/2007 | Yaniv et al. |
| 2007/0246364 A1 | 10/2007 | Amlani et al. |
| 2008/0035481 A1 | 2/2008 | McCormack et al. |
| 2008/0089829 A1 | 4/2008 | Ganapathiraman et al. |
| 2008/0142361 A1 | 6/2008 | Han et al. |
| 2008/0150009 A1 | 6/2008 | Chen |
| 2008/0152839 A1 | 6/2008 | Han et al. |
| 2008/0213367 A1 | 9/2008 | Sarkar et al. |
| 2008/0221806 A1 | 9/2008 | Bryant et al. |
| 2008/0237540 A1 | 10/2008 | Dubrow |
| 2008/0246076 A1 | 10/2008 | Chen |
| 2008/0280069 A1 | 11/2008 | Parce et al. |
| 2008/0280780 A1 | 11/2008 | Hamers et al. |
| 2008/0317631 A1 | 12/2008 | Farrow et al. |
| 2009/0035570 A1 | 2/2009 | Mao et al. |
| 2009/0045061 A1 | 2/2009 | Farrow et al. |
| 2009/0058431 A1 | 3/2009 | Dass et al. |

(56) References Cited

U.S. PATENT DOCUMENTS

| | | |
|---|---|---|
| 2009/0072192 A1 | 3/2009 | Seal et al. |
| 2009/0095704 A1 | 4/2009 | Mao et al. |
| 2009/0123343 A1 | 5/2009 | Kwiatkowski |
| 2009/0124025 A1 | 5/2009 | Hamilton et al. |
| 2009/0138240 A1 | 5/2009 | Wolfe |
| 2009/0192429 A1 | 7/2009 | Daniels et al. |
| 2009/0198117 A1 | 8/2009 | Cooper et al. |
| 2009/0230380 A1 | 9/2009 | Leon et al. |
| 2009/0242429 A1 | 10/2009 | Sitdikov et al. |
| 2009/0242854 A1 | 10/2009 | Li et al. |
| 2009/0252886 A1 | 10/2009 | Barker et al. |
| 2009/0261186 A1 | 10/2009 | Fink et al. |
| 2009/0274833 A1 | 11/2009 | Li et al. |
| 2009/0275826 A1 | 11/2009 | Enzerink et al. |
| 2009/0278556 A1* | 11/2009 | Man et al. ............... 324/693 |
| 2009/0286383 A1 | 11/2009 | Jiang et al. |
| 2009/0301993 A1 | 12/2009 | Feng et al. |
| 2009/0325370 A1 | 12/2009 | Yang et al. |
| 2010/0000762 A1 | 1/2010 | Yang et al. |
| 2010/0055349 A1 | 3/2010 | Gaitas et al. |
| 2010/0062178 A1 | 3/2010 | Zhang et al. |
| 2010/0068406 A1 | 3/2010 | Man |
| 2010/0072429 A1 | 3/2010 | Rajala et al. |
| 2010/0089122 A1 | 4/2010 | Abdullah et al. |
| 2010/0102245 A1 | 4/2010 | Jiang et al. |
| 2010/0104808 A1 | 4/2010 | Fan et al. |
| 2010/0116666 A1 | 5/2010 | Park et al. |
| 2010/0127167 A1 | 5/2010 | Schropp, Jr. et al. |
| 2010/0128205 A1 | 5/2010 | Rho et al. |
| 2010/0140213 A1 | 6/2010 | Mizukami et al. |
| 2010/0143234 A1 | 6/2010 | Kajiura et al. |
| 2010/0153021 A1 | 6/2010 | Wolfe |
| 2010/0167011 A1 | 7/2010 | Dubrow |
| 2010/0167512 A1 | 7/2010 | Pan et al. |
| 2010/0173228 A1 | 7/2010 | Wallace et al. |
| 2010/0204924 A1 | 8/2010 | Wolfe et al. |
| 2010/0332149 A1 | 12/2010 | Scholpp |
| 2011/0125412 A1 | 5/2011 | Salzer et al. |
| 2012/0125771 A1 | 5/2012 | Salzer et al. |
| 2013/0009781 A1 | 1/2013 | Wolfe |
| 2013/0013259 A1 | 1/2013 | Wolfe |
| 2013/0073611 A1 | 3/2013 | Wolfe |

FOREIGN PATENT DOCUMENTS

| | | |
|---|---|---|
| EP | 1015384 A1 | 7/2000 |
| EP | 1404908 | 11/2007 |
| EP | 1623437 B1 | 12/2007 |
| EP | 1864122 A2 | 12/2007 |
| EP | 1954387 A2 | 8/2008 |
| EP | 1976431 A2 | 10/2008 |
| EP | 1836104 B1 | 1/2009 |
| EP | 2018549 A2 | 1/2009 |
| EP | 2047531 A2 | 4/2009 |
| EP | 2012589 B1 | 7/2009 |
| EP | 2083928 A1 | 8/2009 |
| EP | 1556878 B1 | 4/2010 |
| JP | 2003/100202 A | 4/2003 |
| JP | 3958792 | 8/2007 |
| JP | 3962376 | 8/2007 |
| JP | 2008/260073 | 10/2008 |
| JP | 4381428 B2 | 12/2009 |
| WO | WO 97/09272 A1 | 3/1997 |
| WO | WO97/09272 A1 | 3/1997 |
| WO | WO 00/036412 A1 | 6/2000 |
| WO | WO 01/80494 | 10/2001 |
| WO | WO03024798 A1 | 3/2003 |
| WO | WO 03/038685 A2 | 5/2003 |
| WO | WO03050036 A1 | 6/2003 |
| WO | WO03/078317 A1 | 9/2003 |
| WO | WO 03/078317 A1 | 9/2003 |
| WO | WO2004024407 A1 | 3/2004 |
| WO | WO2004052559 A2 | 6/2004 |
| WO | WO2004069737 A2 | 8/2004 |
| WO | WO 2004/097853 A1 | 11/2004 |
| WO | WO 2005/022120 A2 | 3/2005 |
| WO | WO2005022120 A2 | 3/2005 |
| WO | WO2005-079202 A2 | 9/2005 |
| WO | WO2005-086982 A2 | 9/2005 |
| WO | WO2005-110624 A2 | 11/2005 |
| WO | WO2006/069458 A1 | 7/2006 |
| WO | WO 2006/069458 A1 | 7/2006 |
| WO | WO2006-073420 A2 | 7/2006 |
| WO | WO2006078286 A2 | 7/2006 |
| WO | WO 2006/102064 A2 | 9/2006 |
| WO | WO2006/102064 A2 | 9/2006 |
| WO | WO2007024697 A2 | 3/2007 |
| WO | WO2007/067922 A2 | 6/2007 |
| WO | WO 2007/067922 A2 | 6/2007 |
| WO | WO2007-106836 A2 | 9/2007 |
| WO | WO2007/124612 A2 | 11/2007 |
| WO | WO 2007/124612 A2 | 11/2007 |
| WO | WO2008-051205 A2 | 5/2008 |
| WO | WO2008057615 A2 | 5/2008 |
| WO | WO2008060455 A3 | 5/2008 |
| WO | WO2008076473 A2 | 6/2008 |
| WO | WO2008091402 A2 | 7/2008 |
| WO | WO2008106426 A9 | 9/2008 |
| WO | WO2008143714 A2 | 11/2008 |
| WO | WO2008150336 A2 | 12/2008 |
| WO | WO2009011450 A1 | 1/2009 |
| WO | WO2009023061 A2 | 2/2009 |
| WO | WO2009042079 A2 | 4/2009 |
| WO | WO2010003212 A1 | 1/2010 |
| WO | WO2010048405 A1 | 4/2010 |
| WO | WO2010048407 A1 | 4/2010 |
| WO | WO2010056826 A1 | 5/2010 |
| WO | WO2010077226 A1 | 7/2010 |
| WO | WO2010093703 A1 | 8/2010 |
| WO | WO2010096035 A1 | 8/2010 |
| WO | WO 2010/098422 A1 | 9/2010 |
| WO | WO 2012/069993 A2 | 5/2012 |
| WO | WO 2012/069992 A2 | 9/2012 |

OTHER PUBLICATIONS

R. Schüler et al.; Modified gas-permeable silicone rubber membranes for covalent immobilisation of enzymes and their use in biosensor development ICB, Institut für Chemo- und Biosensorik, eV, Mendelstrasse 7, D-48149 Münster, Germany Received Apr. 13, 1999, Accepted Jun. 18, 1999.

Farnoush Faridbod et al.; "The fabrication of potentiometric membrane sensors and their applications"; 1Center of Excellence in Electrochemistry, Faculty of Chemistry, University of Tehran, Tehran, Iran. 2Medical Nanotechnology Research Centre, Medical Sciences/ University of Tehran, Tehran, P.O. Box 14155-6451, Iran. Accepted Nov. 12, 2007; African Journal of Biotechnology vol. 6 (25), pp. 2960-2987, Dec. 28, 2007 Available online at http://www.academicjournals.org/AJ; ISSN 1684-5315 © 2007 Academic Journals.

Zbigniew Moron; "Considerations on the Accuracy of Measurements of Electrical Conductivity of Liquids"; Department of Biomedical Engineering and Instrumentation, Wroclaw University of Technology, Wroclaw, Poland; XVIII IMEKO World Congress Metrology for a Sustainable Development Sep. 17-22, 2006, Rio de Janeiro, Brazil.

Lee Yook Heng et al.; "Producing "Self-Plasticizing" Ion-Selective Membranes"; Institute of Biotechnology, University of Cambridge, Tennis Court Road, Cambridge CB2 1QT, U.K. Anal. Chem. 2000, 72, 42-51.

Erno Pretsch et al.; "Design features of ionophores for ion selective electrodes"; Department of Organic Chemistry, Swiss Federal Institute of Technology (ETH), Universitatstrasse 16, CH-8092 Zurich, Switzerland; Pure & Appl. Chem., vol. 60, No. 4, pp. 567-574, 1988, Printed in Great Britain © 1998 IUPAC.

E. Pretsch et al.; "Design features of inophores for ion selective electrodes"; pp. 574-574.

Liu et al., Caron Nanotubes in Biology and Medicine: In vitro and in vivo Detection, Imaging and Drug Delivery; Nano Res, vol. 2, pp. 85-120 (2009).

(56) References Cited

OTHER PUBLICATIONS

Tzeng et al., "Hydration Properties of Carbon Nanotubes and Their Effects on Electrical and Biosensor Applications", *New Diamond and Frontier Carbon Technology*, vol. 14, No. 3, pp. 193-201 (2004).
Nonfinal office Action dated Jan. 31, 2013, in U.S. Appl. No. 13/619,880.
Nonfinal Office Action dated Mar. 4, 2013, in U.S. Appl. No. 13/619,775.
Nonfinal Office Action dated Mar. 5, 2013, in U.S. Appl. No. 13/620,000.
International Preliminary Report on Patentability dated Jun. 6, 2013, in PCT/IB2011/055240.
International Preliminary Report on Patentability dated Jun. 6, 2013, in PCT/IB2011/055238.
French Search Report dated May 29, 2013, in French Patent Application No. 11 6066.
International Search Report and Written Opinion dated Jul. 10, 2012, in Application No. PCT/IB2011/055238.
International Search Report and Written Opinion dated Aug. 30, 2012, in Application No. PCT/IB/055240.
U.S. Appl. No. 09/213,781, filed Dec. 17, 1998, now U.S. Patent No. 6,332,110.
U.S. Appl. No. 10/055,225, filed Oct. 26, 2001, now U.S. Patent No. 6,560,543.
U.S. Appl. No. 10/392,112, filed Mar. 19, 2003, now U.S. Patent No. 7,454,295.
U.S. Appl. No. 10/695,627, filed Oct. 27, 2003, now U.S. Patent No. 6,954,701.
U.S. Appl. No. 11/331,721, filed Jan. 13, 2006.
U.S. Appl. No. 12/272,018, filed Nov. 17, 2008, now U.S. Patent No. 7,698,073.
U.S. Appl. No. 12/565,091, filed Sep. 23, 2009.
U.S. Appl. No. 12/710,451, filed Feb. 23, 2010.
U.S. Appl. No. 12/874,293, filed Sep. 2, 2010.
U.S. Appl. No. 12/952,566, filed Nov. 23, 2010.
U.S. Appl. No. 13/619,775, filed Sep. 14, 2012.
U.S. Appl. No. 13/620,000, filed Sep. 14, 2012.
U.S. Appl. No. 13/619,880, filed Sep. 14, 2012.
Cycliax, Ingo, "Remote Internet Data Logging and Sensing", Circuit Cellar Magazine, Embedded PC, PC/104 Quarter104, Nov. 1997, pp. 53-59.
McKinnon, et al., "Automating Communications with and Developing User Interfaces for Remote data Acquisition and Analysis Systems", IEEE Transactions on Nuclear Science, vol. 44, No. 3, Jun. 1997, pp. 1062-1064.
Franklin, et al., "Data in Your Face": Push Technology in Perspective, S., SIGMOD Record, vol. 27, Issue 2, Jun. 1998, pp. 516-519.
Soreide, et al., "Mosaic Access to Realtime Data from the TOGA-TAO array of moored buoys", accessed from web site Equatorial Pacific, Oct. 16, 2002, pp. 1-8.
Northwest Fisheries Science Center, National Marine Fisheries Service (NOAA), "Water Recirculation Project", accessed from web site NWFSC:Aquaculture-Water Recirculation Project, Oct. 16, 2002, pp. 1-3.
Northwest Fisheries Science Center, "NWFSC Water Recirculation Project: Data Acquisition and Web Display", accessed from web site NWFSC Web Template, Oct. 16, 2002, pp. 1-3.
Scott, et al., "A Computer Automated Cold Water Recirculating System for Aquaculture Research", accessed from web U.S. Dept. Commerce/NOAA/NMFS/NWFSC, Oct. 16, 2002, pp. 1-9.
Remote Measurement Systems, "Case Studies", accessed from web site Remote Measurement Systems—Case Studies: Fisheries, Oct. 16, 2002, pp. 1-4.
Remote Measurement Systems, "Posting Real-Time Measurement to the Web", Home Energy, accessed from web site Posting Real-Time Measurements to Web Pages, Oct. 16, 2002, pp. 1-5.
Buhrer, Thomas, "Neutral-Carrier-Based Ion-Selective Microelectrodes Design and Application, A Review", Department of Organic Chemistry, Swiss Federal Institute of Technology, Zurich, Switzerland, Analytical Sciences, Dec. 1988, vol. 4, pp. 547-557.
Tu et al., "Nanoelectrode Arrays Based on Low Site Density Aligned Carbon Nanotubes", Nano Letters, 2003, vol. 3, No. 1, pp. 107-109.
Ren et al., "Synthesis of Large Arrays of Well-Aligned Carbon Nanotubes on Glass", Nov. 6, 1998, vol. 282 from www.sciencemag.org, pp. 1105-1107.
Lumb Alan M. et al., "Users Manual for an Expert System (HSPEXP) for Calibration of the Hydrological Simulation Program—Fortran", U.S. Geological Survey, Water-Resources Investigations Report 94-4168, 1994, 106 pages.
Johnston et al., "Management, Operation and Maintenance of Irrigation and Drainage Systems", Second Edition, ASCE Manuals and Reports on Engineering Practice No. 57, American Society of Civil Engineers, 1991, 13 pages.
Final Rejection dated Jul. 19, 2013, in U.S. Appl. No. 13/619,880.
Notice of Allowance dated Aug. 7, 2013, in U.S. Appl. No. 13/619,775.
Nonfinal Office Action dated Sep. 12, 2013, in U.S. Appl. No. 12/565,091.
Final Rejection dated Sep. 13, 2013, in U.S. Appl. No. 12/952,566.
Nonfinal Office Action dated Sep. 13, 2013, in U.S. Appl. No. 11/331,721.
Nonfinal Office Action dated Nov. 19, 2013, in U.S. Appl. No. 13/619,880.
Nonfinal Office Action dated Jan. 16, 2014, in U.S. Appl. No. 13/620,000.
European Office Action dated Sep. 30, 2014, in European Application No. 03 815 260.9—1959.
Bohme, Thomas J. et al., "Comparison of Autoassociative Neural Networks and Kohonen Maps for Signal Failure Detection and Reconstruction", Jan. 1, 1999 XP055050318, Retrieved from the Internet: URL:http//citeseerx.ist.psu.edu/viewdoc/download-?doi=10.1.1.39,4334&rep=rep1&type=pdf [retrieved on Jan. 18, 2013]
Lindqust M. et al., "Virtual water quality tests with an electronic tongue", IMTC 2001, Proceedings of the $18^{th}$, IEEE I Nstrumentation and Measurement Technology Conference, Budapest, Hungary, May 21-23, 2001; [IEEE Instrumentation and Measurement Technology Conference. (IMTC):] New York, NY: IEEE, US, vol, 2, May 21, 2001, pp. 1320-1324, XP010545970, DOI: 10.1109/IMTC.2001.928288 ISBN: 978-0/7803-6646-6.
Bourgeois W., et al.: "Use of a chemical sensor array for detecting pollutants in domestic wastewater", Water Research, Elsevier, Amsterdam, NL, vol. 36, No. 18, Nov. 1, 2002, pp. 4505-4512, XP004380734, vol. 36, No. 18, Nov. 1, 2002, pp. 4505-4512, XP004380734, ISSN: 0043-1354, DOI: 10.1016/S0043(02)00183-5.

\* cited by examiner

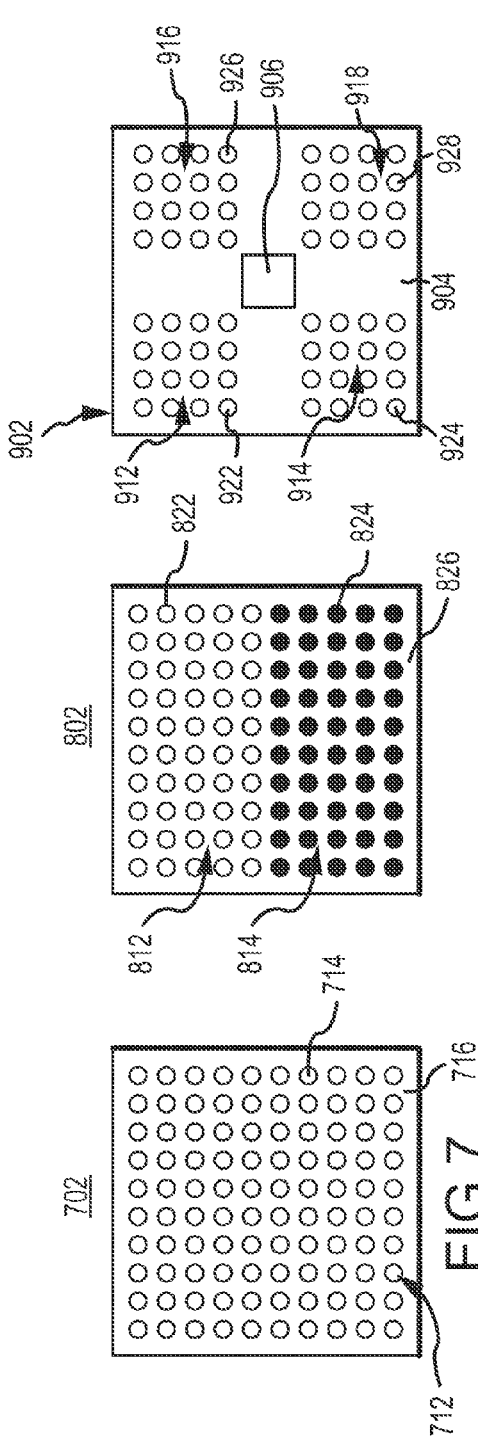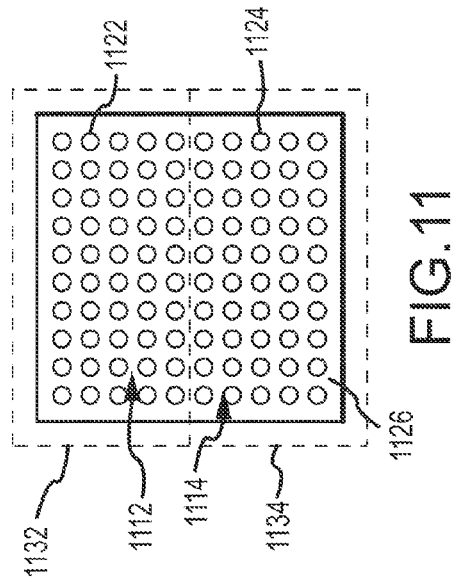

TABLE 1
| WATER ANALYSIS METHOD | FUNTIONALIZATION (R=CNT) |
|---|---|
| ph | VINLY-FERROCENE AND FERROCENE CARBOXELDEHYDE |
| CHLORINE | 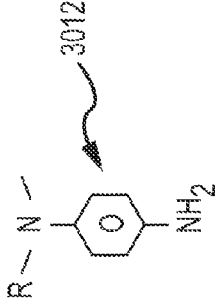 3012 |
| FLUORIDE | 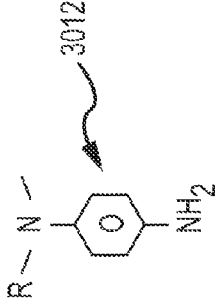 3014 |
FIG. 30

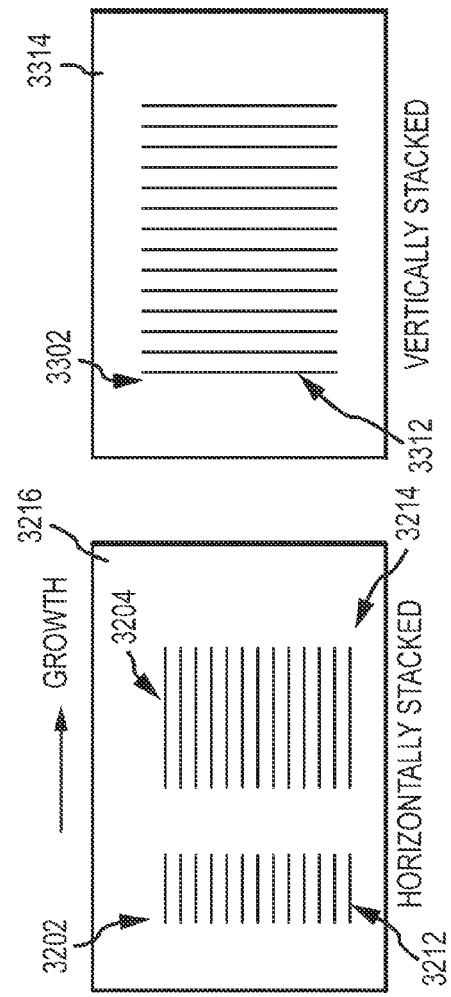
FIG.33
FIG.32
FIG.31
FIG.35
FIG.34

CARBON NANOTUBE SENSOR

CROSS-REFERENCE TO RELATED APPLICATIONS

This application makes reference to the following applications and patents that describe technology that may be used with embodiments of the present invention: U.S. patent application Ser. No. 12/710,451, filed Feb. 23, 2010, U.S. Pat. No. 7,698,073, U.S. Pat. No. 7,454,295, U.S. Pat. No. 6,560,543, U.S. Pat. No. 6,332,110, U.S. patent application Ser. No. 12/565,091 filed Sep. 23, 2009, U.S. patent application Ser. No. 11/331,721 filed Jan. 13, 2006; U.S. patent application Ser. No. 12/272,018 filed Nov. 17, 2008, U.S. Pat. No. 6,954,701, and U.S. patent application Ser. No. 10/392,112 filed Mar. 19, 2003. The entire contents and disclosures of each of the above applications/patents are incorporated herein by reference.

FIELD OF THE INVENTION

The present invention relates to the field of fluid treatment and safety, and in some embodiments, to a method and system of carbon nanotube sensors enabling direct and/or remote monitoring and/or storage of fluid treatment and safety data.

BACKGROUND

It is well recognized that many aspects of manufacturing, as well as life itself, is dependent upon water. Water may be characterized by the amount of cations and anions, metals, turbidity, dissolved solids, and so forth, all of which combine to form unique water chemistries. Technology provides the ability to adjust, reduce, or remove such qualities to effectively prepare water for use in a particular application. Proper water treatment systems provide an economical way of conditioning water to a predetermined quality level as required for the particular application. Protection of water supplies from system or equipment failure as well as inadvertent or deliberate contamination are important concerns. While devices and methods exist to analyze water for contaminants, widespread deployment of such devices is expensive and difficult.

SUMMARY

According to a first broad aspect of the present invention, there is provided a remote monitoring system, comprising: one or more sensors located within a water treatment system being monitored, a remote computer disposed at a first distant location from the water treatment system, and an analyzer for manipulating data obtained from the one or more sensors of the water treatment system, wherein the one or more sensors comprise one or more carbon nanotube sensors, wherein the data is transmitted from the water treatment system to the remote computer using a mode of transmission, and wherein the remote computer generates an output from the manipulated data.

According to a second broad aspect of the present invention, there is provided a method for monitoring a water treatment system comprising the following steps: (a) transmitting data collected from one or more sensors in the water treatment system to a remote computer disposed at a first distant location from the water treatment system, and (b) generating an output based on the data, wherein the data is transmitted from the water treatment system to the remote computer using a mode of transmission, wherein the one or more sensors comprise one or more carbon nanotube sensors.

According to a third broad aspect of the present invention, an electrochemical sensing apparatus comprising: a electrode body including one or more pressure sensors, and one or more temperature sensors, and one or more counter electrodes, and one or more working electrodes, wherein each working electrode of the one or more working electrodes comprises an array of one or more carbon nanotubes.

According to a fourth broad aspect of the present invention, there is provided a device comprising: a sensor device one or more working electrodes, each working electrode of the one or more working electrodes comprising: a substrate, and an array of carbon nanotubes bound to the substrate, wherein each carbon nanotube of the array of carbon nanotubes is bound at one end to the substrate, wherein the array of carbon nanotubes comprises two or more rows of carbon nanotubes, and wherein first carbon nanotubes of a first row of the two or more rows of carbon nanotubes each have a first functionality, wherein second carbon nanotubes of a second row of the two or more rows of carbon nanotubes each have a second functionality, and wherein the first functionality is different from the second functionality.

According to a fifth broad aspect of the present invention, there is provided a device comprising: a sensor device comprising a working electrode assembly comprising one or more working electrodes, each working electrode of the one or more working electrodes comprising: a substrate, and an array of carbon nanotubes bound to the substrate, wherein each carbon nanotube of the array of carbon nanotubes is bound at one end to the substrate, and wherein each of the working electrodes of the one or more working electrodes senses an analyte when exposed to an water solution comprising one or more analytes.

According to a sixth broad aspect of the present invention, there is provided a device comprising, a working electrode assembly comprising one or more working electrodes, wherein each working electrode of the one or more working electrodes comprises: a substrate, and an array of carbon nanotubes bound to the substrate, wherein each carbon nanotube of the array of carbon nanotubes is bound at one end to the substrate, and wherein each of the working electrodes of the one or more working electrodes senses an analyte when exposed to an water solution comprising one or more analytes.

According to a seventh broad aspect of the present invention, there is provided a device comprising, one or more working electrodes mounted on the substrate, a respective drive electrode for altering the environment surrounding each one of the one or more working electrodes, wherein each working electrode of the one or more working electrodes and each respective drive electrode comprises an array of carbon nanotubes bound to the substrate, wherein each carbon nanotube of each array of carbon nanotubes is bound at one end to the substrate, and wherein each of the working electrodes of the one or more working electrodes senses an analyte when exposed to an water solution comprising one or more analytes.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

FIG. 7 is a top plan view in simplified form of a working electrode comprising an array of nanotubes in accordance with one embodiment of the present invention.

FIG. 8 is a top plan view in simplified form of a working electrode comprising two arrays of nanotubes in accordance with one embodiment of the present invention.

FIG. 9 is a top plan view in simplified form of a working electrode comprising four arrays of nanotubes and counter electrode in accordance with one embodiment of the present invention.

FIG. 10 is a top plan view in simplified form of a working electrode comprising nine arrays of nanotubes in accordance with one embodiment of the present invention.

FIG. 11 is a top plan view in simplified form of a working electrode comprising two arrays of nanotubes in accordance with one embodiment of the present invention.

FIG. 30 is a table showing functional groups that may be bound to carbon nanotubes to functionalize the carbon nanotube in accordance with one embodiment of the present invention.

FIG. 31 is a top plan view in simplified form of an array of carbon nanotubes in a random configuration in accordance with one embodiment of the present invention.

FIG. 32 is a top plan view in simplified form of an array of carbon nanotubes in horizontally stacked configuration in accordance with one embodiment of the present invention.

FIG. 33 is a top plan view in simplified form of a array of carbon nanotubes in vertically stacked configuration in accordance with one embodiment of the present invention.

FIG. 34 is a perspective view of an open end of a carbon nanotube in accordance with one embodiment of the present invention.

FIG. 35 is a perspective view of an open end of a carbon nanotube in accordance with one embodiment of the present invention.

DETAILED DESCRIPTION

Definitions

Figure 1:
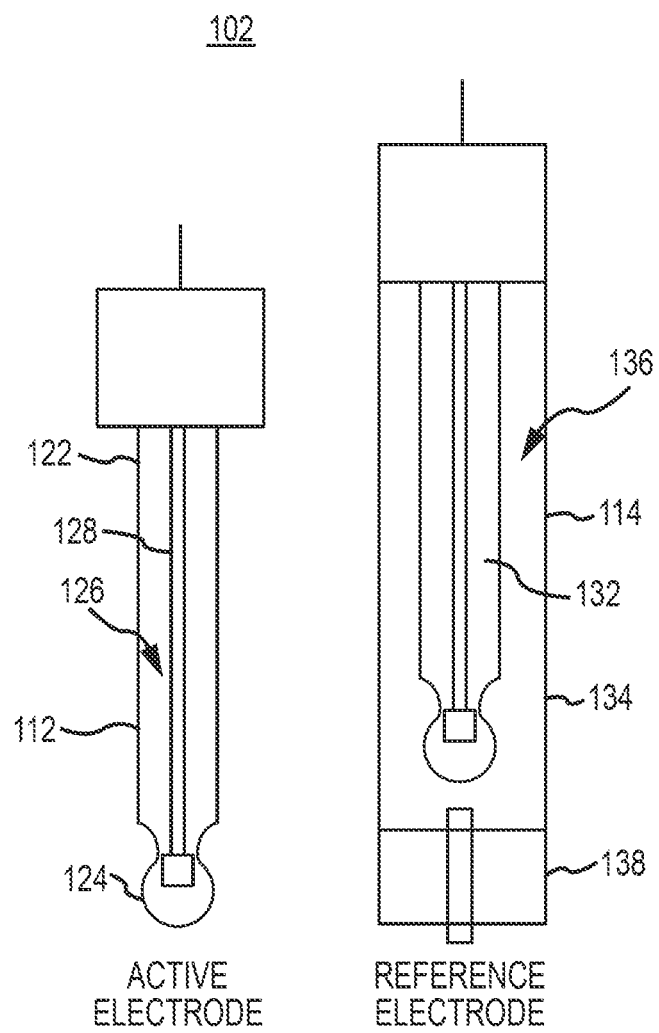
FIG. 1 is an illustration in simplified form of a prior art active electrode (working electrode) and a prior art reference electrode.

Where the definition of terms departs from the commonly used meaning of the term, applicant intends to utilize the definitions provided below, unless specifically indicated.

For purposes of the present invention, it should be noted that the singular forms, "a", "an", and "the" include reference to the plural unless the context as herein presented clearly indicates otherwise.

For purposes of the present invention, directional terms such as "top", "bottom", "upper", "lower", "above", "below", "left", "right", "horizontal", "vertical", "up", "down", etc. are merely used for convenience in describing the various embodiments of the present invention. The embodiments of the present invention may be oriented in various ways. For example, the diagrams, apparatuses, etc. shown in the drawing figures may be flipped over, rotated by 90° in any direction, reversed, etc. For example, rows and/or columns may be oriented in any direction.

For purposes of the present invention, a value or property is "based" on a particular value, property, the satisfaction of a condition, or other factor, if that value is derived by performing a mathematical calculation or logical decision using that value, property or other factor.

For purposes of the present invention, the term "analysis report" refers to any organized presentation of data, raw data or historical data, manipulated data, observational data, information, analysis result, etc., based on data obtained or collected from one or more sensors that is generated or manipulated by an analyzer on the remote computer of the present remote monitoring system. An analysis report may be prepared for any intended recipient, such as an elected official, manager or operator of a water treatment system, customer, member of the public, etc. According to some embodiments, an "analysis report" may be a submission to a regulatory and/or law enforcement agency in any required format.

For purposes of the present invention, the term "analysis result" refers to any information, value, relationship, product, etc., created by aggregation, calculation, algorithm, analysis, manipulation, etc., of data or information obtained or collected from one or more sensors as performed by an analyzer on the local computer and/or the remote computer of the present remote monitoring system. For example, an "analysis result" may include observational data analyzed, manipulated, etc., by a local computer.

For purposes of the present invention, the term "analyzer" refers to a portion of the local computer or the remote computer of the present remote monitoring system which may be stored on the local computer and/or the remote computer, such as a software program(s) or other routine(s), firmware, and/or hardware, which may analyze, manipulate, etc., data, raw data, observational data, historical data, or any other information obtained from one or more sensors. When the local computer is a logger device, the "analyzer" may be located on the logger device.

For purposes of the present invention, the term "carbon nanotube (CNT)", unless specified otherwise, refers to any type of carbon nanotube. CNTs typically exist as single layers or multiple layers of cylindrical layers of graphen sheets. The individual sheets can vary in layering, and functionality. For example, CNTs can exist as single-walled CNTs (SWCNT), and multi-walled CNTs (MWCNT). Further, the CNTs can be conductive, semi-conductive, or insulated. CNTs can also be chiral or achiral. CNTs can be manufactured in various different forms. In addition to arrays of CNTs that are attached that are each attached at one end to a substrate and arranged in regular columns and/or rows, arrays of CNTs may be random (see FIG. 31), horizontally stacked (see FIG. 32) or vertically stacked (see FIG. 33). The CNTs of an array may chiral, achiral, open headed (see FIG. 34), capped (see FIG. 35), budded, coated, uncoated, functionalized, neat, anchored, unanchored, basal plane, edge plan, step, or any other known configuration.

For purposes of the present invention, the term "counter electrode" or "auxiliary electrode" refers to an electrode that provides a circuit with the working electrode over which current is either applied or measured.

For purposes of the present invention, the term "data" refers to any information, reading, measurement, value, etc., ultimately obtained from one or more sensors or derived from such data. The term "data" includes any data or information including raw data obtained directly from one or more sensors without manipulation, historical data earlier obtained from one or more sensors or entered or derived from data obtained at an earlier point or period in time, and analyzed or manipulated data, such as data or information manipulated, analyzed, etc., by an analyzer. The term "data" may include, for example, an analysis result or observational data.

For purposes of the present invention, the term "database" refers to a device or apparatus of the present remote monitoring system used to store data, raw data, historical data, manipulated data and/or information in a logical or ordered arrangement or configuration. The database may be part of the remote computer or separate, albeit connected to or in communication with, the remote computer.

For purposes of the present invention, the term "distant" in reference to a remote computer and/or remote database refers to the remote computer and/or remote database being physically separated from a water treatment system. The term "distant" may refer to the remote computer and/or remote database being located away from the premises of a water treatment system and/or a water treatment core facility. The term "distant" may refer to a remote computer and/or remote database that is only connected or linked to a water treatment system (or only connected or linked to the one or more sensors, electronic control system, and/or local computer located within the water treatment system) via a mode of transmission.

For purposes of the present invention, the term "electronic control system" refers to a portion of a water treatment system that may control the operation of equipment and operation of a water treatment system. According to some embodiments, a remote computer of the present invention may access or collect data from one or more sensors via an electronic control system. An electronic control system may include an in-house Supervisory Control and Data Acquisition System (SCADA) or a Progammable Logic Controller (PLC).

For purposes of the present invention, the term "functionalized carbon nanotube" or "functionalized CNT" refers to a carbon nanotube to which has been bound a substituent. A CNT may be functionalized by an organic, organometallic or inorganic substituent. For example, a CNT may be modified by any organic ($SN_2$ for example) or inorganic (salt) reaction.

For purposes of the present invention, the term "functionality" refers to the presence or absence of one or more substituents bound, complexed or otherwise associated with a carbon nanotube. Two or more carbon nanotubes have different functionalities if the substituent or groups bound to the two or more carbon nanotube are different. For example, a first carbon nanotube to which is bound a first substituent, a second carbon nanotube to which is bound a second substituent and a third carbon nanotube to which no substituent is bound would all have different functionalities. Also, a first carbon nanotube to which is bound a first substituent and a second carbon nanotube to which is bound both a second substituent and the first substituent would have different functionalities.

For purposes of the present invention, the term "hardware and/or software" refers to functions that may be performed by digital software, digital hardware, or a combination of both digital hardware and digital software.

For purposes of the present invention, the term "local computer" refers to any type of computer, processor, or device physically located at or near a water treatment system (i.e., not remotely located) and connected to the one or more sensors either directly or indirectly. The local computer may assemble, collect, aggregate, manipulate, or analyze data from one or more sensors of the present remote monitoring system prior to the data being transmitted to the remote computer of the present remote monitoring system. The "local computer" may be any computer, etc. able to (1) at least temporarily store, assemble, collect, aggregate, etc., data from one or more sensors and (2) transmit data or information to a remote computer (or a remote database associated with the remote computer) via a mode of transmission. Thus, a "local computer" may contain or include (1) a memory device(s) to store, assemble, collect, aggregate, etc., the data at least temporarily, (2) one or more ports or inputs for receiving data or information either directly or indirectly from one or more sensors, and (3) a transmission interface(s) to transmit data or information to a remote computer. A "local computer" may further have the ability to process, manipulate, analyze, etc., the data obtained from the one or more sensors, such as by an analyzer or software located on local computer, prior to transmission of data or information to the remote computer and/or remote database. The "local computer" may be a logger device as described herein.

For purposes of the present invention, the term "mode of communication" refers to any suitable technology for sending, uploading, or communicating an output, including data, information, analysis results, analysis reports, alerts, alarms, etc., from a remote computer to a remote viewing device of the present remote monitoring system. The mode of communication may include any of the technologies used for the mode of transmission. For example, according to some embodiments, a suitable technology to serve as a "mode of communication" may be the Internet or world wide web. In such a case, the output may be uploaded onto an Internet server computer, which may be the remote computer of the present remote monitoring system or the Internet server computer may be separate from the remote computer. According to other embodiments, the "mode of communication" for sending an output to, or allowing access to an output by, a remote viewing device, includes, but is not limited to any wired or wireless connections as well as any protocols: the Internet; TCP/IP; MODBUS RTU, MODBUS ASCII, and MODBUS TCP; XML; Ethernet; file transfer protocol (FTP); Bluetooth®; ZigBee®; email, such as SMTP; cellular phone networks, such as CDMA and TDMA; radio signals or remote terminal units (RTU) coupled to radio frequency transmitters; cellular modem; SDI-12; satellite transmission; existing telephone or communication networks or wiring, a standard Public Switched Telephone Network (PSTN); a wireless network; a wide area network (WAN); wireless local area network (WLAN); local area network (LAN); or metropolitan area network (MAN); a cable internet connection; short message system (SMS); dial-up modem; a point to point link; global system for mobile communications (GSM, 3GSM), general packet radio services (GPRS), evolution-data optimized (EV-DO), enhanced data rates for GSM evolution (EDGE), digital enhanced cordless telecommunications (DECT), integrated digital enhanced network (iDEN), universal mobile telecommunications systems (UMTS), advanced mobile phone systems (AMPS); or any other suitable means known to those skilled in the art to send, upload, or communicate an output to a remote viewing device.

For purposes of the present invention, the term "mode of transmission" refers to any suitable technology or device known and available in the art for transmitting data and information to a remote computer of the present remote monitoring system. The data and information may be transmitted by the mode of transmission either directly from the one or more sensors, from an electronic control system, or from a local computer connected to the electronic control system and/or one or more sensors, which may each utilize a transmission interface. The mode of transmission may include any of the technologies used for the mode of communication. Examples of modes of transmission may be achieved or carried out through any suitable medium, such as any wired or wireless connections as well as any protocols, including, but not limited to: the Internet; TCP/IP; MODBUS RTU, MODBUS ASCII, and MODBUS TCP; XML; Ethernet; file transfer protocol (FTP); email, such as SMTP; cellular modem; Bluetooth®; ZigBee®; cellular phone networks, such as CDMA and TDMA; radio signals or remote terminal units (RTU) coupled to radio frequency transmitters; satellite transmission; SDI-12; existing telephone or communication networks or wiring, a standard Public Switched Telephone Network (PSTN); dial-up using landline or telephone; a wireless network, such as wi-fi; a wide area network (WAN); wireless local area network (WLAN); local area network (LAN); or metropolitan area network (MAN); a cable internet connection; short message system (SMS); dial-up modem; a point to point link; global system for mobile communications (GSM, 3GSM), general packet radio services (GPRS), evolution-data optimized (EV-DO), enhanced data rates for GSM evolution (EDGE), digital enhanced cordless telecommunications (DECT), integrated digital enhanced network (iDEN), universal mobile telecommunications systems (UMTS), advanced mobile phone systems (AMPS) or any other suitable means to transmit data to a remote computer known to those skilled in the art. The exact mode of transmission may vary depending on the circumstances. According to embodiments of the present invention, the mode of transmission may transmit data or information continuously, in real time, at periodic or selected intervals, on condition, or on demand by a user.

For purposes of the present invention, the term "observational data" refers to data or information that has been analyzed, manipulated, etc., by the local computer, such as by an analyzer on the local computer, from raw data or information obtained from one or more sensors prior to being transmitted to a remote computer and/or remote database.

For purposes of the present invention, the term "output" refers to any product, publication, submission, uploaded content, etc., including any information, data, analysis result, analysis report, etc., that may be communicated from the remote computer of the present remote monitoring system to a remote viewing device in a format suitable for display by the remote viewing device to a user.

For purposes of the present invention, the term "remote computer" refers to an electronic device of the present remote monitoring system that is capable of storing, processing, and/or manipulating data, raw data or historical data, such as a computer, server, etc., that is physically separated, i.e., at a remote or distant location, from the location of the water treatment system monitored by such system. For example, a "remote computer" may include a web or Internet server. The "remote computer" may further include a database and/or an analyzer.

For purposes of the present invention, the term "remote database" refers to a device or apparatus of the present remote monitoring system used to store data, raw data, historical data, manipulated data and/or information, such as in a logical or ordered arrangement or configuration. The remote database may be part of the remote computer or separate, albeit connected to or in communication with, the remote computer. As such, the "remote database" is physically separated, i.e., at a remote or distant location, from the location of the water treatment system.

For purposes of the present invention, the term "remote monitoring system" refers to a system for remotely monitoring the operation and equipment of a non co-located water treatment system or the water quality in, toward, or from a non-collocated water treatment system using sensors to collect data that is transmitted to a remote computer for analysis, manipulation, and communication to a remote viewing device for a user.

For purposes of the present invention, the term "remote viewing device" refers to any device or apparatus known in the art that may be used to view an output of the present remote monitoring system from the remote computer, such as, for example, personal computers or terminals, servers, etc., as well as a variety of handheld personal communications equipment, such as cell phones, pagers, PDA's, Blackberrys®, Palm® devices, iPhones®, etc.

For purposes of the present invention, the term "sensor" refers to a device, probe, or apparatus for the detection or measurement of parameters or values relevant to water quality or the operation of a water treatment system. The term "sensor" may refer to a device, probe, or apparatus connected to a local computer, such as a logger device.

For purposes of the present invention, the term "transmission interface" refers to a portion of a local computer, electronic control system, and/or one or more sensors of a remote monitoring system that is able of transmitting data or information to a remote computer via any suitable mode of transmission.

For purposes of the present invention, the terms "treat," "treated," "treating," "treatment," and the like shall refer to any process, treatment, generation, production, discharge, or other operation that may be performed by a water treatment system on, or in relation to, the water in the water treatment system.

For purposes of the present invention, the term "user" refers to a person, entity, or agency that views data, information, analysis results, or analysis reports communicated from the remote computer to the remote viewing device of the present remote monitoring system.

For purposes of the present invention, the term "water treatment system" refers to any system designed or used to process, treat, or generate water or a water-based product for a particular application. A "water treatment system" may be used to generate water having a predetermined, desired, or preferred set of characteristics, qualities, or properties, such as purity, etc. For example, a "water treatment system" may include a water treatment facility for generating and distributing potable drinking water for the public, a system designed to generate water for a manufacturing process, etc. In the case of a water treatment facility for generating potable drinking water, the water treatment system may further include a distribution system for distributing the potable drinking water to the public. A "water treatment system" may also be any system used to process or treat a water-based substance into a product that may be discharged into the environment, such as, for example, a central wastewater treatment plant (WWTP), etc. In the case of a WWTP, the water treatment system may further include a collection system for collecting waste water and funneling it into the central WWTP. Water treatment systems may include public or municipal systems or private systems dedicated to an industry, factory, or particular real estate development. For example, a water treatment system may include any system, plant, or facility that uses equipment based on advanced separation, filtration, dialysis, ion exchange processes, or any other basis, technology, or mechanism for processing, treating, detecting, purifying, isolating, separating, etc., water according to relevant parameters.

For purposes of the present invention, the term "water treatment core facility" refers to a central facility that processes, treats, generates, etc., water in contrast to a broader collection or distribution system, such as a central wastewater treatment plant (WWTP), for the processing or treatment of waste water, or a water treatment facility, such as a facility for the generation of potable drinking water.

For purposes of the present invention, the term "water" refers to water or any fluid that may be processed, treated, generated, produced, discharged, etc., by a water treatment system. For example, the term "water" may refer to water being treated or processed by a water treatment facility for the distribution of potable drinking water to the public, or the term "water" may refer to sewage or waste water processed or treated by a central wastewater treatment plant (WWTP). Thus, "water" may include any number of solutes, sediments, suspensions, organic matter, etc., as the case may be.

For purposes of the present invention, the term "working electrode" or "active electrode" refers to the electrode of a water monitoring system at which a reaction of interest occurs.

Description

Many processes and applications for protecting water supplies require the use of water having sufficiently low or absent levels of contaminants or harmful substances, and thus rely on the use of water treatment systems to ensure adequate levels of water purity, quality, and/or safety. These water treatment systems may generally use techniques, such as advanced separation, filtration, reverse osmosis, and/or ion exchange processes, as well as the introduction of materials or disinfectants to achieve the desired water quality. However, equipment failure or tampering of these systems may result in poor or unsafe water quality for a given application. Therefore, it is critical that any water treatment system used to purify or treat water for any such applications is adequately monitored to ensure that the desired levels of water purity, quality, and/or safety are met. One application in which water quality is important is in providing potable drinking water to the public. Most water treatment systems for the production and distribution of drinking water to the public rely, for example, on the introduction and maintenance of materials, such as disinfectants, into the water system to protect against biological or chemical contamination. Chlorine, in the form of gas or hypochlorite or hypochlorous acid, is one of the most common materials used for this purpose. Substitutes such as chloramines, ozone, hydrogen peroxide, peracetic acid, chlorine dioxide, and various mixed oxides are also used. Many of these materials have a more or less common mode of action. They rely on some sort of oxidation to effect the deactivation of biological organisms and the destruction of other organic compounds present in the water to be treated. The reaction rates of the various materials, such as disinfectant compounds, are reasonably well known and well characterized. However, excessive amounts of these materials may cause problems on their own. Thus, it is important that adequate monitoring is performed to ensure that sufficient but not excessive amounts of these materials or disinfectants are maintained in a water treatment system.

Water treatment systems, and monitoring systems, often include sensors that measure the concentration of ions in the solution. The solution can be aqueous or organic in nature. One commonly monitored ion is the hydronium ion, however, any cation or anion can be of importance to a water treatment or monitoring system.

Water treatment systems, and most chemical reactions in general, are highly influenced by the concentration of hydronium ions ($H_3O^+$, or $H^+$), or pH, of the reaction environment. The pH of a solution is also often referred to as the acidity of the fluid being tested. By definition pH=$-\log [H_3O^+]$ or the negative log of the molar concentration of hydronium ions. On the pH scale, a very acidic solution has a low pH value, such as zero or one, corresponding to a large concentration of hydrogen ions ($H^+$). In contrast, a very basic solution has a high pH value, corresponding to a very small number of hydrogen ions (or to a correspondingly large number of $OH^-$ ions). A neutral solution, such as substantially pure water, has a pH value of about seven.

The presence of the correct concentration of Acid in a solution can induce many forms of catalysis, such as, but not limited to, acetal formation, acetal hydrolysis, dehydration of alcohols, amide hydrolysis, epoxide ring opening, ester hydrolysis, esterification, ether formation, and glycoside formation. The correct pH concentration can also include catalysis of hydration including, but not limited to, alkenes, alkynes, nitriles, nucleophilic acyl substitution, nucleophilic addition to aldehydes and ketones.

The pH of potable drinking water in many governments is a required reporting parameter and effluent water pH ranges are strictly controlled. For example, in the United States the Environmental Protection Agency sets specific ranges for potable water discharge, if the water pH is outside the range is can be unsafe for human and animal consumption.

Municipal drinking water may be obtained from a variety of sources, which can be made potable by use of proper water treatment equipment. For example, a reverse osmosis system may be used to lower the total dissolved solids from sea water with minimal pretreatment to produce potable drinking water. Despite the sophistication of pretreatment of seawater, improper monitoring or operation can allow the seawater to quickly foul membranes. If fouling occurs, but is found quickly, the membranes may be cleaned, and water contamination and associated water treatment repairs may be averted. However, if the fouling is not detected quickly through proper monitoring, the membranes can be irreparably damaged, and expensive partial or total membrane replacement would be required. The cost of unplanned membrane replacement, not including the lost revenues typically associated with down time, can make such a system cost prohibitive.

Another application in which water quality is important is with Waste Water Treatment Plants (WWTP). The treatment and subsequent recycling of wastewater is a cornerstone of the quality of life in the industrialized world. Cities, industries, and agricultural operations produce large quantities of wastewater, all of which must be treated to some degree to remove contaminants or pollutants before the water is suitable for recycling or discharge into the environment, such as streams, rivers or oceans. In metropolitan areas, central waste water treatment plants must treat water from a variety of sources including city, industrial, and agricultural waste water. In many cases, generators of industrial waste water are required to install and operate waste water treatment plants at their own sites before discharge into central water collection systems. At the central water collection system, industrial wastes may generally be mixed with domestic or city waste water and other untreated waste sources. These mixed wastes are then transported to the central waste water plant or sewage treatment facility for final treatment before discharge.

Increasingly, the need for pure water is causing more and more municipalities to install waste water recovery processes to recycle municipal WWTP effluents back into water of suitable quality to be used for potable drinking water or irrigation. For example, such recovery processes may recover secondary treated municipal effluents using reverse osmosis, which may then be injected back into an aquifer. More and more of these installations are planned throughout the United States and the rest of the world.

One difficult aspect of treating municipal waste water effluent is that neither the flow rates nor the mix of contaminants are constant. This is particularly true for a municipal WWTP with collection systems that include a variety of industrial discharge sources in addition to the usual sanitary discharges from homes, businesses, schools, and so on. While the sanitary discharges are well characterized in terms of composition and treatability, the addition of industrial wastes means that the WWTP must plan for a wide variety of contaminants. In general, most WWTP systems cannot deal effectively with every situation. Even with excellent design and engineering, the large fluctuation in the type and quantity of contaminants reaching the WWTP often results in varying levels of effective treatment in the discharge from the WWTP. For a tertiary water recovery plant treating the effluent from the WWTP this can be particularly difficult since many contaminants are not readily removed even by processes such as reverse osmosis. In addition, certain contaminants can also foul reverse osmosis, ultrafiltration, and microfiltration membranes, causing loss of performance or membrane damage. Therefore, it is important that WWTPs are monitored to ensure that contaminants are properly removed before discharge or reuse back into the environment and to avoid damage to expensive equipment.

Water is also required for steam generation in nuclear reactors. The boilers of these nuclear reactors operate at extremely high temperatures that require a very high quality of water. It is critical that the process system is monitored properly to avoid expensive boiler cleanings and the associated down time. Such systems may also include the need to monitor hazardous boiler chemicals, such as hydrazine, requiring highly qualified personnel. These examples highlight the importance of monitoring the operation of water treatment systems to not only ensure sufficient water quality, but also to avert costly equipment repair or replacement.

Water quality is also important for many manufacturing processes. For example, the manufacturing of semiconductors requires an ultra-pure water quality. Again, it is critical that the water treatment system is monitored properly to avoid latent defects in the manufacturing of products, such as semiconductors.

As yet another example, monitoring water quality is also important to avoid or lessen the consequences of equipment failure or deliberate tampering, such as by terrorist act, in contaminating the water supply. Adequate monitoring may help to catch any such contamination of the water supply to avoid harm and ensure that appropriate action is taken.

Many forms of electrochemical sensors exist today to detect the presence and concentration of ions in water. One such common electrochemical sensor is for the measurement of pH. FIG. 1 shows a portion of a prior art pH meter probe 102 including working electrode 112 and a reference electrode 114. Working electrode 112 comprises a glass tube 122 with an ion sensitive glass bulb 124 at one end. Glass tube 122 contains an electrolyte 126 and an electrode 128. The glass on the exterior of ion sensitive bulb 124 exchanges ions with the fluid to be tested (not shown in FIG. 1). This produces a charge in a hydrated layer on the outside of the bulb. The internal electrolyte interacts with the ion sensitive glass and reflects the potential developed by the ions at the outside of the glass. Reference electrode 114 comprises an electrode 132, similar to working electrode 112, mounted a separate chamber 134 and solution 136, and is also in ionic communication with the fluid being tested through an ionic bridge 138. A voltage potential between working electrode 112 and reference electrode 114 is thereby formed, similar to a battery. The voltage potential that is developed between working electrode 112 and a reference electrode 114 is directly related to the ion concentration of the solution. The reference electrode 114 provides a stable potential against which working electrode 112 can be compared.

The voltage potential can be processed according to a table, formula, or other algorithm to arrive at an ionic concentration measurement, such as a pH value, for example. An ionic circuit is formed between the working electrode and a ground electrode, creating a measurable voltage potential. The reference potential is a known, substantially constant amount against which the process voltage (i.e., a voltage measurement) can be compared and interpreted by a prior art pH meter. The voltage potential between the working electrode and the reference electrode can be processed to determine an ionic concentration in the external test fluid. The accuracy of ionic and/or pH measurements can be affected by various factors, including temperature and/or contaminated electrolyte solutions, for example. A common source of inaccuracy can be an improper or inaccurate reference signal generated from a reference electrode. If the reference signal is inaccurate, the resulting pH or ion measurement will be affected. Consequently, it is of great importance that a proper and accurate reference value be obtained.

The ionic bridge of the reference electrode, such as a salt bridge, enables ionic communication between the reference electrode and the external test fluid. However, the ionic bridge may allow some fluid exchange, enabling contamination of the internal buffer solution and possible poisoning of the internal reference electrode, and enabling contamination of the fluid to be measured. A major problem with pH probes is in the junction between the internal fill solution of the reference electrode assembly and the external test fluid. Clogging or failure of the junction usually leads to very slow or erroneous readings. The junction can also allow the contamination of the fill solution with the measurement medium. This can degrade the reference electrode which then renders the pH probe inaccurate and it usually has to be replaced.

One prior art solution has been the employment of multiple junctions and chambers between the reference electrode and the exterior medium. Another prior art solution has used flowing junctions in which a continuous supply of fill solution is fed to the reference electrode compartment and exits via a small hole or conduit. This has the advantage of preventing the contamination of the fill solution and the reference electrode but has the disadvantage of cumbersome plumbing to the electrode and the necessity to send the measurement medium to waste as it is contaminated with fill solution.

Figure 2:
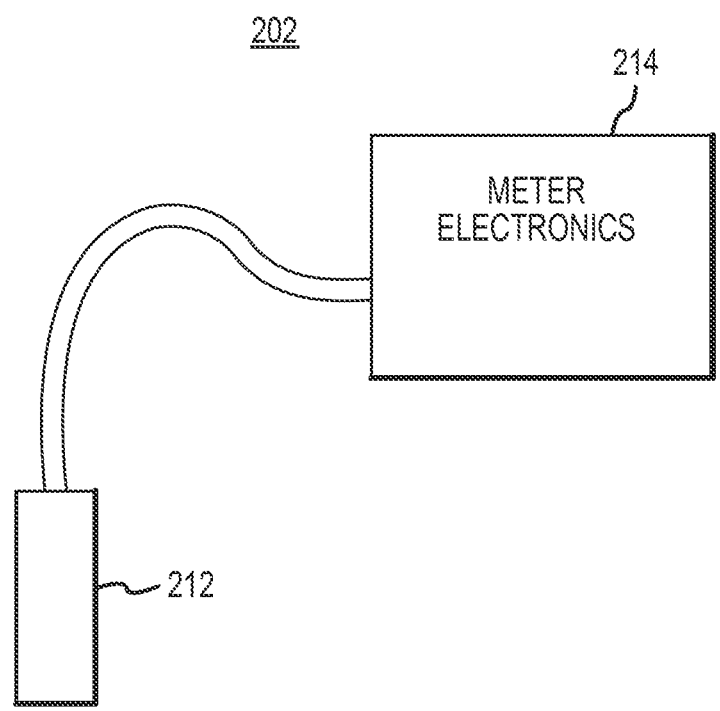
FIG. 2 is an illustration in schematic form of a single electrode/sensor pH meter.

A newer approach has been to enclose both the working electrode and the reference electrode within an impermeable chamber, such as a glass chamber, for example. This is shown in U.S. Pat. No. 4,650,562 to Harman, which is incorporated herein by reference. The reference electrode in Harman interfaces with the external test fluid through a pH sensitive glass bulb, similar to the structure of the working electrode 112. The external test fluid therefore cannot mingle with and contaminate the internal fill solution of the reference electrode. FIG. 2 shows schematically a single electrode/sensor pH meter 202 with a sensor electrode 212 and meter electronics 214. Sensor electrode 212 comprises a working electrode (not visible in FIG. 2), a counter electrode (not visible in FIG. 2) and a reference electrode (not visible in FIG. 2).

Another pH electrode is described in U.S. provisional patent application Ser. No. 60/981,334 which describes a multiple electrode ion meter that does not include a salt bridge. The entire contents and disclosure of this provisional patent application is incorporated herein by reference.

In addition to glass electrodes described above, other materials exist for the detection of ions in solution. Carbon nanotubes (CNTs) have been described extensively in the art as a possible ion detection material.

In Gregory G. Wildgoose, Chemically Modified Carbon Nanotubes for Use in Electroanalysis, 152 Microchim Acta, 187-214 (2006), the history and a number of uses for CNTS in electroanalysis are described. Different methods for modifying CNTs via covalent or physisorption, electropolymerisation, and other miscellaneous methods are show that allow the CNTs to be customized to interact with different companion compounds. CNTs can be functionalized in such a fashion that their direct interaction with $H_3O^+$ results in a detectable modified voltammetric response that can then be used to determine the concentration of pH in a solution—effectively resulting in a pH electrode. CNTs can also be modified per the methods described above to interact specifically with several other cations, anions, gasses, and biological molecules such as nucleosides, nucleotides, nucleic acids, sugars, and any other conceivable compound or worthy of measurement in modern chemistry.

Because CNTs are comprised of graphene sheets, and graphite has known electrical properties, CNTs have unique electrical properties. Varying the structure of the CNT by directly modifying the CNT graphene structure, sub-macromolecular assembly, chirality, or by functionalization results in modified electrical properties of the CNT. This electrical characteristic and broad malleable platform in which to operate, makes CNTs desirable materials for electrode design and construction.

Further, because CNTs have a Sp2 configuration, as opposed to the Sp3 configuration of Diamonds, CNTs are considerably strong and resilient for their weight. Increased strength and durability makes CNTs desirable materials for electrode design and construction in environmental and harsh industrial applications. Durability of electrodes is desirable because often sensors are placed in applications that are dangerous and expensive to access. The longer the sensor lasts the lower the consumer expense—hence using CNTs in sensors is motivated economically.

Methods of synthesizing and growing CNTs and arrays of CNTs that may be used in sensors are also described in U.S. Pat. No. 6,841,139 to Margrave et al. issued Jan. 11, 2005; U.S. Pat. No. 6,790,425 to Smalley et al., issued Sep. 14, 2004; U.S. Pat. No. 7,067,098 to Colbert et al. issued Jun. 27, 2006; and U.S. Pat. No. 7,465,494, and the entire contents and disclosures of these patents is incorporated herein by reference.

Although systems exist for the local monitoring of discrete, independent treatment site locations for individual analysis, these systems do not contemplate remote monitoring of one or a number of water treatments sites throughout a collection system that simultaneously feed effluents into a central water collection system of a WWTP. There remains a need for a system designed for remote monitoring of a WWTP via CNT based sensors which may collect and interpret data from one or a multiple number of remote industrial or water treatment sites viewed and analyzed as an aggregate water treatment system.

One of the problems with maintaining advanced processing equipment is the need for highly qualified individuals to monitor its operation. Employment of a full time staff is costly and can be problematic since such monitoring is repetitive, and highly qualified individuals can easily become bored or distracted. For this reason, advanced separation processes may include a large assortment of strategically placed CNT based sensors that are typically incorporated into a computer system capable of comparing the CNT sensor values against a pre-set quality level. However, if the operator is not notified, does not recognize a particular alarm or does not recognize an abnormal condition, the elaborate array of monitoring equipment is effectively useless.

Another problem with the current state of the art involving CNT sensors is the inability of prior art sensors to use the unique hydrophobic and hydrophilic characteristics of the CNT to filter out and/or attract analytes thus resulting in increased sensor sensitivity and improved measurement accuracy. There has not heretofore been described a process for measuring ions in liquids utilizing CNT hydrophobic design having the features and advantages provided by the present invention.

Another problem that the current state of the art involving CNT sensors does not address is pipe-sensor integrated CNT based sensors. There has not heretofore been described a process for measuring ions in liquids utilizing CNT hydrophobic design having the features and advantages provided by the present invention.

Another problem that the current state of the art involving CNT sensors does not address is the protection of potable water from CNT sensors. There are some studies that calm that possible exposure to CNTs either by way of water or air may be harmful to mammals. There has not heretofore been described a way of protecting potable water from CNTs including the detection of loss of CNTs in a sensor having the features and advantages provided by the present invention.

Another problem that the current state of the art involving CNT sensors does not address is the detection of CNTs via CNT associated markers in fluids, gasses, air, or supercritical phases. If CNTs are to be integrated into water and industrial monitoring applications, and if it is show that CNTs are harmful to mammals, then CNT loss detection is required. There has not heretofore been described a way of detecting CNTs in various materials having the features and advantages provided by the present invention.

Another problem that the current state of the art involving CNT sensors does not address is the hybridized analysis of liquids utilizing colormetric analysis and CNT detection. The two methods combined will result in increased accuracy and a self-diagnostic sensor function. There has not heretofore been described a way of liquid analysis utilizing a hybridized CNT and colormetric analysis having the features and advantages provided by the present invention.

Another problem that the current state of art involving CNT sensors does not address is the custom functionalization of CNTs for specific water analysis methods. Most modernday water analysis methods involve modification of an organic compound that results in a change of color. The change of color then indicates the concentration of the analyte of interest. There has not heretofore been described a functionalization of CNTs for water analysis methods having the features and advantages provided by the present invention.

An advantage of carbon nanotubes being hydrophilic is that the carbon nanotubes will help to draw water into the array, and as a result, the subsequent matter of interest in the water. For example, the water will integrate into the array, and along with it the various concentration of $[H_3O^+]$ (in the case of pH, or $CL_2$, or $HOCl_2$, etc. . . . ), thus allowing for increased sensor sensitivity and thus higher quality measurements at low ionic analyte concentrations.

In one embodiment of the CNT sensor the CNT array is hydrophilic. First the CNT is grown non-functionalized comprising carbon and hydrogen only. Then, the terminus is generally at least 25% of the CNT is functionalized with a hydrophilic functional group. Hydrophilic functional groups are generally polar and/or ionic and may have positive or negative charges. The polar and/or ionic nature of the functional group is attracted to water because water is also a polar molecule that creates hydrogen bonds with the polar functional group, thus allowing the functional group to dissolve into the water. Examples of suitable hydrophilic groups include (described as the non-ionized structure) amino, hydroxyl, carboxyl, phosphate, sulfhydryl, aldehyde, ketone, etc.

Embodiments of the present invention provide a method and system for remotely monitoring, storing, analyzing, manipulating, uploading, reporting, etc., information and data relating to water quality and/or treatment derived from raw data obtained from a plurality of sensors of a water treatment system, which may be strategically placed to gather data or information necessary for analysis or manipulation. Such information and data may be remotely stored, manipulated, etc., on one or more remote computer(s), and/or stored on one or more removed database(s), which may be associated with the remote computer(s). A water treatment system according to embodiments of the present invention may include any system designed or used to generate water or a water-based product having a predetermined, desired, or preferred set of characteristics, qualities, properties, etc., for a particular application, such as, for example, a municipal potable drinking water treatment facility, a system generating water for a manufacturing process, etc., as well as any distribution system. A water treatment system may also include any system designed or used to process or treat a water-based substance into a product discharged into the environment, such as, for example, a central wastewater treatment plant (WWTP), etc., as well as any collection system. Water treatment systems may include a public or municipal system as well as a system dedicated to a real estate development. For example, a water treatment system may include any system, plant, or facility that uses equipment based on advanced separation, filtration, dialysis, ion exchange processes, or any other basis, technology, or mechanism for processing, treating, detecting, purifying, isolating, separating, etc., water according to relevant parameters.

Figure 3:
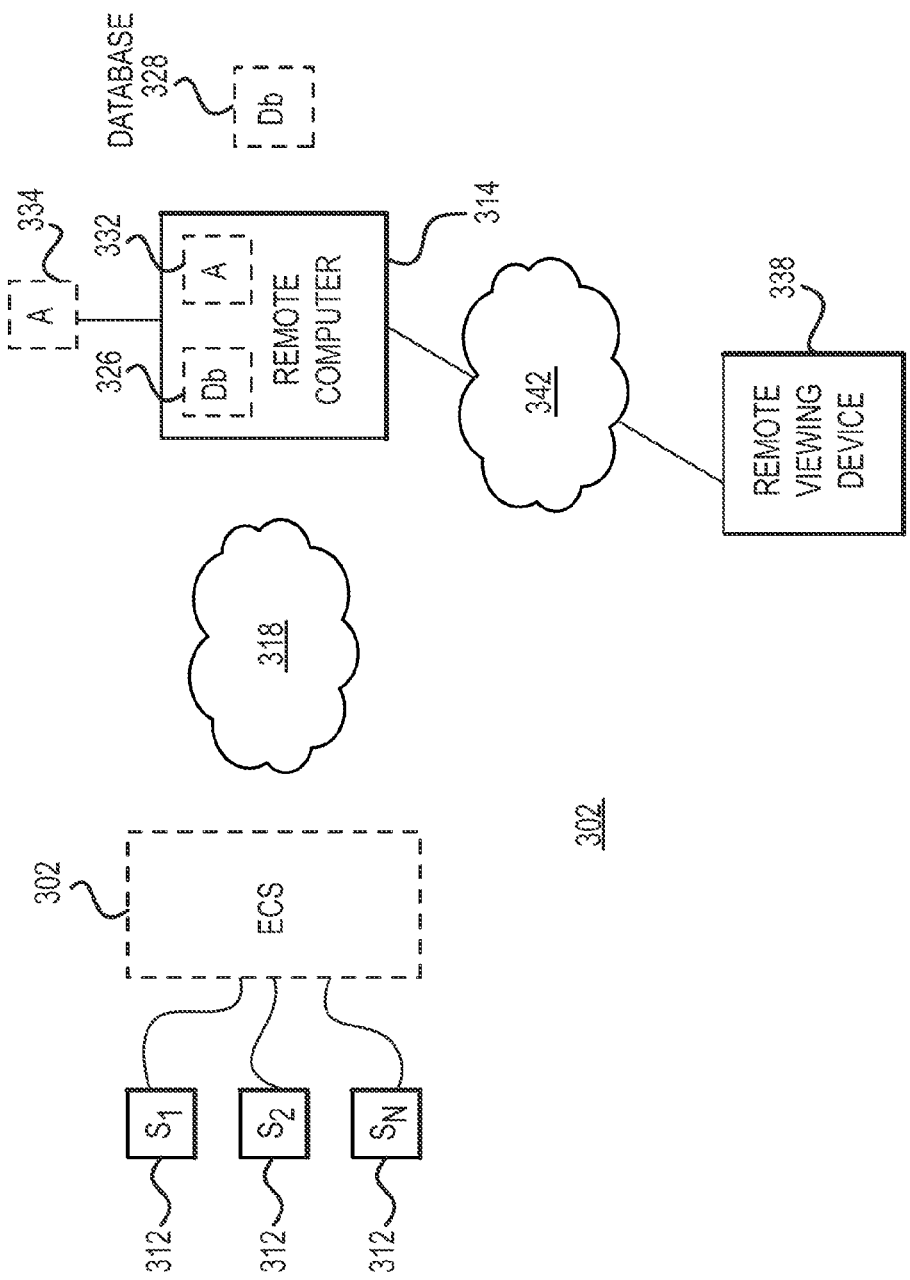
FIG. 3 is a diagram of an embodiment of the remote monitoring system in accordance with one embodiment the present invention.

According to embodiments of the present invention as shown in FIG. 3, remote monitoring system 302 collects raw data from one or more sensors 312 located within a water treatment system and transmits such raw data to a remote computer(s) 314 via any known technology or mode of transmission 318. Although the embodiments shown in the figure depict data from sensors 312 being transmitted to remote computer 314 via an optional electronic control system (ECS) 320, it is to be appreciated that sensors 312 may transmit data directly to remote computer 314, which may occur in the absence of optional electronic control system (ECS) 320. According to some embodiments, remote computer 314 may be, for example, an Internet server computer. Remote computer 314 may store and/or manipulate raw data to produce an analysis result(s). Remote computer 314 may store data on a remote database 326 that is located on remote computer 314 for storing the data. Alternatively, data may be stored by remote computer 314 on a remote database 328 associated with remote computer 314. The manipulation or analysis of data may be performed by an analyzer 332 that is located on remote computer 314 or on an analyzer 334 that is associated with remote computer 314. The analyzer may also be software that executed directly by remote computer 314. According to some embodiments, one or more sensors 312 may optionally transmit raw data to the remote computer 314 via an electronic control system 320, which may also control operation of the equipment of the water treatment system.

The analyzer in the embodiments of the invention shown in FIG. 3 may comprise hardware and/or software.

Once data is stored in either remote computer 314, remote database on remote computer 326, and/or remote database 328, analyzer 332, 334 on or executed by remote computer 314 may then analyze or manipulate data to generate manipulated data and/or an output including data and information, such as an analysis result(s) or analysis report(s), presenting or indicating the qualities, characteristics, properties, etc., of the water being treated and/or the operation of the water treatment system. The manipulation or analysis of data by analyzer 332, 334 may be performed continuously, in real time, at periodic or selected intervals, on condition, or on demand for presentation to a user. Following analysis or manipulation by analyzer 332, 334, the information, data, and/or analysis result(s) or report(s) may then be sent to a remote viewing device 338 using any known mode of communication 342. However, it is to be understood that according to some embodiments, raw data or direct readings may be reported directly to a user 338 without analysis or manipulation or with analysis or manipulation performed only locally, such as by the electronic control system 320.

According to some embodiments, the information, data, and/or analysis result(s) may optionally be manipulated and displayed in an output, such as an analysis report(s), in a predetermined format, which may then be sent to a user, such as, for example, a consumer, public official, authorized personnel, or regulatory agency. Indeed, the manipulated data or analysis results may be formatted into an output or analysis report as required for submission to a regulatory agency. According to some embodiments, the analysis or manipulation of data may be presented as an output that is uploaded onto to a web server and made accessible via a web browser for presentation to, for example, a public official, consumer, or interested member of the public. Alternatively, according to some embodiments, the analysis or manipulation of data may simply send an output in the form of an alarm to alert a user of a problem or deviation.

Figure 4:
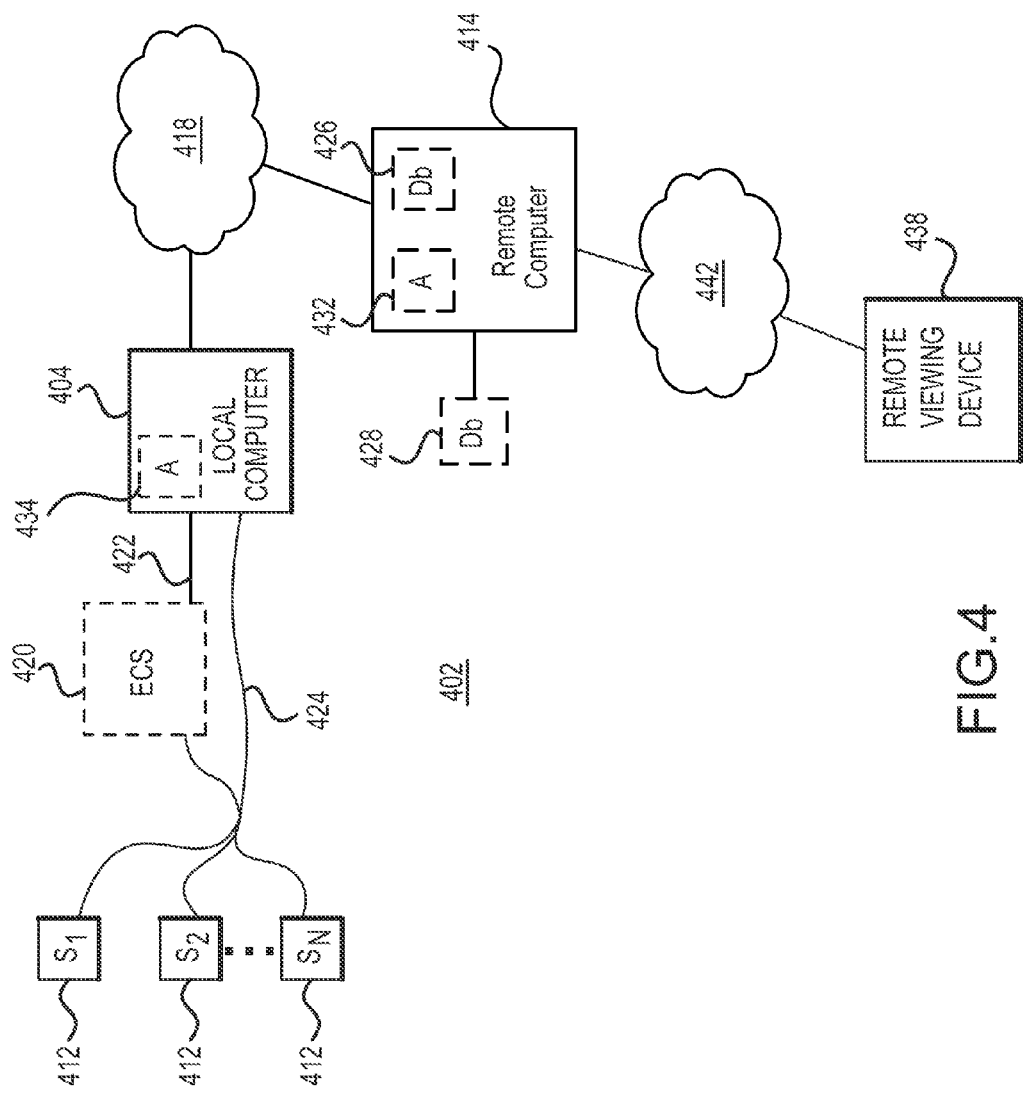
FIG. 4 is a diagram of an embodiment of the remote monitoring system in accordance with one embodiment present invention with a local computer.

According to some embodiments as shown in FIG. 4, remote monitoring system 402 of the present invention may operate similarly to remote monitoring system 302 shown in FIG. 3 but further includes a local computer 404, that may locally store, process, access, analyze, and/or manipulate raw data obtained from one or more sensors 412 of the water treatment system before being transmitted to a remote computer 414 by a mode of transmission 418. Other aspects of these embodiments may be similar or identical to those described above in relation to FIG. 3. Remote monitoring system 402 may optionally include an electronic control system 420 linked to sensors 412, and local computer 404 may access capture, or receive data from one or more sensors 412 via electronic control system 420 using a local connection 422, and/or directly from sensors 412 via local connection 424 especially in the absence of an electronic control system 420. Local computer 404 may then transmit data by any suitable mode of transmission 418 to remote computer 414, and data may be stored in a remote database 426 located on remote computer 414. Alternatively, data may be stored by remote computer 414 on a remote database 428 associated with remote computer 414. Following analysis or manipulation by an analyzer 432, 434, the information, data, and/or analysis result(s) or report(s) may then be sent as an output to a remote viewing device 438 for viewing by a user using any suitable mode of communication 442. The analyzer may comprise hardware and/or software.

According to some embodiments, the analyzer 432 may be located on or executed by the remote computer 414. Alternatively, the analyzer 432, 434 may be located on or executed by the remote computer 414 and/or the local computer 404. According to embodiments having an analyzer 434 located on or executed by local computer 404, local computer 404 may send observational data in addition to other information of data to remote computer 414 via a mode of transmission. Such observational data may be data or information derived or synthesized from raw data obtained from the one or more sensors 412 that has been analyzed or manipulated by analyzer 434. Data transmitted from local computer 404 to remote computer 414 may include data and information, such as an analysis result(s) or analysis report(s), relating to the qualities, characteristics, properties, etc., of the water being treated and/or the operation of the water treatment system.

The analyzer in the embodiments of the invention shown in FIG. 4 may comprise hardware and/or software.

According to embodiments of the present invention, remote computer 314, 414 of remote monitoring system 302, 402 in reference to FIGS. 3 and 4 is located at a different and physically distinct and remote location than the water treatment system, which may include local computer 404. The remote computer 314, 414 of remote monitoring system 302, 402 may not be used to remotely control or direct controls for a water treatment system, such as an electronic control system 320, 420. Indeed, according to embodiments of the present invention, the only communicative or electronic link or connection between (1) the remote computer and (2) the water treatment system or the sensors, electronic control system, and/or local computer located within the water treatment system may be the mode of transmission of the present remote monitoring system. Several benefits and advantages may be achieved by physically separating the storage, manipulation, analysis, reporting, etc., functions of the remote computer and/or remote database of the present invention from the site(s) or location(s) of data collection (i.e., sensors) within a water treatment system, which may further include a broader distribution or collection system.

According to embodiments of the present invention, local computer may be any type of computer, processor, or device able to (1) at least temporarily store, assemble, collect, aggregate, etc., data from one or more sensors, and (2) transmit data or information to a remote computer (or a remote database associated with the remote computer) via a mode of transmission. Thus, a local computer may contain or include (1) a memory device(s) to store, assemble, collect, aggregate, etc., the data at least temporarily, (2) one or more ports or inputs for receiving data or information either directly or indirectly from one or more sensors, and (3) a transmission interface(s) to transmit data or information to a remote computer. Such a local computer may further have the ability to process, manipulate, analyze, etc., the data obtained from the one or more sensors, such as by an analyzer or software located on local computer, prior to transmission of data or information to the remote computer and/or remote database. The data sent from the local computer to the remote computer and/or remote database may be observational data synthesized from data derived from one or more sensors. The local computer may be located at or near a water treatment system and/or the site(s) of one or more sensors within a water treatment system which may include a distribution system or collection system. The remote monitoring system of the present invention may comprise one or more local computers each associated with one or more sensors to collect, store, and/or transmit data or information derived from the one or more sensors to a remote computer via a mode of transmission. Each of the one or more local computers may transmit the data or information to the remote computer via the same or different mode(s) of transmission.

According to some embodiments, local computer may comprise a logger device located at or near site(s) of at least one sensor. Such a logger device may include one or more sensor ports for receiving data through cables, wires, etc., from one or more sensors. Alternatively, such a logger device may be capable of receiving data wirelessly from one or more sensors. To store or log (at least temporarily) data or information received ultimately from the one or more sensors and/or manipulated or analyzed, logger device may have any type of memory device known in the art, such as a drive, flash or SIM card, etc. Thus, logger device may further include an analyzer or software to analyze or manipulate the data from the one or more sensors. The logger device may have a transmission interface, such as wireless connectivity or antenna or other connection outputs, for communicating via a mode of transmission to a remote computer or server.

According to some embodiments, the logger device may have inputs, connectors, or ports for a plurality of sensors, such as at least four sensors, which may be automatically detected for plug-and-play options. The logger device may be able to store or log data for a greater number of values or measurements than ports, such as up to 16 values. Each sensor port may receive data from a sensor comprised of multiple individual sensors. The logger device may have different power options, such as battery power, auxiliary (external) battery power, reusable source (e.g., solar panel, etc.), and/or power from the electrical grid which may be combined with power switching (i.e., using battery or auxiliary power as a back-up). The logger device may further have inputs, connectors, or ports for receiving auxiliary power or a data communication link for connecting to a user computer or laptop. The logger device may also have a user interface for providing basic indications/information, such as device or sensor status, connections, etc. The logger device may be water-tight, enclosed, and/or have a rugged construction, may contain a desiccant to control moisture within the device, and/or may include a means for mounting the device. An example of a flow logger may include any FLO-LOGGER® product known in the art.

According to embodiments of the present invention, raw data about the operation of a water treatment system or the characteristics, conditions, qualities, properties, etc., of water processed or treated by a water treatment system may be acquired, collected, detected, measured, etc., by one or more sensors or probes placed at one or more sites or locations within or throughout the water treatment system, such as a plurality of locations within or throughout the water treatment system, which may include sites in the field, i.e., in a collection or distribution system. Sensors may be strategically placed to gather relevant data and information at appropriate sites or locations and/or provide logical functional groupings for review and analysis.

According to embodiments of the present invention, the one or more sensors may be used to obtain relevant raw data about the operation of a water treatment system and/or the quality of water being processed, treated, received, distributed, etc., that would be relevant to the analysis, manipulation, and evaluation of the data in generating an output, such as an analysis result, analysis report, alarm, etc. For example, each of the one or more sensors may be used to measure, quantify, or detect the following characteristics, conditions, qualities, properties, etc., of water. Examples of characteristics, conditions, qualities, properties, etc., of water that may be measured by the one or more sensors may include, but are not limited to: water temperature, chemical composition including total organic carbon (TOC), total suspended particles, quantity, flow rate, and types and amounts of waste(s) such as those commonly discharged into streams from waste water treatment or industrial sites. Further examples of characteristics, conditions, qualities, properties, etc., of water that may be measured by the one or more sensors may include contaminant(s), conductivity, pH, pressure, turbidity, permeate flow, dissolved oxygen, chlorine or fluorine concentration(s), tank or water level(s), and equipment status and operation. According to some embodiments, the one or more sensors may be chosen to generate data or information for a regulatory report necessary to enable a regulatory agency to determine operational parameters and quality and quantity of the treated water such as water production rate (flow), treated water consumption rate (flow), treated water storage volume, reserve capacity (at current production and consumption rates), final treated water quality, reports and archive data for regulatory compliance and/or QA/QC documentation. According to embodiments of the present invention, examples of sensors that may be used with the remote monitoring system of the present invention may include any sensor known or used in the art. In addition to the variables listed above, the one or more sensors may be used to measure water level and/or flow velocity using any technology either known or later developed in the art. Such measurements may, for example, be used in combination to determine volumetric flow rate along with other known conditions and constants. An example of a sensor may further include a rain gauge. Examples of flow velocity or area flow velocity sensors that may be used with embodiments of the present invention may include wafer sensors and any sensor based on Doppler or ultrasonic, radar, pressure flow, electromagnetic (EM), magnetic (e.g., surcharge), etc., technology or detection. Examples of level, height, or depth sensors that may be used with embodiments of the present invention may include any based on ultrasonic (look-down, submerged look-up, in-pipe, etc.), pressure (e.g., bubbler, surcharge, diaphragm displacement, etc.), radar, etc., technology or detection. According to some embodiments, a height or level sensor may be combined with other structural elements or devices, such as flumes and weirs, to deduce other measurements or states, such as velocity in addition to water level, based on known relationships and constants. According to some embodiments, any of the one or more sensors may further include an internal or external temperature sensor to provide, for example, auto correction for effects of temperature on any primary measurement by the sensor. A sensor according to some embodiments of the present invention may each comprise a plurality of sensors, which may then be jointly fed into a local computer, such as a logger device.

According to embodiments of the present invention, the one or more sensors may include any products on the market, sold, made by, or branded under, for example, Hach™ Sigma™ or American Sigma™, Marsh-McBirney™, etc., either known or later developed in the art. Particular examples of the one or more sensors may include FLO-DAR®, FLO-TOTE®, FLO-MATE®, etc., sensors. For additional description of some types of sensors, see, e.g., U.S. Pat. Nos. 5,506,791, 5,633,809, 5,691,914, 6,208,943, 5,644,088, 5,811,688, 5,544,531, and 5,315,880, the contents and disclosures of which are hereby incorporated by reference in their entirety.

In the case of water districts, electronic sensors may be used to detect or measure the amount of storage, discharge pressure and flow from the systems. Other parameters may be determined by analytical tests. Many of the sensors used to continuously monitor water treatment operations are based on advanced separation processes employing selective ion membranes which concentrate the analyte for detection. For example, detection of chlorine may be mediated via an ion selective membrane which may readily and specifically pass an analyte, such as free chlorine or hypochlorous acid (HOCl), thus separating and concentrating the analyte from the bulk solution. The sensors may incorporate multiple sensors as part of a single detector unit.

The presence or absence of turbidity in the water supply may greatly affect the amount of disinfectant required to achieve inactivation of biological organisms. The suspended particles producing turbidity are usually removed in the water treatment process before disinfection agents are applied. However, turbidity breakthroughs do occur and failure to quickly raise the disinfection dose level may lead to insufficient disinfection residuals reaching the distribution system.

This may present a threat to public health, particularly if the drinking water supply is contaminated either deliberately or inadvertently.

According to embodiments of the present invention, the one or more sensors may optionally be integrated with or connected to an electronic control system. The electronic control system may generally be used to control the operation of a water treatment system by local operators. Examples of an electronic control system may include an in-house Supervisory Control and Data Acquisition System (SCADA) or a Progammable Logic Controller (PLC). The electronic control system may be composed of any available commercial devices for converting analog to digital, such as Analog to Digital boards, specifically designed for the purpose of converting instrument readings or data to computer readable form. Thus, the remote monitoring system of the present invention may utilize existing instrumentation and control systems as well as existing communication devices. The electronic control system may perform basic analysis of the raw data to produce an analysis parameter that may then be sent to the remote computer. According to some embodiments, the electronic control system may continuously scan the sensor data and automatically log and archive the data at specified intervals. According to some embodiments, raw data obtained from a sensor may be stamped or labeled with time and location information, such as a unique identifier(s), for aiding subsequent analysis or manipulation. Raw data obtained from a sensor may also be labeled according to the particular order in which the data is sent to a remote computer. According to some embodiments, the electronic control system may include a transmission interface which functions to transmit the data to the remote computer.

According to some embodiments, the remote monitoring system may further include a local computer located at or near the physical location of the water treatment system and/or the site(s) of one or more sensors within a water treatment system which may include a distribution system or collection system. For example, the local computer may be a logger device as described above. The local computer may read, query, access the data collected from the one or more sensors of the water treatment system, store in an appropriate electronic format at least transiently, process, manipulate, analyze, etc., the data obtained from the one or more sensors, such as by an analyzer or software located on local computer, and/or transmit the data to the remote computer. For example, storage of the data on the local computer may provide an on-site data backup, and the data may be added to an historical data file for use in analysis to allow a current data file to be reused for new data collection. According to some embodiments, the local computer may be connected to the electronic control system and access the data via the electronic control system. Any type of connection, electronic or otherwise, may be used, such as, for example, a serial interface board, a USB interface card, a network connection, wiring, etc. According to some embodiments, a user may use the local computer to view or display the data or results or reports generated from the data stored and/or analyzed, manipulated, etc. on a remote computer.

According to some embodiments, a local configuration file on the local computer may tell a program on the local computer which of the register addresses of the electronic control system to access, any scaling factor which needs to be applied, a physical description of the data being collected, etc. The data set collected may then be converted into a form for transmission, such as a comma delimited string value, and perhaps stored locally and possibly encrypted for security on a storage medium such as a hard disk, etc.

According to embodiments of the present invention, the data and information obtained, acquired, collected, detected, measured, etc., from the one or more sensors may be transmitted to a remote computer, located off-site, using any known or available mode of transmission. The data and information may be transmitted either directly from the one or more sensors, from the electronic control system, or from a local computer connected to the electronic control system and/or directly to the one or more sensors. Once transmitted and received by the remote computer, the data and information may then be remotely stored on the remote computer and/or a remote database on or associated with the remote computer. According to some embodiments, the data and information may then be manipulated on the remote computer to generate an output, such as an analysis result, report, alarm, etc., that may be communicated to a user, and/or the data and information used to generate an output may be manipulated on the local computer prior to transmission to the remote computer. Such data or information transmitted from a local computer may include observational data which is calculated, manipulated, etc., by an analyzer on the local computer from data derived from one or more sensors. According to some embodiments, the data and information may be analyzed, manipulated, etc., by analyzer(s) located on both the remote computer and the local computer.

According to embodiments of the present invention, the remote monitoring system of the present invention may further comprise a remote database or software-implemented remote database associated with the remote computer for storage of data. The remote database may be on the remote computer or exist as a separate unit, and the number of remote computer(s) and/or remote database(s) may be varied to suit a particular application, network traffic, or demands of a particular client. According to some embodiments, for example, the remote computer may comprise a computer, an ftp server, a remote database, and/or a web or internet server, which may each be located at the same or different locations and use any available and appropriate operating systems. This storage on the remote database may take many forms such as flat files, spreadsheets, and relational or non-relational databases. According to some embodiments, for example, the remote database may be a relational database, such as Microsoft SQL Server or Oracle database products.

According to embodiments of the present invention, the exact mode of transmission may vary depending on the circumstances. Any suitable technology or device known and available in the art for transmitting data to a remote or physically separated computer is contemplated for use as a mode of transmission according to embodiments of the present invention. Examples of modes of transmission may be achieved through any suitable medium. According to embodiments of the present invention, the data may be transmitted, for example, continuously, in real time, at periodic or selected intervals, on condition, or on demand by a user. The data may also be encrypted for security for additional security, and may be decoded by the remote computer and/or the remote database and placed in the appropriate locations.

According to some embodiments, the data may be transmitted to the remote computer directly by sensor assemblies comprising the one or more sensors. According to these embodiments, the one or more sensors may be fitted with communications processors which enable the sensors to send data directly to the remote computer. Suitable instruments may include sensor assemblies having a transmission interface effective for real time data transmission, such as a LonWorks® network variable interface. Suitable sensors may also include, for example, the Six-CENSE® and the CT- CENSE® manufactured by Dascore, Inc., as well as the multi-sensor devices manufactured by Sensicore, Inc. In this example, sensors may transmit the data to a remote computer by any suitable mode of transmission known in the art, such as an Internet server computer, and may be connected to a remote computer through existing telephone wiring on a dedicated network connection or cell network.

According to some embodiments, the data may be transmitted to the remote computer via an electronic control system connected or coupled to the one or more sensors using any suitable mode of transmission known in the art. For example, a section of ladder logic or function block program code may be inserted into the code base of the electronic control system which directs the electronic control system to send specified data to the remote computer and/or database. The communications protocol may be any protocol supported by the electronic control system which facilitates the transmission. For example, RSLinx®, a software program from Rockwell Software, may be operative on the remote database computer to facilitate the transmission by a PLC. Alternatively, any number of commercial communications drivers may be used such as those produced by commercial providers such as Kepware®, Wonderware®, and so on. In the case of an electronic control system typified by SCADA® or HMI® products, such as Wonderware®, RSView®, WinCC®, and other similar products, code blocks may be added to the control code to allow the operating program to collect and send data to the remote computer. Thus, the steps of collecting data locally, possibly storing it temporarily, and subsequently transmitting this data to a remote computer may be incorporated into the electronic control system.

According to some embodiments, the data may be transmitted to the remote computer via a local computer connected or coupled to the one or more sensors directly or through an electronic control system connected or coupled to the one or more sensors. According to these embodiments, the local computer may transmit the data acquired or collected directly or indirectly from the one or more sensors to the remote computer by any suitable mode of transmission known in the art. According to some embodiments, for example, the local computer may comprise a logger device as described above located at or near site(s) of at least one sensor.

According to embodiments of the present invention, after the data and information obtained from the one or more sensors has been sent to the remote computer of the remote monitoring system, the remote computer may analyze or manipulate the data to generate an output, such as manipulated data, an analysis result, an analysis report, an alarm, etc. Alternatively, the local computer may analyze or manipulate the data and information obtained from the one or more sensors which may then be transmitted to the remote computer, and the remote computer may then further analyze or manipulate the data and information to generate an output. However, the output may be generated, presented, uploaded, etc., by the remote computer without further analysis or manipulation by the remote computer. The analysis, manipulation, etc., of the data may be performed by an analyzer, such as a software program or routine, firmware, and/or hardware, that may be housed on the local computer, the remote computer, and/or the remote database associated with the remote computer.

According to embodiments of the present invention, the analyzer may be one or more software program(s) on the remote computer and/or on the local computer. Such an analyzer may perform analysis, calculation, comparison, manipulation, etc., of the data to generate an output, such as an analysis result, an analysis report, an alarm, etc., relevant to the monitoring of a water treatment system, and the analysis, calculation, comparison, manipulation, etc., may be performed continuously, in real time, at periodic or selected intervals, on condition, or on demand. According to embodiments of the present invention, an analyzer may be used to make calculations based on a combination of raw data from multiple sensors. When the analyzer is located on a local computer, the analyzer may be used to generate or synthesize observational data derived from raw data obtained from a plurality of sensors. For example, independent data measurements of (1) flow rate and (2) water level by multiple sensors may be combined and used to calculate volumetric flow (in units of volume per time) based on the known dimensions and other constants regarding a water channel, pipe, etc., at a site within a water treatment system. Such multiple sensors used to measure volumetric flow may be connected to a common local computer, such as a logger device.

According to embodiments of the present invention, the data acquired or collected from the one or more sensors may be compared by the analyzer to expected or historical performance data or records and/or to any known values and constants, such as known or expected transit times, location-specific flow rates and patterns, and distances within different portions of a water treatment system, known physical and chemical properties and characteristics of water, contaminants, disinfectants, pollutants, etc., using any known equations, algorithms, etc., which may be used to model, predict, or compare the performance of the water treatment system or the quality of water processed or treated by the water treatment system. Data acquired or collected from the one or more sensors may be compared to each other and/or to historical data, and calculations may be performed to generate an output, such as an analysis result(s), etc. According to embodiments of the present invention, the analyzer or software may perform any calculation, computation, comparison, analysis, etc., that would be relevant, suitable, or appropriate to monitoring of the operation of a water treatment system or the processing or treatment of water in a water treatment system.

According to some embodiments, an analyzer on the local computer, the remote computer, and/or remote database associated with the remote computer may also interpret and consider any identifier(s) or configuration files associated with the data that may indicate or identify the origin, location, and time of the data capture from the one or more sensors. The analysis and calculation of the data may further be performed by the analyzer to determine or indicate performance, evaluation, preventative maintenance, scheduling, optimization, and trouble shooting of the operation of the water treatment system or equipment, in addition to monitoring water quality. For example, the data may be compared to known or expected performance data or parameters to calculate a differential, which may be used to determine if the water treatment system is performing within a normal range or out of bounds if a predetermined differential is exceeded. Such comparisons may be based on the amount or concentration of, for example, a disinfectant, contaminant, or pollutant present at different locations in a water treatment system. If the differential is exceeded, then appropriate persons, operators, and/or agencies may be alerted. Alternatively, for example, the data may be compared to known, expected, or historical data or values to determine if the operation of the water treatment system is optimized.

According to some embodiments, the analyzer may convert the data into a consistent set of units, and thus translates all values into a common format, such as pounds per square inch (psi) for pressure, etc., using a units conversion subprogram to allow for appropriate comparisons and calculations. Furthermore, the data may be normalized to specific configurations and conditions for a water treatment system. For example, the feed pressure may be critical in determining the future and current performance of a system in reference to its performance when new. For reverse osmosis membranes, changes in pressure are related to age, production rate, and temperature and vice versa. Thus, a change in flow rate may or may not indicate that the overall system's performance has changed when normalized and compared to its performance when new or recently cleaned. Prior to this invention, the complex mathematics for these conversions required some manual intervention on the part of the operator to compute the normalized conditions. Embodiments of the instant invention may do this automatically and report normalized data to the output.

According to some embodiments, the analyzer or software of the present remote monitoring system may be used to make any suitable statistical inferences, derivations, conclusions, or predictions from the data, especially based on a comparison to historical data or expected values. Such an analysis or manipulation of the data may provide an indicator of either normal or abnormal operation of a water treatment system or characteristics, properties, qualities, etc. of water processed or treated by a water treatment system. According to some embodiments, the analyzer may be used to predict conditions, such as the presence, quantity, or concentration of a disinfectant, contaminant, or pollutant at a downstream location at a later point in time based on data obtained from sensors at upstream locations within a water treatment system.

For example, in the context of a water treatment facility for providing potable drinking water to the public, data, disinfectant concentration and turbidity, may be analyzed from both the treatment facility and the distribution system, and historical information as well as known constants may be used to predict expected conditions at points downstream within the distribution system based on expected lag times and the effluent conditions from the treatment facility. For example, data may be collected from the water treatment facility about relevant information, such as chemical dosing rates, filtered water turbidity, chlorine residual, etc. as well as data from sensors in the distribution system, such as chlorine residual, etc., may be used for comparison. With historical data as a reference point, one can calculate a chlorine demand from the chemical dose rates, flows, and residual using the current data. Chlorine Demand may be defined as the actual amount of chlorine which is reacting, typically calculated as free chlorine dosed less the residual. Chlorine demand may be correlated with temperature, season, and filtered water turbidity. Additionally, residual chlorine leaving the plant may be correlated with residual chlorine within the distribution system. If the actual chlorine residual measured at the distribution system point of measurement varies from the historical values expected from the chlorine residual leaving the treatment facility by more than a set percentage or number of standard deviations, then an alarm or alert may be issued by the remote monitoring system of the instant invention.

As another example in the context of a water treatment facility for providing potable drinking water to the public, data obtained from the one or more sensors may be combined with known system constants such as flow rates, residence times, and so on, to continuously generate a calculated product of disinfectant concentration times contact time C*T. This simple factor alone is quite useful in predicting the amount of biological organism deactivation.

As another example in the context of a waste water treatment plant (WWTP), an analysis or manipulation of data obtained from sensors at upstream locations in a collection system, such as sites or locations of discharge from water treatment or industrial waste water plants, to detect the amount of a contaminant, pollutant, may be used to predict the future composition and flow rate of water arriving at the central WWTP. This may be accomplished in a simple manner by using known or expected constants and information as well as historical records about transit time, flow rates and patterns, etc., from each of the relevant sites or locations upstream, such as within the collection system and at or near points of discharge. Any results, conclusions, reports, etc., generated using such an analysis or manipulation may be used to alert operators of a central WWTP receiving waste water from the collection system of a potential overload so that appropriate precautions and changes in operation may be made. As will be readily appreciated by those skilled in the art of data analysis, this can provide a powerful indicator of either normal conditions expected at the WWTP or out of bounds conditions that may require immediate action and notification of responsible parties.

According to other embodiments, the projected or remaining life of equipment, such as a membrane, may be determined or estimated by the remote monitoring system based on operational performance data. Efficiency levels for equipment or a water treatment system as a whole may be determined by the remote monitoring system relative to a theoretical potential or efficiency, which may be based on a theoretical minimum water, power, and chemical consumption versus actual consumption calculated. In addition, financial and economic reports may also be generated based on performance and/or consumption data. Furthermore, the data may be analyzed and compared to federal and/or state regulatory requirements for water quality and environmental protections.

According to some embodiments, the information and data may be displayed or presented as an output, such as an analysis result(s) and/or analysis report(s), in a predetermined format, which may then be sent to a user, such as, for example, a consumer, public official, authorized personnel, or regulatory agency. Indeed, the data may be manipulated and formatted into an output or analysis report as required for submission to a regulatory agency. According to some embodiments, the analysis or manipulation of data may be presented as an output that is uploaded onto to a web server and made accessible via a web browser for presentation to, for example, a public official, consumer, or interested member of the public. Alternatively, according to some embodiments, an output in the form of an alarm may be sent to alert a user of a problem or deviation from normal conditions.

According to embodiments of the present invention, once the data is analyzed or manipulated into an output, such as an analysis result or analysis report, the output may be sent by any known, available, and/or suitable mode of communication from the remote computer to a remote viewing device for viewing by a user. According to some embodiments, the output may be sent to the remote viewing device or accessed by the remote viewing device continuously, in real time, at periodic or selected intervals, on condition, or on demand. For example, the output may be a notification, alarm, or alert, such as an Alarm Event, sent on condition of an emergency or abnormal, harmful, or dangerous quality, state, or condition relating to a water treatment system. Such an output may include a notification of failures, shutdowns, exceeding of critical parameters, equipment damage, etc. Alternatively, for example, the output may be composed as an analysis report, which may be in a format for submission to a regulatory and/or law enforcement agency. The remote monitoring system may send, present, or upload an output as a weekly, monthly, yearly, etc. summary of performance, water quality, or other information that may be reviewed by management for the water treatment system or by elected officials, customers, vendors, or members of the public. Alternatively, the remote monitoring system may send, present, or upload an output continuously, on condition, or on demand of a user. When sent or presented, the output may reflect or show updated information and recently collected data.

According to some embodiments, the format and sophistication of the presentation of the output will likely depend on the intended recipient(s) or user(s). For example, an output, which may include any relevant information, data, analysis, results, reports, etc., about the operation of a water treatment system or the quality, properties, etc., of water processed or treated by the water treatment system, may be presented in a more sophisticated form when presented to internal management or operators of the water treatment system than when presented to elected officials, customers, or members of the public.

According to embodiments of the present invention, one or more output(s) may be sent, presented, or uploaded to one or more remote viewing device(s) in one or more formats having different sophistication or complexity based on their intended recipient(s) or user(s), even if such one or more output(s) relates to the same data or information. According to some embodiments, an output, such as an analysis result or analysis report about current data may be presented alongside and/or in comparison to historical records. An output may also be used to present scheduled and predicted maintenance reports. For example, the output may provide or present preconfigured performance information, maintenance, quality assurance, quality control, regulatory, cost reports, performance evaluation, graphing, historical trends, regulatory reports plant or facility process, operating and economic information, indications and scheduling for preventative maintenance, troubleshooting, etc. According to some embodiments, access to an output of the present remote monitoring system may depend on the security measures in place, such as a login and password or other identifying criteria.

According to some embodiments, the output may be used to report or present information or analysis of the operation or conditions in a waste water treatment plant (WWTP) particularly as it relates to health and safety concerns. The analysis result may take many different forms; however, one form may be a prediction of the water composition and flow rate in terms of selected parameters of interest that may arrive at a WWTP as a function of time. Thus, for example, the remote computer may be operable to calculate a predicted concentration of various components at the time of their arrival at a central WWTP and compare the computed values with pre-established and/or historical parameters.

According to some embodiments, the output may be a report submitted to a regulatory agency in a required format, such as visual graphs, statistical reports, or a compliance calendar, to meet the reporting requirements of the agency, and such reporting or sending of the output may be performed automatically. Quality and safety standards for potable water are regulated by the Environmental Protection Agency (EPA) in accordance with the Public Water System Supervision program. The standards are enforced by local agencies. There are over 170,000 water districts in the United States which provide public drinking water to 90% of Americans. The EPA has primary standards designed to protect public health against substances that may be harmful to humans if consumed. EPA secondary standards ensure that aesthetic qualities of water, such as taste, odor, or clarity, are met. However, each water district remains responsible for monitoring the drinking water itself to ensure that it meets all drinking water standards. The treatment processes for the drinking water must be monitored as well. Therefore, the remote monitoring system of the present invention may be useful in not only monitoring whether these standards are met on a routine and continuous basis, but also providing automatic generation of regulatory reports as an output to an agency in the required format.

According to some embodiments, the remote monitoring system of the present invention may automatically prepare the documentation required to meet the regulatory requirements. Such documentation may be printed out and mailed or transmitted by a suitable mode of communication, such as by facsimile, ftp, or email, to the regulatory agency, thereby reducing or eliminating the opportunity for human error and/or unwanted manipulation. In order to comply with the regulatory testing calendar, water districts are generally required to report a list of analytical test results varying from hourly to yearly, depending on the source of the water supply. Monitoring schedules may differ according to the type of contaminants that may be present in a given water supply. The hourly tests may typically include chlorine and turbidity, which may be measured or collected automatically.

According to some embodiments, the output of the remote monitoring system may be a regulatory report sent to the department of Homeland Security and/or law enforcement agencies in situations appearing to suggest deliberate tampering of a water treatment system, such as by an act of terrorism. Embodiments of the present invention may be able to carry out sophisticated calculations, manipulations, analysis, etc. to detect tampering events and perhaps distinguish those events from normal malfunction or mismanagement.

According to embodiments of the present invention, the output may be in any format and may incorporate a tabular or graphical display as may be suitable to facilitate or focus the presentation of the data or analysis or manipulation of the data for a particular user(s). According to some embodiments, the output of the remote monitoring system may be a simplified presentation for a non-technical user that is untrained or lacks detailed knowledge about the operation of a water treatment system, such as a customer, elected official, or member of the public. For example, municipal water treatment plants are ultimately the responsibility of elected officials. Yet these officials rarely have the technical training or time to allow them directly access the performance parameters of the systems for which they are responsible. Embodiments of the present invention may easily be used to provide a readily understandable presentation output of the current performance of a municipal water treatment system. Such an output may be made accessible to the public, such as via the Internet by uploading onto a web page, thus allowing interested members of the public to monitor the operation of their own drinking water plants as desired. In providing a simplified presentation of the data to the non-technical user, operating parameters may be color coded and displayed graphically or in a tabular format, etc.

However, according to some embodiments, a simplified presentation of the data in an output of the remote monitoring system may be beneficial to even a trained operator or manager of a water treatment system. Accordingly, a graphical and/or color coded presentation of the data or analysis or manipulation of the data may potentially be used in any output format or report. A graphical presentation may include any suitable graphical format, such as tables, pie charts, bar graphs, etc., that may aid the presentation of the output or report. Color coding may be used, for example, to provide an indication of normal or abnormal operation, as well as warning status or alarm conditions. An output of the remote monitoring system may also show data or analysis or manipulation of the data in a geographical layout or form to help track or pinpoint the origin or cause of a problem. Historical data or expected values may also be shown with current data for comparison. When an output is provided to a trained user, such as a manager or operator of a water treatment system, the data and/or analysis may be presented as an exception report showing all instances where data triggered an alarm or were close to a trigger point.

According to embodiments where an output is sent or presented to management, the outputs or reports may be typically generated for three primary management levels: (A) Process systems operations, (B) Plant quality assurance (QA)/quality control (QC), and (C) financial oversight. For instance, an output or report for operations of a process system may contain information necessary to monitor, maintain, supervise, and trouble shoot process plant system performance. In this manner, typical information and parameters may include, if applicable, flow rates, pressures, delta pressures, permeate and/or ion exchange quality, pH, alarm conditions, tank levels, and a graphical presentation of applicable process performance parameters and trends.

A Plant QA/QC output or report, for example, may contain information necessary to enable plant managers to effectively manage downstream manufacturing or distribution processes. In addition, quality assurance personnel may be able to monitor the quality and quantity of the treated water to confirm compliance with specifications and standards. Information in this report may typically include treated water production rate (flow), treated water consumption rate (flow), treated water storage volume, reserve capacity (at current production and consumption rates), final treated water quality, reports and archive data for regulatory compliance and/or QA/QC documentation.

Financial oversight may be achieved with a plant economic output or report which may contain information needed by managers with profit and loss or budget responsibility to effectively track the cost of operation and to identify budget variances, when they occur, to permit timely corrective action. For this purpose, typical information parameters contained in a plant economic report may include calculated power consumption (expressed in kWh and actual cost in local currency) and computed on the basis of user's supply pump/motor efficiencies both as a year to date, as a percent of the prior period, and variances both actual and budget/actual versus prior period. The parameter may also include calculated chemical consumption (expressed in volume consumption and as converted to local currency) and computed based on the user's supplied chemical dose rates and integrated feed water flow rates. This may be performed as a year to date, as a percent of the prior period, or as variances both actual versus budget/actual versus prior period.

According to embodiments of the present invention, an output including data, analysis, results, analysis reports, etc., may be sent to a remote viewing device using any appropriate or suitable mode of communication known in the art. The output may be in any suitable file format, such as but not limited to: html, jpeg, gif, pdf, etc., based on the output type and/or remote viewing device. The output may be sent in a suitable and/or tailored format to preselected recipients, such as authorized personnel or operators of a water treatment system, law enforcement, and/or regulatory agencies, in the event of an emergency or abnormal conditions or operation. The content of the output may be kept confidential, and access to the output including data, analysis, results, analysis reports, etc., may be controlled by encryption or the use of appropriate account names, protocols and passwords. Multiple parties or persons may be notified, access, or receive outputs from the remote monitoring system, thus allowing redundancy in sending notifications, alarms, analysis results, analysis reports, etc.

According to some embodiments, the mode of communication for sending an output to, or allowing access to an output by, a remote viewing device may vary and may use any suitable technology. For example, according to some embodiments, an output including data, analysis results, analysis reports, etc., may be uploaded to an Internet or web server for access, visualization, or downloading by a remote viewing device, such as by using a web browser. According to some embodiments, the Internet or web server may be the remote computer of the remote monitoring system or a separate computer or server. According to some embodiments, the output may be uploaded to an Internet or web server for access with little or no manipulation or analysis by the remote computer, visualization, or downloading by a remote viewing device by a user. According to these embodiments, for example, the data or information derived from the one or more sensors may first be analyzed or manipulated by the local computer prior to being transmitted to the remote computer. By making the output available on an Internet web server, the communication or dispersion of the output, including data, analysis results, analysis reports, alerts, alarms, etc., may be greatly facilitated and may involve any interested or authorized recipients. For example, any authorized recipients may access data, analysis results, analysis reports, alerts, alarms, etc., of the output on a webpage by accessing the data, information, output, etc. asynchronously from the Internet server computer. Furthermore, the output, including data, analysis, results, analysis reports, alerts, alarms, etc., may be continuously or regularly updated and made available in near real time.

According to some embodiments, the mode of communication for sending an output to, or allowing access to an output by, a remote viewing device may include other suitable technologies, such as, for example, by facsimile, file transfer protocol (FTP), voice or text messaging, text to voice telephone messages, electronic mail, pager, human voice calling, SMS messages, instant messaging or groupware protocols, or other messaging medium which can be mediated by a computer program connected to a phone line, public switched telephone network (e.g. via telefax), the Internet, a cellular network, wireless or satellite communication, radio communication, etc. See description above for additional examples of a mode of communication. Examples of remote viewing devices that may be used with embodiments of the present invention may include, for example, personal computers, servers, etc., as well as a variety of personal communications equipment, such as PDAs, cell phones, pagers, Blackberrys®, Palm® devices, iPhones®, etc. According to some embodiments, the remote viewing device may be the same as the remote computer of the present remote monitoring system.

One advantage of embodiments of the present invention, is that remote storage and manipulation of water quality and treatment data may make the operation of a water treatment system safer and less susceptible to tampering or control by unauthorized individuals or outsiders by separating the operation and control of the water treatment system from the data analysis, manipulation, and/or communicating or reporting functions of the present invention. For example, this feature may be useful in detecting direct tampering, such as an act of terrorism, by an individual or outsider on a water treatment system. According to embodiments of the present invention, since the remote computer of the remote monitoring system is physically separated from the operation of the water treatment system, it is unlikely that an individual tampering with a water treatment system would also have access to the remote monitoring system of the present invention, especially since access to the remote monitoring system may be controlled or password protected. According to these embodiments, if a hacker were to remotely access the remote monitoring system of the present invention, they would not be able to directly access and control the operation of the water treatment system because the remote computer and database is external, physically remote, and not connected to the process facility being monitored except perhaps via a mode of transmission.

Another advantage of embodiments of the present invention, for example, is that the ability to send an output or other data, information, etc., about the operation of a water treatment system to a remote viewing device via a mode of communication may reduce the need for operators or authorized personnel to visit the sites of the water treatment system being monitored, maintained, etc. This may reduce the costs associated with monitoring a water treatment system if data had to be collected locally or by direct connection to a device or local computer. This is especially true if the remote monitoring system is further combined with sensors and other devices that require less maintenance and service, such as sensors that do not contact the water and are able to operate reliably for longer periods of time without maintenance or service.

Another advantage of embodiments of the present invention is that the remote monitoring system of the present invention may create a layer of redundancy that may be independent of and/or complementary to the direct monitoring carried out by qualified individuals at a water treatment system or facility to safeguard operation of the water treatment system. Redundancy may also be achieved by, perhaps simultaneously, reporting analyzed or manipulated data to multiple persons and/or entities in the same or different format(s). In addition, the remote monitoring system may reduce or eliminate the need for direct human involvement. By having the remote monitoring system automatically perform the calculations and manipulations on the raw data in real time without direct human involvement, there may be less human error in evaluating, analyzing, etc., water quality and the operation of the water treatment system.

Yet another advantage of embodiments of the present invention is that data and information may be combined, pooled, compiled, etc., from sensors placed at multiple location(s) or site(s) throughout a water treatment system and in the field as part of a broader distribution or collection system. According to some embodiments, sites or locations within the distribution or collection system may be considered part of the water treatment system even though the distribution or collection system may operate independently of a water treatment core facility of the water treatment system. Such sensors located at the multiple location(s) or site(s) may operate independently and/or have no communication between sensors other than the remote monitoring system of the present invention. By comparing data from these multiple independent sites or locations, a more advanced form of analysis and conclusions may be performed or made in view of the water treatment and distribution systems as a whole. For example, better prediction and anticipation of downstream contamination events may be made by having multiple data points obtained from sites or locations throughout a collection or distribution system associated with the water treatment system, thus allowing appropriate actions to be taken downstream to lessen or prevent the impact or damage caused by the contamination event, such as the introduction of dangerous, poisonous or unhealthful contaminants into the environment or drinking water.

For example, the water treatment core facility may be a central wastewater treatment plant (WWTP) that receives waste released from multiple sources upstream that converge into a common collection system that feeds into the central WWTP. The collection system may serve numerous waste water treatment sites or industrial waste sites that feed into a central WWTP. According to embodiments of the present invention, multiple sensors may be placed throughout a collection system including the water treatment and industrial waste sites to monitor discharge into the common collection system. Water treatment sites may include cities, manufacturers, agricultural operations, etc., which treat waste water before it is discharged into the common collection system. For a WWTP operator, an accurate prediction of the composition of incoming waste water would be highly beneficial for the efficient operation of the WWTP facility.

According to embodiments of the present invention, the composition of influx water in a WWTP serving a geographically distributed waste water collection system may be estimated from measurements taken from sensors located upstream, such as at or near waste water treatment site(s) or industrial waste site(s) discharging into the common collection system. Since the water flow patterns, transit times, and the composition of water leaving each of the treatment or industrial sites within the waste water collection system may be known, the expected composition of influx water arriving at the WWTP can be calculated and reliably and quickly transmitted to the operators of the central WWTP and/or remotely to other entities or persons, such as through a remote viewing device. In addition to known information, the volumetric flow rate may be measured using the one or more sensors. This advance notice allows the WWTP to respond to varying contaminant or pollutant introductions in a far more effective manner than at present, where the first knowledge or information may come after the contaminants have already entered or even passed through the system. For WWTP entities that operate reclamation facilities downstream of the WWTP, this advance knowledge is even more valuable as it allows the reclamation facility to modify its operations as necessary to prevent damage to the process facilities. It will be readily appreciated by WWTP operators that knowledge of the incoming waste water composition would be of great benefit in assuring the continued operation of the central facility at top efficiency.

Another advantage of embodiments of the present invention is that the cause, scope, or location of a problem or source of contamination may be better determined, tracked or distinguished by having more independent data points of reference obtained from sensors at sites or locations throughout a water treatment system, such as sites or locations in a water treatment core facility as well as throughout a collection or distribution system, i.e., in the field. Such analysis or determinations may be aided by the existence of historical data and known information about the operation of the water treatment system in relation to its environment which may be used for comparison. For example, a chemically or biologically active agent may be deliberately injected into the distribution system at a point downstream of a potable drinking water treatment facility. A sophisticated terrorist might first inject a chlorine scavenger, such as sodium metabisulfite, into the distribution system to eliminate the residual chlorine normally present. At some point downstream of the metabisulfite injection point, the chemical or biological agent could be injected into the water without destruction by any residual disinfectant. Without a remote monitoring system in place with sensors in the distribution system, such contamination could go undetected for quite some time, allowing a thorough infiltration of a biological or chemical agent throughout the distribution system. By contrast, the remote monitoring system could detect that the residual chlorine at the sensor had diminished to zero and sound the alarm. Especially with historical data available for comparison, the remote monitoring system would be able to reduce the incidence of false terrorist attack alarms because data obtained from sensors at the treatment facility and in the distribution system could be compared. For example, a chlorine-dosing equipment failure might be determined and distinguished from a terrorist attack if a fall in chlorine concentration is observed at both the water treatment plant and at points in the distribution system.

Another possible advantage of embodiments of the present invention is that the data may be transmitted to a remote computer where more advanced computations, manipulations, analysis, etc., may be performed prior to reporting, uploading, etc., of an output, such as an analysis result, analysis report, or alarm to a user. A software program on the remote computer may be more sophisticated than may be achieved locally, such as with the local electronic control systems used to control and operate the water treatment system, plant, or facility. This may allow for the processing power of existing control systems to not be impaired or impacted. For example, an analysis report generated by manipulation of the data on a remote computer may include a submission to a regulatory agency to meet reporting requirements in the format required by the agency, and such reporting may be performed automatically. The remote analysis, manipulation, etc., may be performed quickly and automatically to remotely monitor operation and water conditions in real time, continuously, at selected, periodic, or regular intervals, on condition, or upon demand of a user and rapidly generate multiple types of outputs, such as alarms, analysis results, analysis reports, etc., to one or more users. For example, the software program may separately generate a detailed regulatory report for submission to a regulatory agency, send a simple alarm to authorized personnel to alert of a contamination or equipment failure, and/or post data and information about the water treatment system on a web page for access by a member of a public. Alternatively, the analysis, manipulation, etc., of data and information may be performed locally on the local computer, such as a logger device. According to some embodiments, such analysis, manipulation, etc., of data and information on the local computer may be performed in addition to further analysis, manipulation, etc., of data and information on the remote computer.

Yet another advantage of embodiments of the present invention is that greater flexibility and accessibility may be achieved over existing systems allowing access to the remote computer to receive data, information, reports, etc., sent by any known means or mode of communication from the remote computer. By having greater accessibility and communication of data, information, reports, etc., greater coordination may be achieved between different parts of the water treatment system and any associated collection or distribution system, which may include, for example, remote sites or locations of industrial waste discharge in the case of a WWTP.

Yet another advantage of embodiments of the present invention is that the remote monitoring system may be implemented with moderate cost since the remote monitoring system may be incorporated or interfaced with existing sensors and/or an electronic control system of a water treatment system without modification of the design or layout of the water treatment system. Furthermore, the data collected from the water treatment system may be transmitted electronically to the remote computer using, for example, existing communication networks.

Figure 5:
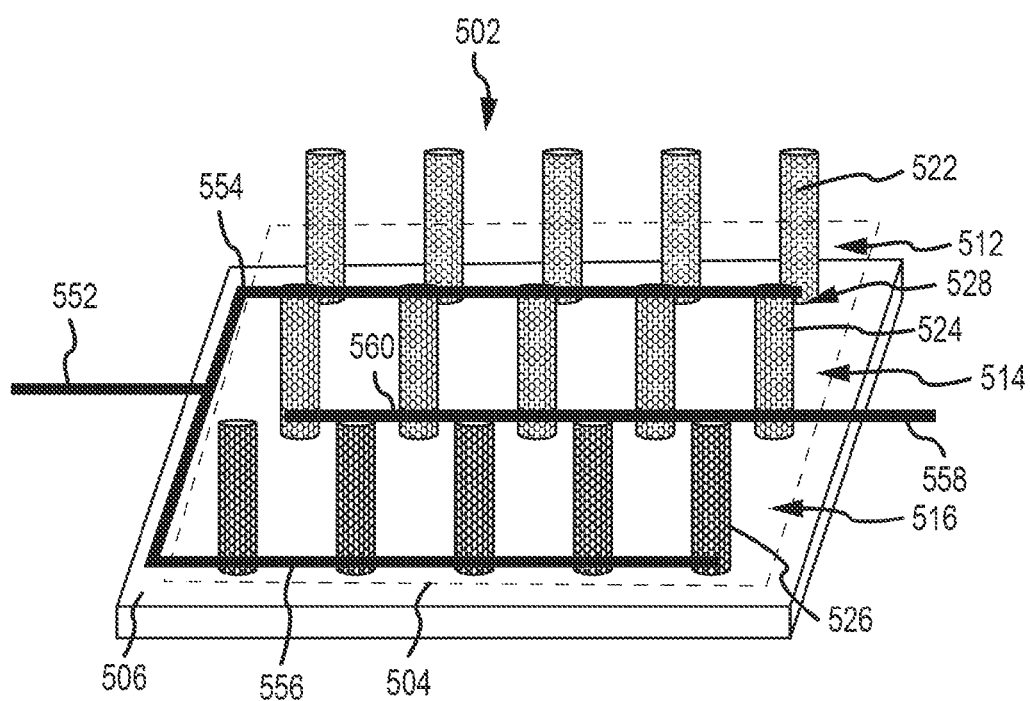
FIG. 5 is a perspective view in simplified form of a working electrode of a sensor device comprising an array of carbon nanotubes in accordance with one embodiment of the present invention.

In one embodiment, the present invention employs one or more arrays of carbon nanotubes that each function as a separate working electrode of a sensor device. FIG. 5 shows a working electrode 502 comprising an array 504 of carbon nanotubes on a substrate 506 according to one embodiment of the present invention. Array 504 includes rows 512, 514 and 514 of carbon nanotubes 522, 524 and 526, respectively. Carbon nanotubes 522, 524 and 526 are each bound at one end 528 to substrate 506. FIG. 5 also shows an electrical connection 552 connected to carbon nanotubes 522 of row 512 by a lead 554 and connected to carbon nanotubes 526 of row 516 by lead 556. An electrical connection 558 is connected to carbon nanotubes 524 of row 514 by a lead 560. Leads 554, 556 and 560 may be mounted in or on substrate 506. Leads 552, 554 and 560 may be part of a printed circuit board on which substrate 506 is mounted. Electrical connections 552 and 558 may be connected to other electronic devices of the sensor such a power supply, a reading apparatus, etc. depending on the function desired for each row of nanotubes.

Although only three rows of nanotubes are shown in FIG. 5 for simplicity of illustration, an array of nanotubes of the present invention may have any number of rows.

In one embodiment, in which the carbon nanotubes of each row of array 504 have different functionalities, each carbon nanotube 522 of row 512 has a first functionality. Each carbon nanotube 524 of row 514 has a second functionality that is different from the first functionality. Each carbon nanotube 526 of row 516 has a third functionality that is different from the first and second functionality. The functionality of the carbon nanotubes of one of the rows 512, 514 and 516 may be that the carbon nanotubes are non-functionalized. Each row of carbon nanotubes may then function as a sensor with the analyte sensed by carbon nanotubes 522, 524 and 526 of rows 512, 514 and 516, respectively, being dependent on the functionality of the carbon nanotubes in the respective row. In this embodiment, electrical connections 552 and 558 would each be connected to a respective reading device.

In other embodiments, one or more of the rows of nanotubes of the array of nanotubes may function as anode(s) that produce protons that affect the pH environment for the other rows of nanotubes that function as sensors for one or more analytes. For example, carbon nanotubes 524 could function as anodes, and carbon nanotubes 522 and 526 could function as sensors for an analyte. The electrical connection 558 could pull a voltage that causes carbon nanotubes 524 of row 514 to generate protons. As the amount of voltage pulled on carbon nanotubes 524 of row 514 increased, the effect of increasing pH can be observed by the concentration and/or amount of analyte sensed by carbon nanotubes 522 and 526 of rows 512 and 516.

If carbon nanotubes 522 and 526 each had their own electrical connection instead of a shared electrical connection, carbon nanotubes 522 and 526 of rows 512 and 516 could be used as sensors for different analytes by using nanotubes with different functionalities for rows 512 and 516, respectively.

In other embodiments, alternating rows of carbon nanotubes may be function as cathodes and anodes, to reduce and oxidize an analyte respectively, thereby allowing an analyte to be both sensed and regenerated. For example, electrical connection 552 could be used to drive a reduction reaction on carbon nanotubes 522 and 526 of rows 512 and 516, respectively and electrical connection 558 could be used to drive an oxidation reaction on carbon nanotubes 524 of row 514.

Depending on the particular analyte being sensed, carbon nanotubes 522 and 526 could function as sensors or carbon nanotubes 524 could function as sensors.

Although only three rows of carbon nanotubes are shown in FIG. 5, the present invention envisions that there may be any number of rows of carbon nanotubes in which alternating rows are driven to produce reduction reactions and oxidation reactions.

Although in the embodiment of the invention shown in FIG. 5 there is only one lead for each rows of carbon nanotubes, in other embodiments there could be an electrical lead for each carbon nanotube. In some embodiment, there may even been one electrical connection per nanotube.

Figure 6:
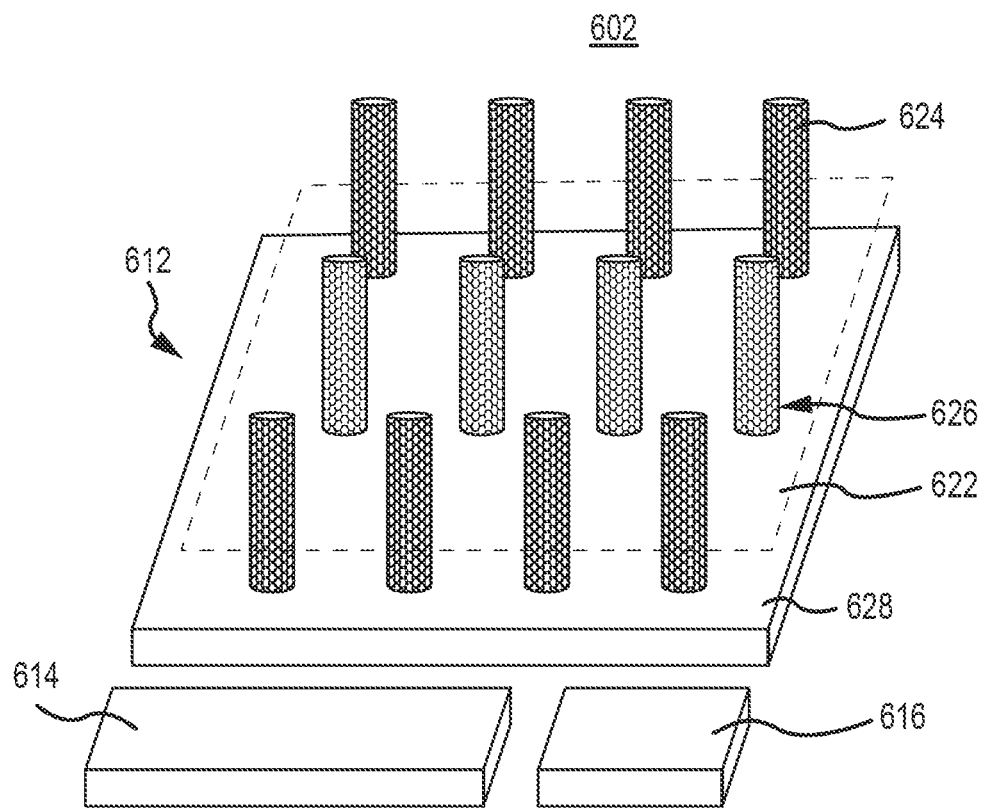
FIG. 6 is a perspective view in simplified form of an electrode cell assembly in accordance with one embodiment of the present invention.

FIG. 6 shows an electrode cell assembly 602 according to one embodiment of the present invention comprising a working electrode 612, a counter electrode 614 and a reference electrode 616. Working electrode 612 comprises an array 622 of carbon nanotubes 624 that are bound at one end 626 to a substrate 628. Each carbon nanotube 624 has the same functionality.

FIG. 7 shows a working electrode 702 according to one embodiment of the present invention comprising a square array 712 of carbon nanotubes 714 mounted on a substrate 716. Each carbon nanotube 714 has the same functionality.

A working electrode assembly comprising multiple working electrodes each made of an array of carbon nanotubes may have various configurations.

FIG. 8 shows a working electrode assembly 802 according to one embodiment of the present invention comprising two rectangular arrays 812 and 814 of carbon nanotubes 822 and 824, respectively, mounted on a substrate 826. Arrays 812 and 814 each function as a separate working electrode. Carbon nanotubes 822 have a first functionality. Carbon nanotubes 824 have a second functionality that is different than the functionality of carbon nanotubes 822.

FIG. 9 shows a working electrode assembly 902 according to one embodiment of the present invention having a substrate 904 on which is mounted a counter electrode 906. Working electrode comprises four square arrays 912, 914, 916 and 918 of carbon nanotubes 922, 924, 926 and 928, respectively, mounted on substrate 904. Arrays 912, 914, 916 and 918 each function as a separate working electrode. Carbon nanotubes 922 have a first functionality. Carbon nanotubes 924 have a second functionality. Carbon nanotubes 926 having a third functionality. Carbon nanotubes 928 have a fourth functionality. The first, second, third and fourth functionalities may all be different or two or more of the functionalities may be the same.

FIG. 10 shows a working electrode assembly 1002 according to one embodiment of the present invention comprising nine square arrays 1012, 1014, 1016, 1018, 1020, 1022, 1024, 1026 and 1028 of nanotubes 1032, 1034, 1036, 1038, 1040, 1042, 1044, 1046 and 1048, respectively, mounted on a substrate 1050. Arrays 1012, 1014, 1016, 1018, 1020, 1022, 1024, 1026 and 1028 each function as a separate working electrode. Carbon nanotubes 1032 have a first functionality. Carbon nanotubes 1034 have a second functionality. Carbon nanotubes 1036 having a third functionality. Carbon nanotubes 1038 have a fourth functionality. Carbon nanotubes 1040 have a fifth functionality. Carbon nanotubes 1042 have a sixth functionality. Carbon nanotubes 1044 have a seventh functionality. Carbon nanotubes 1046 having an eighth functionality. Carbon nanotubes 1038 have a ninth functionality. The first, second, third, fourth, fifth, sixth, seventh, eight and night functionalities may all be different or two or more of the functionalities may be the same.

FIG. 11 shows a working electrode assembly 1102 according to one embodiment of the present invention comprising two rectangular arrays 1112 and 1114 of carbon nanotubes 1122 and 1124, respectively, mounted on a substrate 1126. Arrays 1112 and 1114 each function as a separate working electrode. Carbon nanotubes 822 and 824 have the same functionality. Rectangular arrays 1112 and 1114 have different properties as sensors due to being in different electrical environments 1132 and 1134, respectively, shown by dashed boxes. For example, carbon nanotubes 1122 may be in a reducing environment and carbon nanotubes 1124 may be in an oxidizing environment due to electrical currents applied to or withdrawn from carbon nanotubes 1122 and 1124 respectively by electrical connections (not shown in FIG. 11).

Figure 12:
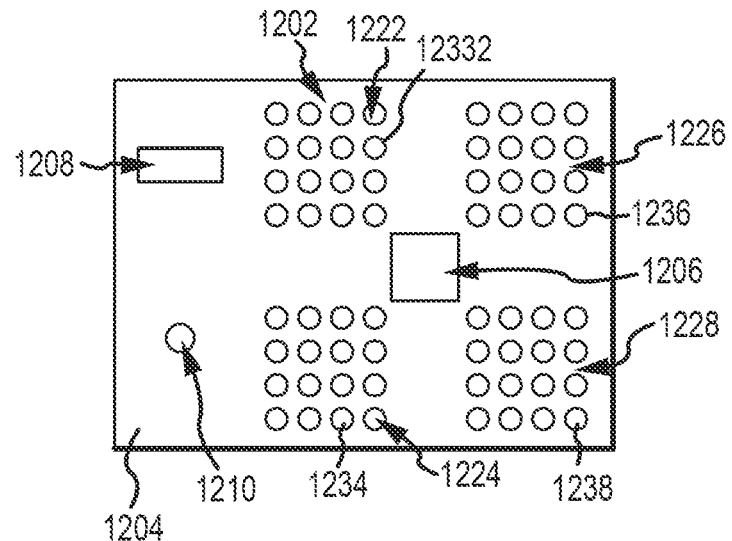
FIG. 12 is a top plan view in simplified form of an electrode cell assembly in accordance with one embodiment of the present invention.

FIG. 12 shows an electrode cell assembly 1202 according to one embodiment of the present invention having a substrate 1204 on which is mounted a counter electrode 1206, a pressure sensor 1208 and a reference electrode 1210. Electrode cell assembly 1202 comprises four square arrays 1222, 1224, 1226 and 1228 of carbon nanotubes 1232, 1234, 1236 and 1238, respectively, mounted on substrate 1204. Arrays 1222, 1224, 1226 and 1228 each function as a separate working electrode. Carbon nanotubes 1232 have a first functionality. Carbon nanotubes 1234 have a second functionality. Carbon nanotubes 1236 having a third functionality. Carbon nanotubes 1238 have a fourth functionality. The first, second, third and fourth functionalities may all be different or two or more of the functionalities may be the same.

Figure 13:
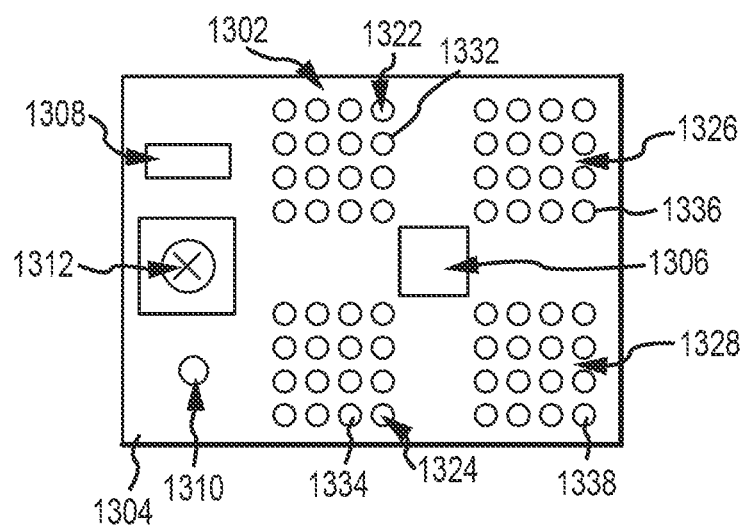
FIG. 13 is a top plan view in simplified form of an electrode cell assembly in accordance with one embodiment of the present invention.

FIG. 13 shows an electrode cell assembly 1302 according to one embodiment of the present invention having a substrate 1304 on which is mounted a counter electrode 1306, a pressure sensor 1308, a reference electrode 1310 and a flow sensor 1312. Electrode cell assembly 1302 comprises four square arrays 1322, 1324, 1326 and 1328 of carbon nanotubes 1332, 1334, 1336 and 1338, respectively, mounted on substrate 1304. Arrays 1322, 1324, 1326 and 1328 each function as a separate working electrode. Carbon nanotubes 1332 have a first functionality. Carbon nanotubes 1334 have a second functionality. Carbon nanotubes 1336 having a third functionality. Carbon nanotubes 1338 have a fourth functionality. The first, second, third and fourth functionalities may all be different or two or more of the functionalities may be the same.

Figure 14:
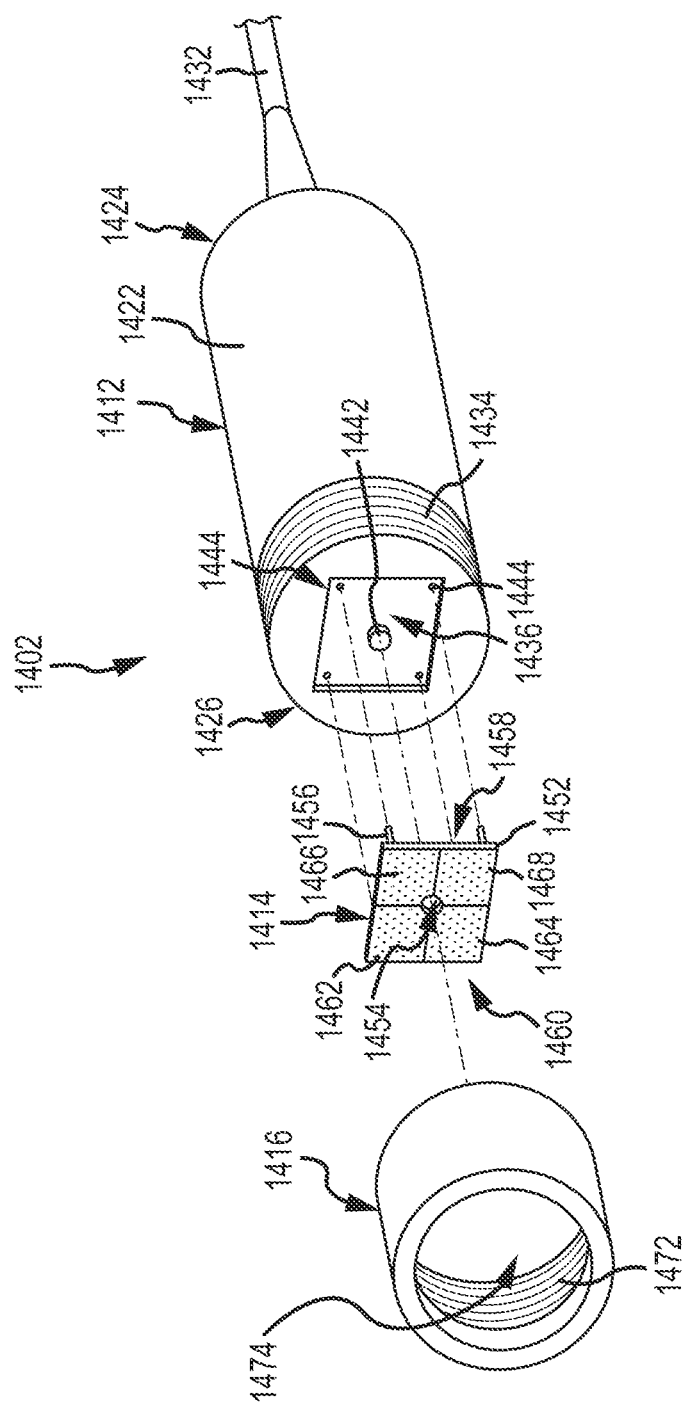
FIG. 14 is a perspective view of a sensor device in accordance with one embodiment of the present invention.

FIG. 14 shows a sensor device 1402 of the present invention comprising a sensor base 1412, a working electrode assembly 1414 and a counter electrode 1416. Sensor base 1412 includes a cylindrical body 1422 made of an insulating material such as plastic, a sensor base proximal end 1424 and a sensor base distal end 1426. Connected to sensor base proximal end 1424 is an electrical connection 1432 that connects sensor base 1412 to a monitoring device (not shown in FIG. 14). Cylindrical body 1422 includes a metal exterior screw thread contact 1434 Exterior screw thread contact 1434 is in electrical communication with a wire (not shown) that extends through cylindrical body 1422 and is connected with respective wires (not show) in electrical connection 1432. Sensor base distal end 1426 includes a square-shaped recess 1436. Mounted in square-shaped recess 1436 is a round reference electrode 1442 that is made of a conductive material such as a metal and is in electrical communication with a wire (not shown) that extends through cylindrical body 1422 and is connected with respective wires (not shown) in electrical connection 1432. Square-shaped recess 1438 includes four pin contact receptacles 1444 that include receptacle contacts (not shown) are in electrical communication with wires (not shown) that extend through cylindrical body 1422 and are connected with respective wires (not show) in electrical connection 1432.

Working electrode assembly 1414 includes a square-shaped working electrode assembly base 1452 having a circular opening 1454 and four pin contacts 1456 (only two of which are visible in FIG. 14) extending perpendicularly from a proximal side 1458 of working electrode base 1452. On a distal side 1460 of working electrode assembly base 1452 are four arrays of carbon nanotubes: array 1462, array 1464, array 1466 and array 1468. Arrays 1462, 1464, 1466 and 1468 each function as a separate working electrode. The carbon nanotubes in each array of carbon nanotubes are bound to working electrode assembly base 1452 at one end and are in electrical communication with a respective pin contact 1456. Working electrode assembly 1414 is mounted in square-shaped recess 1436 to that pin contacts 1456 are received by pin contact receptacles 1444 so that each pin contacts 1456 contacts a respective receptacle contact. When working electrode assembly 1414 is mounted in square-shaped recess 1436, reference electrode 1442 extends through circular opening 1454 of working electrode assembly 1414. Counter electrode 1416 is made of a conductive material such as a metal and is ring-shaped. Counter electrode includes a interior screw thread 1472 that may be used to screw counter electrode onto exterior screw thread contact 1434 thereby making electrical contact been counter electrode 1416 and exterior screw thread contact 1434. An opening 1474 in counter electrode 1416 allows a water sample containing one or more analytes of interest to contact working electrode assembly 1414 and reference electrode 1442 when sensor device 1402 is immersed in a water sample. The carbon nanotubes of array 1462 have a first functionality. The carbon nanotubes of array 1464 have a second functionality. The carbon nanotubes of array 1466 have a third functionality. The carbon nanotubes of array 1468 have a fourth functionality. The first, second, third and fourth functionalities may all be different or two or more of the functionalities may be the same.

Figure 15:
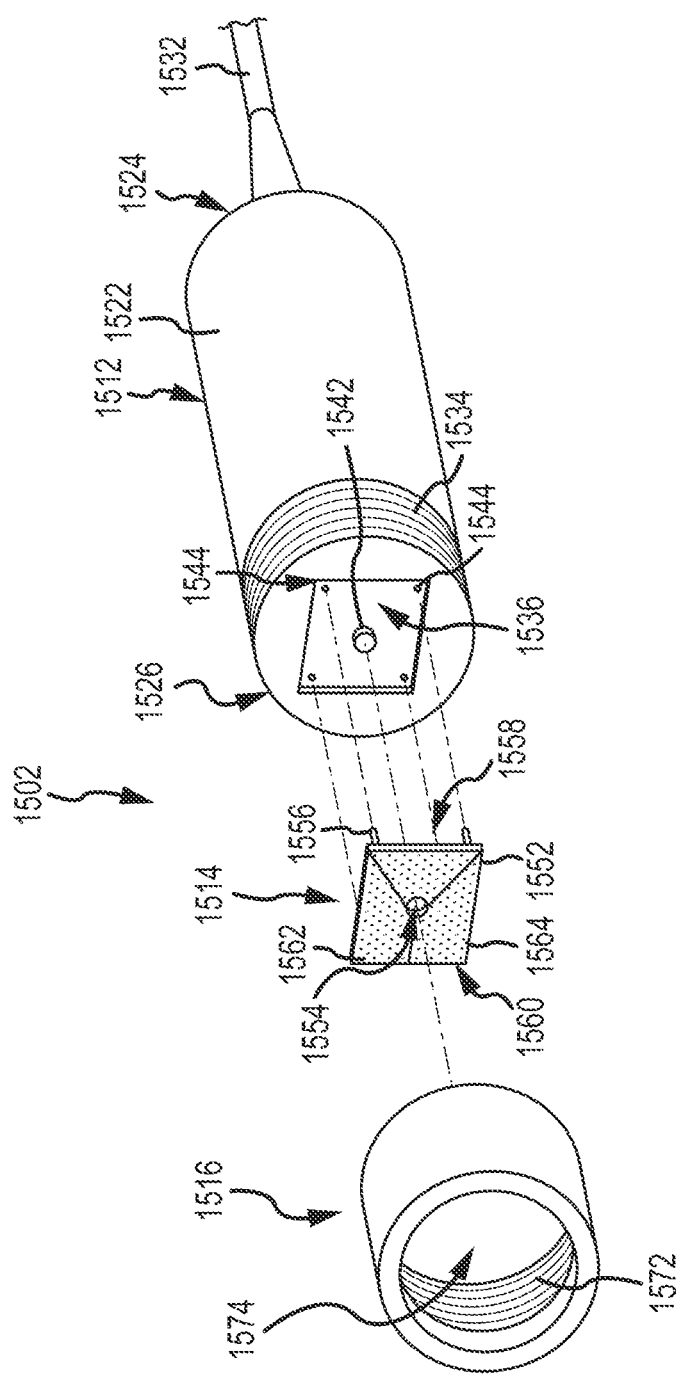
FIG. 15 is a perspective view of a sensor device in accordance with one embodiment of the present invention.

FIG. 15 shows a sensor device 1502 of the present invention comprising a sensor base 1512, a working electrode assembly 1514 and a counter electrode 1516. Sensor base 1512 includes a cylindrical body 1522 made of an insulating material such as plastic, a sensor base proximal end 1524 and a sensor base distal end 1526. Connected to sensor base proximal end 1524 is an electrical connection 1532 that connects sensor base 1512 to a monitoring device (not shown in FIG. 15). Cylindrical body 1522 includes a metal exterior screw thread contact 1534 Exterior screw thread contact 1534 is in electrical communication with a wire (not shown) that extends through cylindrical body 1522 and is connected with respective wires (not show) in electrical connection 1532. Sensor base distal end 1526 includes a square-shaped recess 1536. Mounted in square-shaped recess 1536 is a round reference electrode 1542 that is made of a conductive material such as a metal and is in electrical communication with a wire (not shown) that extends through cylindrical body 1522 and is connected with respective wires (not shown) in electrical connection 1532. Square-shaped recess 1538 includes four pin contact receptacles 1544 that include receptacle contacts (not shown) are in electrical communication with wires (not shown) that extend through cylindrical body 1522 and are connected with respective wires (not show) in electrical connection 1532.

Working electrode assembly 1514 includes a square-shaped working electrode assembly base 1552 having a circular opening 1554 and four pin contacts 1556 (only two of which are visible in FIG. 15) extending perpendicularly from a proximal side 1558 of working electrode assembly base 1552. On a distal side 1560 of working electrode assembly base 1552 are four arrays of carbon nanotubes: array 1562, array 1564 and array 1566. Arrays 1562, 1564 and 1566 each function as a separate working electrode. The carbon nanotubes in each array of carbon nanotubes are bound to working electrode assembly base 1552 at one end and are in electrical communication with a respective pin contact 1556. Working electrode assembly 1514 is mounted in square-shaped recess 1536 to that pin contacts 1556 are received by pin contact receptacles 1544 so that each pin contacts 1556 contacts a respective receptacle contact. When working electrode assembly 1514 is mounted in square-shaped recess 1536, reference electrode 1542 extends through circular opening 1554 of working electrode assembly 1514. Counter electrode 1516 is made of a conductive material such as a metal and is ring-shaped. Counter electrode 1516 includes a interior screw thread 1572 that may be used to screw counter electrode onto exterior screw thread contact 1534 thereby making electrical contact been counter electrode 1516 and exterior screw thread contact 1534. An opening 1574 in counter electrode 1516 allows a water sample containing one or more analytes of interest to contact working electrode assembly 1514 and reference electrode 1542 when sensor device 1502 is immersed in a water sample. The carbon nanotubes of array 1562 have a first functionality. The carbon nanotubes of array 1564 have a second functionality. The carbon nanotubes of array 1566 have a third functionality. The first, second and third functionalities may all be different or two or more of the functionalities may be the same.

In FIGS. 14 and 15 the working electrode assembly may be held in place in the square-shaped recess of the sensor base by using an adhesive for by providing engaging structures on the working electrode assembly base and/or on the edges of the square-shaped recess so that the working electrode assembly may be snap-fitted into place. Also, although the working electrode assemblies of FIGS. 14 and 15 have four and three arrays of carbon nanotubes, respectively, a working electrode assembly may have any number of arrays of carbon nanotubes.

Figure 16:
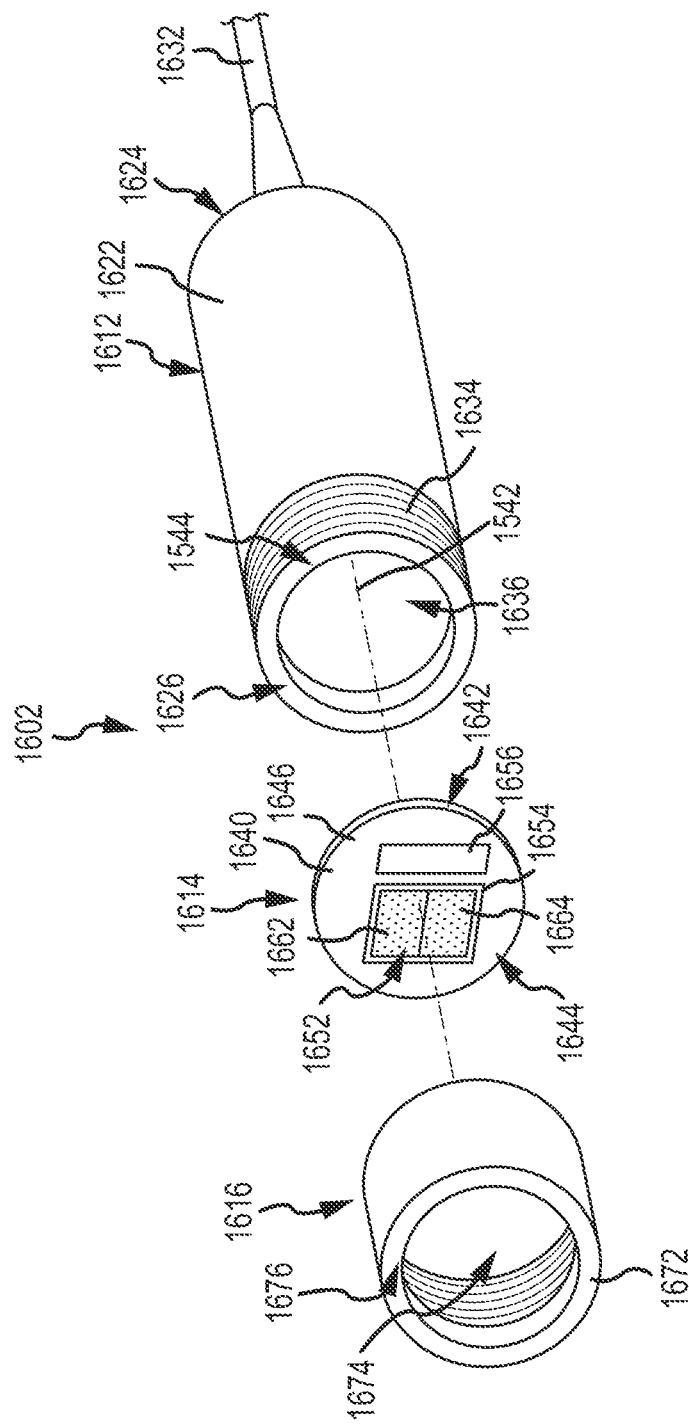
FIG. 16 is a perspective view of a sensor device in accordance with one embodiment of the present invention.

FIG. 16 shows a sensor device 1602 of the present invention comprising a sensor base 1612, an electrode cell assembly 1614 and a ring-shaped cap 1616. Sensor base 1612 includes a cylindrical body 1622 made of an insulating material such as plastic, a sensor base proximal end 1624 and a sensor base distal end 1626. Connected to sensor base proximal end 1624 is an electrical connection 1632 that connects sensor base 1612 to a monitoring device (not shown in FIG. 16). Cylindrical body 1622 includes an exterior screw thread 1634. Sensor base distal end 1626 includes a disc-shaped recess 1636.

Electrode cell assembly 1614 includes a disc-shaped assembly base 1640 having a proximal side 1642, a distal side 1644 and an outside edge 1646. Mounted on proximal side 1642 is a working electrode assembly 1652, a counter electrode 1654 that is in the shape of an open rectangle surrounding working electrode assembly 1642 and a reference electrode 1656. Working electrode assembly 1652 comprises two array, arrays 1662 and 1664 of carbon nanotubes. Arrays 1662 and 1664 each function as working electrodes. Proximal side 1642 includes respective contacts (not shown) that are in electrical communication with counter electrode 1654, reference electrode 1656, array 1662 and array 1664 and that contact respective contacts (not shown) in recess 1636 when electrode cell assembly is mounted in recess 1636. The contacts in recess 1636 are in electrical communication with wires that extend through cylindrical body 1622 and are connected with respective wires (not show) in electrical connection 1632. The carbon nanotubes of array 1662 have a first functionality. The carbon nanotubes of array 1664 have a second functionality. The first and second functionalities may be different or the same depending on how arrays 1662 and 1664 are used.

Cap 1616 is made of an insulating material such as plastic and includes a interior screw thread 1672 that may be used to screw onto sensor base 1612 using exterior screw thread 1634. Cap 1616 includes an opening 1674 that allows a water sample containing one or more analytes of interest to contact arrays 1662 and 1664 of working electrode assembly 1652, counter electrode 1654 and reference electrode 1656 when sensor device 1602 is immersed in a water sample. Opening 1674 is smaller in diameter than assembly base 1640 because cap 1616 includes a lip 1676 extends over outside edge 1646 when cap 1616 is screwed onto sensor base 1612, thereby holding electrode assembly 1614 in place in recess 1636. When fully screwed onto sensor base 1612, lip 1676 will contact distal end 1626 of sensor base 1612.

Figure 17:
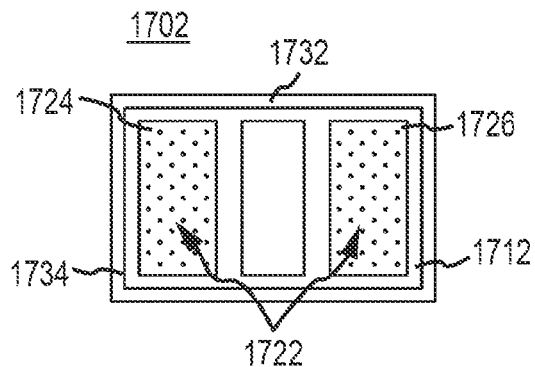
FIG. 17 is a top plan view in simplified form of an electrode cell assembly in accordance with one embodiment of the present invention.
Figure 18:
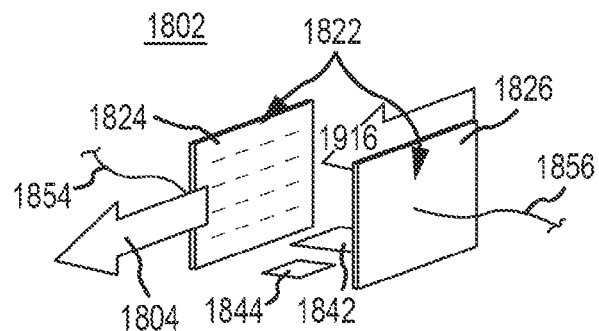
FIG. 18 is a perspective view in simplified form of an electrode cell assembly in accordance with one embodiment of the present invention.

In some embodiments, instead of the arrays of the working electrode assembly being adjacent to each other as shown in FIGS. 14, 15 and 16, the arrays of the working electrode assembly may be separated from each other as shown in FIGS. 17 and 18 below.

FIG. 17 shows an electrode cell assembly 1702 according to one embodiment of the present invention. Electrode cell assembly 1702 includes a plate 1712 on which is mounted a working electrode assembly 1722 comprising two arrays, arrays 1724 and 1726 of carbon nanotubes. Arrays 1724 and 1726 each function as working electrodes. Arrays 1724 and 1726 are on either side of a reference electrode 1732 mounted on plate 1712. A counter electrode 1734 mounted on plate 1712 is in the shape of an open rectangle surrounding working electrode assembly 1722 and reference electrode 1732. A back side of plate 1712 (not shown) includes respective contacts in electrical communication with array 1724, array 1726, reference electrode 1732 and counter electrode 1734. The carbon nanotubes of array 1724 have a first functionality. The carbon nanotubes of array 1726 have a second functionality. The first and second functionalities may be different or the same depending on how arrays 1724 and 1726 are used. Electrode cell assembly 1702 could be used in place of the electrode cell assembly of FIG. 16 or in other applications where a compact electrode cell assembly is desirable.

FIG. 18 shows an electrode cell assembly 1802 according to one embodiment of the present invention that is part of a flow cell (not shown) for a water sample containing one or more analytes of interest. The water sample flows in the direction of arrows 1804. Electrode cell assembly 1802 a working electrode assembly 1822 comprising two arrays, arrays 1824 and 1826 of carbon nanotubes that are mounted in parallel to each other on opposite walls of the flow cell. Arrays 1824 and 1826 each function as a separate working electrode. A counter electrode 1842 and reference electrode 1844 are mounted on a bottom wall of the flow cell. Respective electrical connections 1854 and 1856 to arrays 1824 and 1826 allow sensor readings to be obtained from arrays 1824 and 1826, respectively. The carbon nanotubes of array 1824 have a first functionality. The carbon nanotubes of array 1826 have a second functionality. The first and second functionalities may be different or the same depending on how arrays 1824 and 1826 are used.

Figure 19:
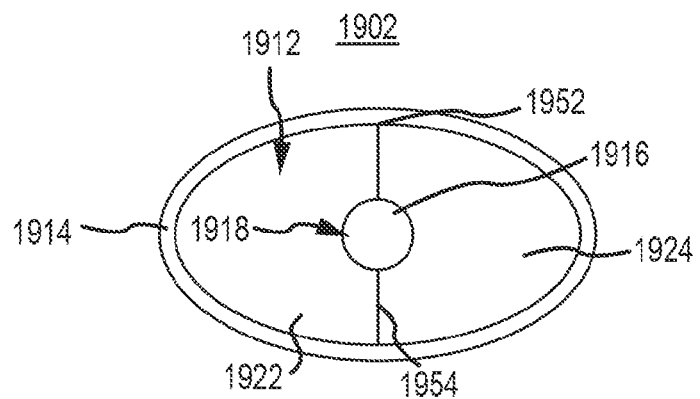
FIG. 19 is a top plan view in simplified form of an electrode cell assembly in accordance with one embodiment of the present invention.

There working electrode assembly, reference electrode, counter electrode and arrays of carbon nanotubes may have a variety of different shapes. For example, FIG. 19 shows an electrode cell assembly 1902 having a working electrode assembly 1912 that is oval in shape and an open oval-shaped counter electrode 1914 that surrounds the working electrode. A circular reference electrode 1916 is located in an opening 1918 in working electrode assembly 1912. Working electrode assembly 1912 comprises two arrays, arrays 1922 and 1924 of carbon nanotubes. Arrays 1922 and 1922 each function as a separate working electrode. The carbon nanotubes of array 1924 have a first functionality. The carbon nanotubes of array 1926 have a second functionality. The first and second functionalities may be different or the same depending on how arrays 1922 and 1924 are used. Arrays 1924 and 1926 have two bordering edges 1952 and 1954 where arrays 1924 and 1926 border each other.

Figure 20:
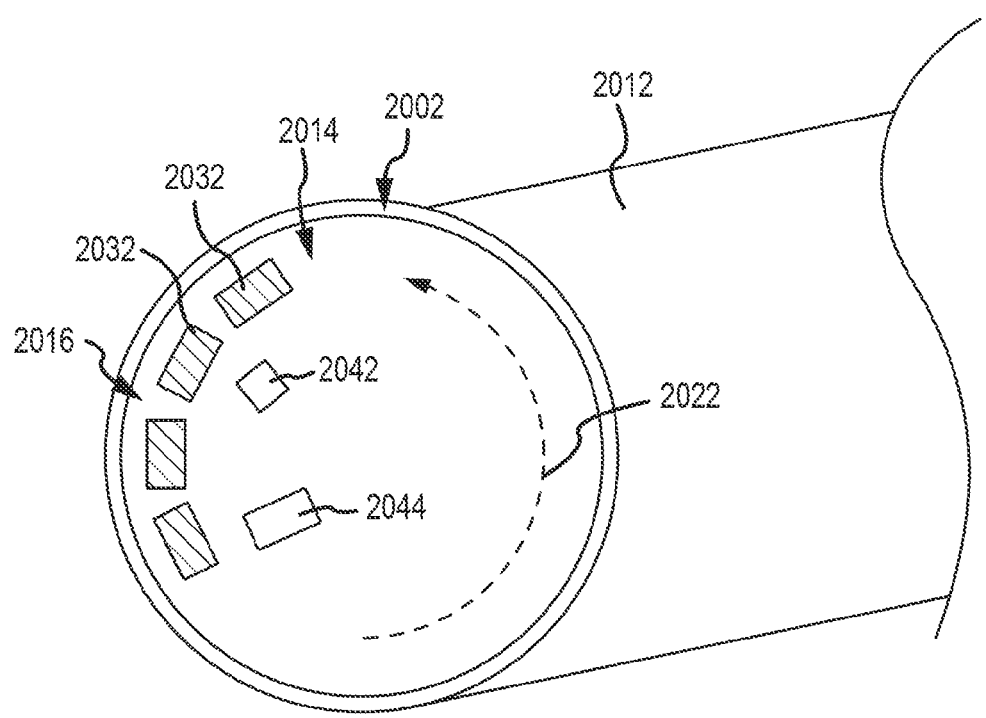
FIG. 20 is a perspective view in simplified form of part of an open pipe sensor in accordance with one embodiment of the present invention.

FIG. 20 shows an open pipe sensor 2002 mounted in a pipe 2012 (such as a water pipe) having an interior surface 2014. At a distal end 2016 of interior surface 2014 there is mounted a working electrode assembly 2016 around the entire circumference of interior surface 2014 as indicated by arrow 2022. Working electrode assembly 2016 comprises multiple arrays 2032 of carbon nanotubes. Each array 2032 functions as a separate working electrode and may be used to detect a different analyte. Only a few of arrays 2032 are shown in FIG. 20 for simplicity of illustration. A reference electrode 2042 and a counter electrode 2044 are also mounted on interior surface 2014. The carbon nanotubes of each of arrays 2032 may be different or the carbon nanotubes of two or more of the arrays may have the same functionality depending on how arrays 2032 are use. The different arrays of the present invention may also cross correlate to a water analysis parameter of interest, thus providing for an in-line water quality analysis kit.

The open pipe sensor of FIG. 20 may be manufactured as part of the pipe or may be made as a separate circular insert that is inserted in the pipe. The open pipe sensor could even be in a form of a piece of tape that is adhered to the interior surface of the pipe.

The carbon nanotube arrays of the present invention may also be used with a single filter that modifies the entire array as a whole or with individual filters for each carbon nanotube of an array.

Figure 21:
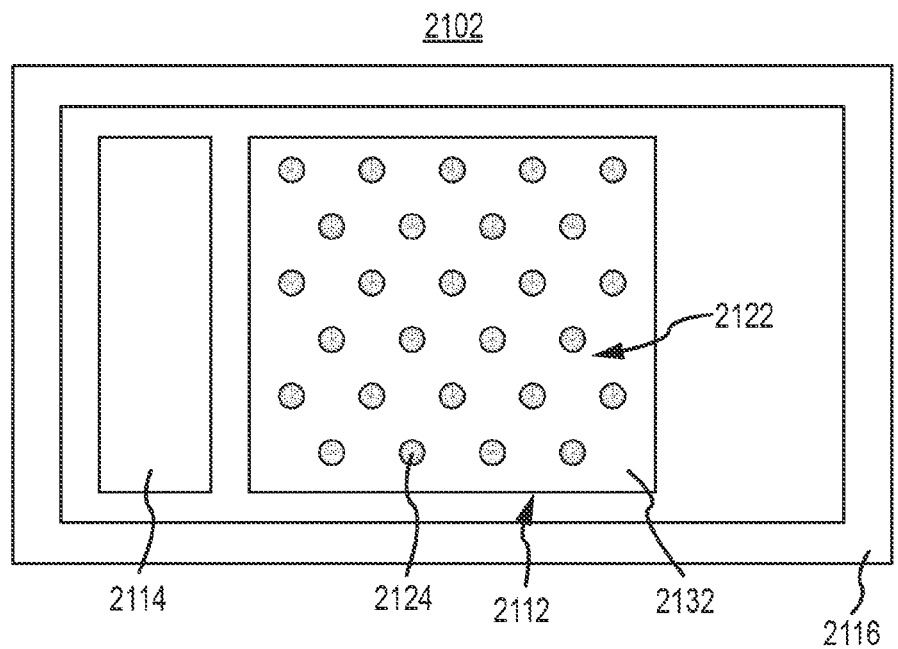
FIG. 21 is a top plan view in simplified form of an electrode cell assembly in accordance with one embodiment of the present invention.
Figure 22:
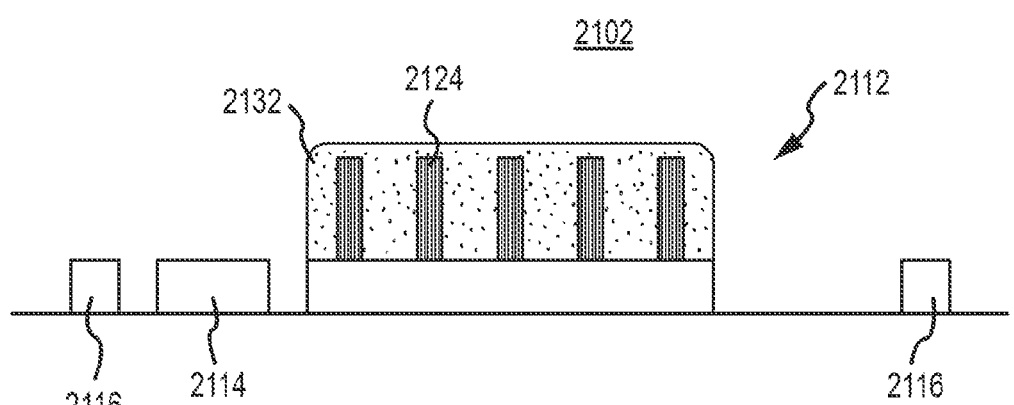
FIG. 22 is a cross-sectional view of the electrode cell assembly of FIG. 21.

FIGS. 21 and 22 show an electrode cell assembly 2102 according to one embodiment of the present invention comprising a working electrode 2112, a reference electrode 2114 and a counter electrode 2118 mounted on a substrate 2120. Counter-electrode 2118 has an open rectangular shape and surrounds working electrode 2112 and reference electrode 2114. Working electrode 2112 comprises an array 2122 of carbon nanotubes 2124 mounted on a working electrode base 2126. Working electrode 2112 also includes a filter material 2132 that covers all of array 2122. Depending on the application, carbon nanotubes 2124 may each have different functionalities or two or more of the carbon nanotubes may have the same functionality.

Figure 23:
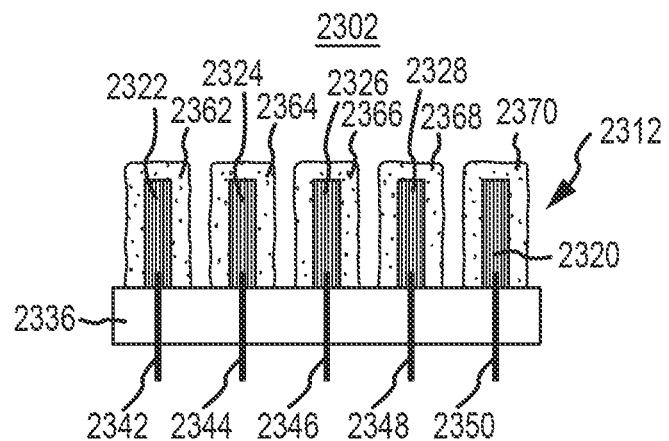
FIG. 23 is a cross-sectional view in simplified form of an electrode cell assembly in accordance with one embodiment of the present invention.

FIG. 23 shows a working electrode assembly 2302 comprising an array 2312 of carbon nanotubes of which only five carbon nanotubes 2322, 2324, 2326, 2328 and 2330 are shown. Carbon nanotubes 2322, 2324, 2326, 2328 and 2330 are each bound to a substrate 2336 of working electrode assembly 2302. Carbon nanotubes 2322, 2324, 2326, 2328 and 2330 are connected to a sensor device (not shown) by respective electrical connections 2342, 2344, 2346, 2348 and 2350 that extend through substrate 2336. If electrical connections 2342, 2344, 2346, 2348 and 2350 are connected to each other, carbon nanotubes 2322, 2324, 2326, 2328 and 2330 function together as a single working electrode. If electrical connections 2342, 2344, 2346, 2348 and 2350 are independent of each other, carbon nanotubes 2322, 2324, 2326, 2328 and 2330 may each function as an independent working electrode. Respective filter material coatings 2362, 2364, 2366, 2368 and 2370 coat respective carbon nanotubes 2322, 2324, 2326, 2328 and 2330. Depending on the application, filter material coatings 2362, 2364, 2366, 2368 and 2370 may each be the different or two or more of the filter material coatings may be the same. Depending on the application, carbon nanotubes 2322, 2324, 2326, 2328 and 2330 may each have different functionalities or two or more of the carbon nanotubes may have the same functionality.

The filter materials that may be used include any application specific ion or analyte selective material. For instance, for chromate analysis the filter material may include a Bis (acetylacetonato) cadminum II based ion selective material embedded in an appropriate polymeric matrix. For enzyme detection the filter material be include a gas permeable silicone rubber material. For cation detection the filter may include a companion ionophore embedded in a suitable polymer. For sodium detection the filter may include crown esters and/or dibenzopyrindo-18-Crown-6 embedded in a suitable polymer. For potassium detection the filter may include valinomycin embedded in a suitable polymer. For beryllium detection the filter may include benzo-9-crown-3 embedded in a suitable polymer. For $H_3O^+$ detection the filter may include aminated and carboxylated poly(vinylchloride). These examples are for illustrative purposes, however, any ion selective, or biologically active receptor model, based material could be used as a component of the filter material.

Figure 24:
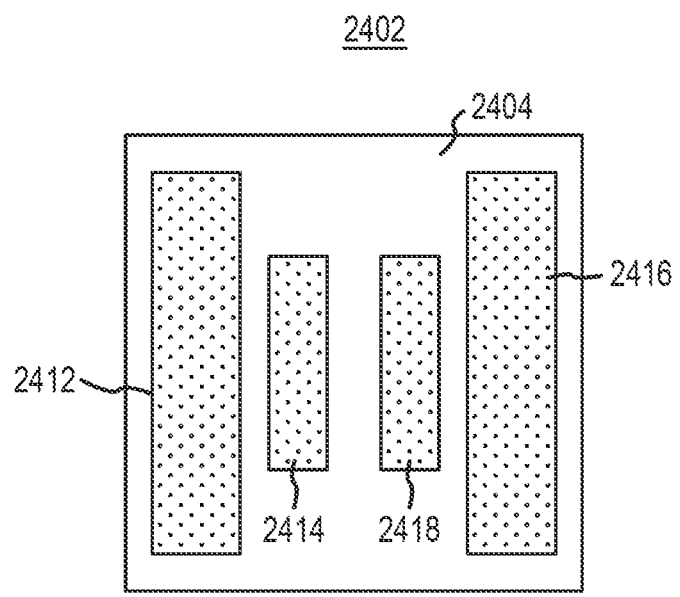
FIG. 24 is a top plan view in simplified form of a working electrode assembly in accordance with one embodiment of the present invention.

In another embodiment, the coating material could be a metal or metal oxide coating. For instance, TiO2 or RuO2, or gold, silver, or any other elemental coating. By coating the CNTs, as a substructure, with a metal oxide or metal it is possible to generate three dimensional structures that can be used directly for analysis, or they can be functionalized for additional analyte specificity. This arrangement may be employed as a four (4) electrode conductivity sensor FIG. 24 shows another way of altering the environment of an array of carbon nanotubes. FIG. 24 shows a working electrode assembly 2402 comprising a substrate 2404, a drive electrode 2412, a sense electrode 2414, a drive electrode 2416 and a sense electrode 2418 that each comprise an array of carbon nanotubes. Drive electrode 2412 may be made a cathode or anode to affect the pH environment around sense electrode 2414. Similarly, drive electrode 2416 may be made a cathode or anode to affect the pH environment around sense electrode 2418.

Figure 25:
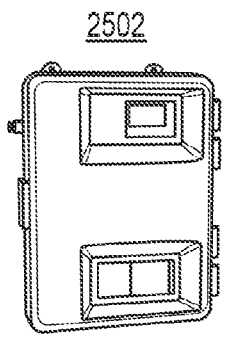
FIG. 25 shows a water analyzing device in which is mounted an electrode cell assembly in accordance with one embodiment of the present invention.
Figure 26:
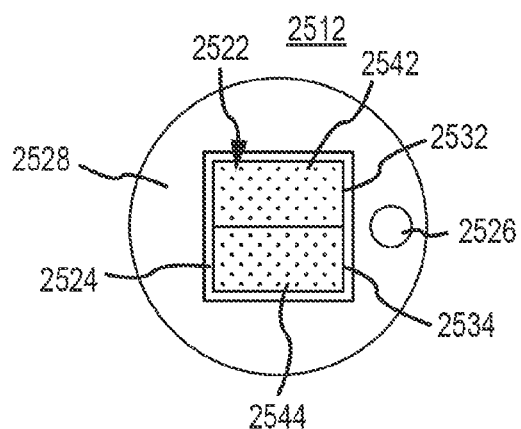
FIG. 26 is an electrode cell assembly of the water analyzing device of FIG. 25.
Figure 27:
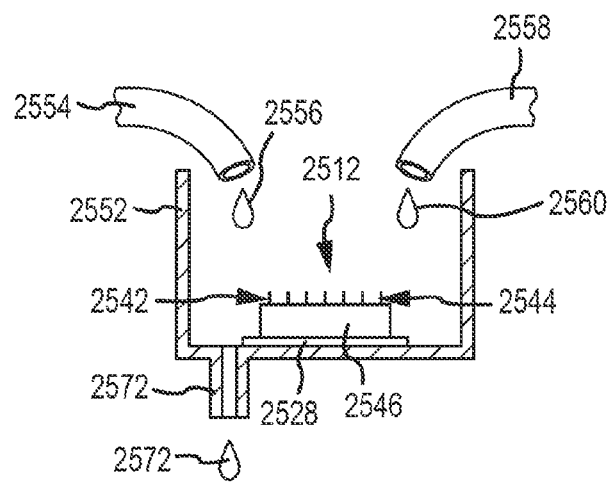
FIG. 27 is a cross-sectional view in simplified form of a portion of the water analyzing device of FIG. 25.

FIGS. 25, 26 and 27 shows how an electrode cell assembly employing one or more working electrodes each comprising an array carbon nanotube array may be used with a colorimetric water analyzing device, such as a Hach model CL17™ chlorine analyzer. FIGS. 25, 26 and 27 show a colorimetric analyzing device 2502 in which is mounted an electrode cell assembly 2512 comprising a working electrode assembly 2522, a counter electrode 2524 and a reference electrode 2526 that are all mounted on an cell assembly substrate 2528. Counter electrode 2524 has an open rectangular shape and surrounds working electrode assembly 2522. Working electrode assembly 2522 comprises two working electrodes, working electrodes 2532 and 2534. Working electrode 2532 comprises an array of carbon nanotubes 2542. Working electrode 2534 comprises an array of carbon nanotubes 2544. Carbon nanotubes 2542 and 2544 are bound to substrate 2546. Depending on the application, carbon nanotubes 2542 and 2544 may the same or different functionalities. FIG. 27 shows electrode cell assembly 2514 mounted in a chamber 2552 that functions as a sensing region of colorimetric analyzing device 2502. A source 2554 of a water sample 2556 and a source 2558 of a reagent 2560, such as a pH indicator, are supplied to chamber 2552 where water sample 2556 and reagent 2560 are mixed and sensed by working electrodes 2542 and 2544. If the functionalities of carbon nanotubes 2542 and 2544 are different, working electrodes 2532 and 2534 may sense different analytes in water sample 2556. In one embodiment, working electrode 2532 and/or working electrode 2534 may sense $Cl_2$ present in water sample 2556. A drain 2572 allows for the waste mixture 2574 of water sample 2556 and reagent 2560 to flow through chamber 2552.

In one embodiment of the present invention, a water analyzing device may just employ an electrode cell assembly and chamber of the type shown in FIGS. 26 and 27 without including the components for colorimetric analysis. Such a water analyzing device may be made very compactly.

Figure 28:
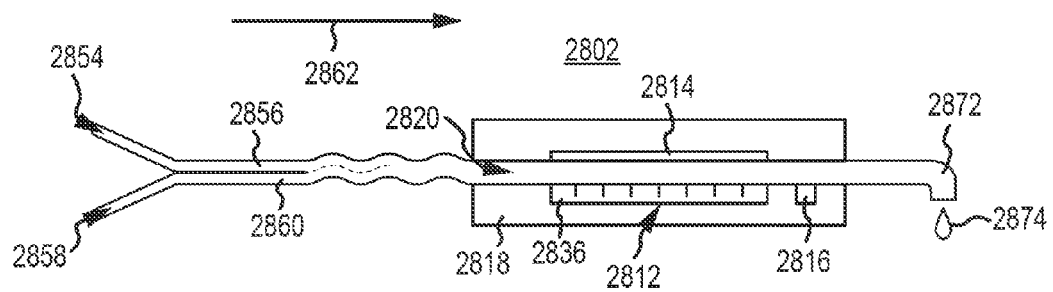
FIG. 28 is a cross-sectional view of a portion of a water analyzing device in accordance with one embodiment of the present invention.
Figure 29:
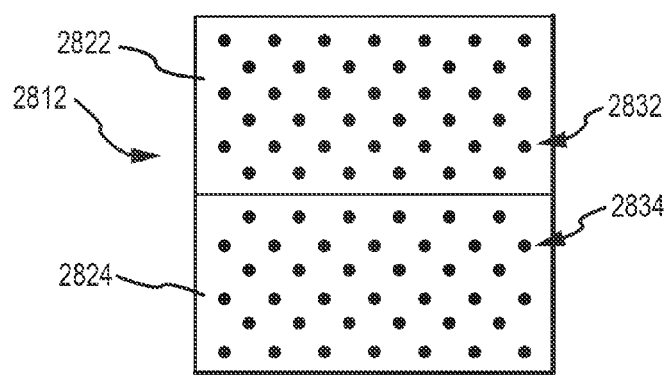
FIG. 29 is a cross-sectional view of a working electrode of the water analyzing device of FIG. 28.

FIGS. 28 and 29 show a water analyzing device 2802 in which is mounted a working electrode assembly 2812, a counter electrode 2814 and a reference electrode 2816 mounted in a body 2818 of analyzing device 2802 and in contact with a water passageway 2820 that functions as a sensing region. Working electrode assembly 2812 comprises two working electrodes, working electrodes 2822 and 2824. Working electrode 2822 comprises an array of carbon nanotubes 2832. Working electrode 2824 comprises an array of carbon nanotubes 2834. Carbon nanotubes 2832 and 2834 are bound to substrate 2836. Depending on the application, carbon nanotubes 2832 and 2834 may have the same or different functionalities. A source 2854 of a water sample 2856 and a source 2858 of a reagent 2860, such as a pH indicator, are supplied in a flow direction indicated by arrow 2862 to passageway 2820 where water sample 2856 and reagent 2860 are mixed and sensed by working electrodes 2842 and 2844. If the functionalities of carbon nanotubes 2842 and 2844 are different, working electrodes 2832 and 2834 may sense different analytes in water sample 2856. In one embodiment, working electrode 2832 and/or working electrode 2834 may sense $Cl_2$ present in water sample 2856. A drain 2872 allows for the waste mixture 2874 of water sample 2856 and reagent 2860 to flow through passageway 2820.

Table 1 of FIG. 30 show some of the substituents with which carbon nanotubes of the present invention may be functionalized to detect particular analytes. For example, to detect pH, the carbon nanotubes may be functionalized by binding vinyl-ferrocene or ferrocene carboxaldehyde, i.e. organometallic substituents, to the carbon nanotubes. To detect chlorine, substituent 3112 may be bound to an array of carbon nanotubes. To detect fluoride, substituent 3014 may be bound to an array of carbon nanotubes.

FIG. 31 shows an array 3102 of carbon nanotubes 3112 according to one embodiment of the invention in which carbon nanotubes 3112 are grown in a random configuration on a substrate 3114.

FIG. 32 shows two arrays 3202 and 3204 of carbon nanotubes 3212 and 3214, respectively that are grown in horizontally stacked configurations on a substrate 3216. Carbon nanotubes 3212 are shorter than carbon nanotubes 3214. Carbon nanotubes 3212 and 3214 are grown a direction shown by arrow 3322.

FIG. 33 shows an array 3302 of carbon nanotubes 3312 according to one embodiment of the invention in which carbon nanotubes 3312 are grown in a vertically stacked configuration on a substrate 3314.

FIG. 34 shows an end 3402 of a carbon nanotube 3404 have an open headed configuration. FIG. 35 shows an end 3502 of a carbon nanotube 3504 having a capped configuration.

In one embodiment of the present invention, substrate may be made of silicon or graphite upon which the carbon nanotubes are grown.

According to a aspect of the present invention, a method is provided comprising the following steps: (a) transmitting data collected from one or more carbon nanotube sensors in the water treatment system to a remote computer disposed at a first distant location from the water treatment system; and (b) generating an output based on the data, wherein the data is transmitted from the water treatment system to the remote computer using a mode of transmission. According to some embodiments, the remote computer may only be connected or linked to the water treatment system via the mode of transmission. According to some embodiments, an analyzer may analyze or manipulate the data to generate the output. The analyzer may comprise a source code or a software program. According to some embodiments, the analyzer may compare the data continuously, in real time, at periodic or selected intervals, on condition, or on demand by a user. According to some embodiments, the output may comprise one or more of the following: data, alarm, analysis result, or analysis report.

According to some of the method embodiments, the water treatment system may comprise a water treatment core facility with the water treatment core facility being a water treatment facility for the distribution of potable drinking water to the public, and the water treatment system may further comprise a distribution system. According to some embodiments, the water treatment system may comprise a water treatment core facility with the water treatment core facility being a wastewater treatment plant (WWTP), and the water treatment system may further comprise a collection system.

According to method embodiments of the present invention, the remote computer may be physically separated from the water treatment system at a distant location, and/or the remote computer may only be connected or linked to the water treatment system via the mode of transmission. According to method embodiments of the present invention, the remote computer itself may comprise may be at least one of the following: a computer, an Internet or web server, a database, or an ftp server. The one or more carbon nanotube sensors detect or measure qualities of water in the water treatment system. According to some embodiments, the one or more carbon nanotube sensors detect or measure one or more of the following qualities of water in the water treatment system: temperature, chemical composition, total organic carbon (TOC), fluid quantity, flow rate, waste product, contaminant, conductivity, pH, dissolved oxygen, pressure, turbidity, permeate flow, chlorine or fluorine concentration, water or tank level, or equipment status or operation. The one or more carbon nanotube sensors may be located at a plurality of locations within the water treatment system. According to some embodiments, the water treatment system includes at least one of the one or more sensors that does not contact the water in the water treatment system. At least one of the one or more sensors not in contact with the water may use radar technology.

According to method embodiments of the present invention, the mode of transmission may vary and may be via one or more of the following: the Internet, TCP/IP, Ethernet, file transfer protocol (ftp), email, such as SMTP, cellular phone network, radios or remote terminal units (RTU) coupled to radio frequency transmitters, satellite transmission, existing telephone or communication networks or wiring, a standard Public Switched Telephone Network (PSTN), a wireless network, a wide area network (WAN), wireless local area network (WLAN), local area network (LAN), or metropolitan area network (MAN), a cable internet connection, short message system (SMS), or a dial-up modem. See description above including additional examples of a mode of transmission. According to some embodiments of the present invention, the data may be transmitted from the water treatment system to the remote computer continuously, in real time, at periodic or selected intervals, on condition, or on demand by a user using the mode of transmission. The data may be transmitted directly from the one or more carbon nanotube sensors to the remote computer using a mode of transmission.

Method embodiments of the present invention may further comprise the step of (c) comparing, analyzing, manipulating, etc., the data using an analyzer. According to some embodiments, the manipulating step (c) may comprise comparing the data to expected or historical data or information and/or comparing the data continuously, in real time, at periodic or selected intervals, on condition, or on demand by a user. According to some embodiments, step (c) may further comprise manipulating the data as well as any other information or data, such as historical data, expected performance, etc. to generate an output.

According to some embodiments, the output may comprise one or more of the following: data, an alarm, an analysis result, and/or an analysis report. According to some embodiments, the manipulating step (c) may be performed after the transmitting step (a). According to these embodiments, the analyzer may be located at a second distant location from the water treatment system. According to these embodiments, the first and second distant locations may also be co-located. According to some embodiments, the analyzer may be associated with the remote computer of the remote monitoring system. According to some of these embodiments, the analyzer may be located on the remote computer.

According to embodiments of the present invention, the water treatment system may include a local computer located at or near the water treatment system. According to some embodiments, the data may be transmitted from the local computer located at or near the water treatment system to the remote computer. According to some embodiments, the manipulating step (c) may be performed prior to the transmitting step (a). The local computer may be a logger device. According to these embodiments, the analyzer may be located on the logger device. The logger device may have one or more sensor ports for receiving data from the one or more carbon nanotube sensors. The data transmitted from the local computer to the remote computer may include observational data. According to some embodiments, the analyzer may be associated with or on the local computer of the remote monitoring system. Thus, according to some embodiments, the data may be transmitted from the water treatment system by the remote computer accessing the data from the water treatment system, such as the one or more carbon nanotube sensors, the electronic control system, and/or the local computer.

According to some method embodiments of the present invention, the water treatment system may include an electronic control system. The electronic control system may be a Supervisory Control and Data Acquisition System (SCADA) or a Programmable Logic Controller (PLC). According to some embodiments, the data may be transmitted from the electronic control system to the remote computer using the mode of transmission.

Method embodiments of the present invention may further comprise the step of (d) communicating the output to a remote viewing device using a mode of communication, wherein step (d) is performed after the generating step (b). According to some embodiments, the output may be accessed from the remote computer or database by a remote viewing device. The remote viewing device may be one or more of the following:

personal computer or terminal, web or Internet server, file transfer protocol (ftp) server, cell phone, pager, or handheld device. According to some embodiments, the output may be downloaded or viewed using the remote viewing device. According to some embodiments, the output may be sent or uploaded to the remote viewing device continuously, in real time, at periodic or selected intervals, on condition, or on demand by a user using the mode of communication. The mode of communication may be one or more of the following: Internet, facsimile, file transfer protocol (ftp), voice or text messaging, text to voice messages, electronic mail, pager, human voice calling, SMS messages, instant messaging or groupware protocols, public switched telephone network, cellular network, wireless or satellite communication, or radio communication. See description above including additional examples of a mode of communication. For example, a user viewing the output communicated in step (d) on a remote viewing device may be any one or more of the following: regulator, law enforcement officer, elected official, manager or operator of a water treatment system, vendor customer, member of the public, etc. According to some embodiments, the output may be communicated or submitted to a regulatory and/or law enforcement agency in step (d).

Method embodiments of the present invention may further comprise the step of (e) storing the data on a remote database associated with the remote computer, wherein step (e) may be performed after the generating step (b). According to some embodiments, step (e) may be performed after the manipulating step (c) and/or prior to the communicating step (d).

According to another broad aspect of the present invention, a method is provided for monitoring a water treatment system comprising the following steps: (a) collecting data from one or more carbon nanotube sensors located in the water treatment system; and (b) transmitting the data to a remote computer disposed at a first distant location from the water treatment system using a mode of transmission. According to some embodiments, the method may further comprise the step of (c) generating an output based on the data, wherein step (c) is performed after the transmitting step (b). According to some embodiments, the method may further comprise the step of (d) communicating the output to a remote viewing device using a mode of communication, wherein step (d) is performed after the transmitting step (b).

Method embodiments of the present invention may further comprise the step of (e) manipulating the data using an analyzer. According to some embodiments, step (e) is performed prior to step (b). According to these embodiments, the analyzer may be associated with a local computer. According to other embodiments, step (e) may be performed after the transmitting step (b). According to these embodiments, the analyzer may be associated with the remote computer.

Having described many embodiments of the present invention, it will be apparent that modifications, variations, alterations, and changes are possible without departing from the full scope of the invention as defined in the appended claims, and equivalents thereof. It should be appreciated that all examples in the present disclosure, while illustrating many embodiments of the invention, are provided as non-limiting examples and are, therefore, not to be taken as limiting the various aspects so illustrated.

What is claimed is:

1. A sensing device, comprising:
   a substrate; and
   four carbon nanotube arrays arranged on the substrate, each one of said four carbon nanotube arrays individually including:
      a plurality of carbon nanotube rows, each row including a plurality of carbon nanotubes, each carbon nanotube in a respective row being directly bound at one end to the substrate,
      first and second contiguous array sections, the first array section including at least two rows of the plurality of carbon nanotube rows, and the second array section including at least one row of the plurality of carbon nanotube rows, the carbon nanotubes within an array section having the same functionality,
      each array section being configured to be individually addressable, such that all carbon nanotubes within the array section are addressable via a common connection line, and
      each array section being configured to sense a corresponding analyte when exposed to a fluid solution containing one or more analytes.

2. The sensing device of claim 1, wherein the carbon nanotubes in the first array section having a first functionality and the carbon nanotubes in the second array section having a second functionality.

3. The sensing device of claim 2, wherein the first functionality is different from the second functionality.

4. The sensing device of claim 2, wherein the first functionality is the same as the second functionality.

5. The sensing device of claim 1, wherein the at least two carbon nanotube rows are adjacent carbon nanotube rows.

6. The sensing device of claim 1, wherein the carbon nanotube rows in the first section and the carbon nanotube rows in the second section are alternating carbon nanotube rows.

7. The sensing device of claim 1, wherein the two array sections sense different analytes.

8. The sensing device of claim 1, wherein the carbon nanotubes in at least one array section are hydrophilic.

9. The sensing device of claim 1, wherein the first array section is separated from the second array section by a distance which is substantially the same as a distance between two adjacent rows of said plurality of carbon nanotube rows.

* * * * *